US007038085B2

(12) United States Patent
Rariy et al.

(10) Patent No.: US 7,038,085 B2
(45) Date of Patent: May 2, 2006

(54) STEREOISOMERS OF P-HYDROXY-MILNACIPRAN, AND METHODS OF USE THEREOF

(75) Inventors: Roman V. Rariy, Allston, MA (US); Michael Heffernan, Hingham, MA (US); Stephen L. Buchwald, Newton, MA (US); Timothy M. Swager, Newton, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 0 days.

(21) Appl. No.: 10/691,465

(22) Filed: Oct. 22, 2003

(65) Prior Publication Data
US 2004/0142904 A1    Jul. 22, 2004

Related U.S. Application Data

(60) Provisional application No. 60/445,142, filed on Feb. 5, 2003, provisional application No. 60/423,062, filed on Nov. 1, 2002, provisional application No. 60/421,640, filed on Oct. 25, 2002.

(51) Int. Cl.
*C07C 233/05* (2006.01)
*A61K 31/165* (2006.01)

(52) U.S. Cl. .................. 564/165; 564/164; 564/171; 564/190; 514/620; 514/624

(58) Field of Classification Search ............... 564/164, 564/165, 171, 190; 514/620, 624
See application file for complete search history.

(56) References Cited

U.S. PATENT DOCUMENTS

| 4,478,836 | A | 10/1984 | Mouzin et al. |
| 5,621,142 | A | 4/1997 | Mochizuki et al. |
| 6,602,911 | B1 * | 8/2003 | Kranzler et al. ............ 514/624 |

FOREIGN PATENT DOCUMENTS

JP         3-56415      3/1991

OTHER PUBLICATIONS

Registry No. 136091-14-0(Belongs to JP 3-56415), 1991.*
Moret, C., et al., "Biochemical Profile of Midalcipran (F 2207), 1-Phenyl-1-Diethyl-Aminocarbonyl-2-Aminomethyl-Cyclopropane (Z) Hydrochloride, A Potential Fourth Generation Antidepressant Drug," *Neuropharmacology*, vol. 24, No. 12, pp. 1211-1219, (1985).

Gard, S., et al., "Enhancement of Second-Migrating Enantiomer Peak Symmetry of Basic Drugs by Using Dual-Cyclodextrin System in Capillary Electrophoresis," *Electrophoresis 2000*, N. 21, pp. 3028-3034, (2002).
Bonnaud, B., et al., "1-Aryl-2(Aminomethyl) cyclopropanecarboxylic Acid Derivatives. A New Series of Potential Antidepressants," *J. Med. Chem. 1987*, No. 30, pp. 318-325 (1987).
Shuto, S., et al., "(±)-(Z)-2-(Aminomethyl)-1-phenylcyclopropanecarboxamide Derivatives as a New Prototype of NMDA Receptor Antagonists," *U. Med. Chem*, 1995, No. 38, pp. 2964-2968, (1995).
Viazzo, P., et al. "Microbiological Transformations 34: Enantioselective Hydrolysis of a Key-Lactone Involved in the Synthesis of the Antidepressant Milnacipran®," *Tetrahedron Letters*, vol. 37, No. 26, pp. 4519-4522 (1996).
Shuto, S., et al., "Synthesis of (+)- and (−)-Milnaciprans and Their Conformationally Restricted Analogs," *Tetrahedron Letters*, vol. 37, No. 5, pp. 641-644 (1996).
Shuto, S., et al., "Synthesis and Biological Activity of Conformationally Restricted Analogs of Milnacipran: (IS, 2R)-1-Phenyl-2-[(S)-1-aminopropyl]N,N-diethylcyclopropanecarboxamide, and Efficient Noncompetitive N-Methyl-D-aspartic Acid Receptor Antagonist," *J. Med. Chem. 1996*, No. 39, pp. 4844-4852, (1996).

(Continued)

*Primary Examiner*—Shailendra Kumar
(74) *Attorney, Agent, or Firm*—Dana M. Gordon; Foley Hoag LLP

(57) ABSTRACT

The present invention relates generally to the enantiomers of para-hydroxy-milnacipran or congeners thereof. Biological assays revealed that racemic para-hydroxy-milnacipran is approximately equipotent in inhibiting serotonin and norepinephrine uptake ($IC_{50}$=28.6 nM for norepinephrine, $IC_{50}$=21.7 nM for serotonin). Interestingly, (+)-para-hydroxy-milnacipran is a more potent inhibitor of norepinephrine uptake than serotonin uptake ($IC_{50}$=10.3 nM for norepinephrine, $IC_{50}$=22 nM for serotonin). In contrast, (−)-para-hydroxy-milnacipran is a more potent inhibitor of serotonin uptake compared to norepinephrin uptake ($IC_{50}$=88.5 nM for norepinephrine, $IC_{50}$=40.3 nM for serotonin). The invention also relates to salts and prodrug forms of the aforementioned compounds. In certain embodiments, the compounds of the present invention and a pharmaceutically acceptable excipient are combined to prepare a formulation for administration to a patient. Finally, the present invention relates to methods of treating mammals suffering from various afflictions, e.g., depression, chronic pain, or fibromyalgia, comprising administering to a mammal in need thereof a therapeutically effective amount of a compound of the present invention.

38 Claims, 63 Drawing Sheets

OTHER PUBLICATIONS

Shuto, S., et al., "Synthesis and Biological Activity of Conformationally Restricted Analogs of Milnacipran: (1S,2R)-1-Phenyl-2-[(R)-1-amino-2-propynyl]-N,N-diethylcyclopropanecarboxamide Is a Novel Class of NMDA Receptor Channel Blocker," *J. Med. Chem. 1998, 41,* pp. 3507-3514, (1998).

Deprez, D., et al., "Which Bioequivalence Study for a Racemic Drug? Application to Milnacipran," *Eur. J. Drug Metab. Pharmacokinet, 23,* pp. 166-171, (1998).

Puzzo, C., et al., "Pharmacokinetics of Milnacipran in Liver Impairment," *Eur. J. Drug Metab. Pharmacokinet, 23,* pp. 273-279, (1998).

Puzzo, C., et al., "Pharmacokinetics of Milnacipran in Renal Impairment," *Eur. J. Drug Metab. Parmacokinet, 23,* pp. 280-286, (1998).

Shuto, S., et al., "(1S,2R)-1-Phenyl-2-[(S)-1-aminopropyl]-N,N-diethylcyclopropanecarboxamide (PPDC), a New Class of NMDA-Receptor Antagonist: Molecular Design by a Novel Conformational Restriction Strategy," *Jpn. J. Pharmacol. 85,* pp. 207-213, (2001).

Doyle, M., et al., "A New Enantioselective Synthesis of Milnacipran and an Analogue by Catalytic Asymmetric Cyclopropanatioin," *Adv. Synth. Catal. 2003,* vol. 343, No. 3, pp. 299-302, (2001).

Kazuta, Y., et al., "Synthesis of (1S,2R)-1-Phenyl-2-[(S)-1-aminopropyl]-N,N-diethylcyclopropanecarboxamide (PPDC) Derivatives Modified at the Carbamoyl Moiety As a New Class of NMDA Receptor Antagonists," *Bioorganic & Medicinal Chemistry 10.* pp. 1777-1791, (2002).

Labat, L., et al., "Separation of New Antidepressants and Their Metabolites by Micellar Electrokinetic Capillary Chromatography," *Journal of Chromatography B.,* 773 pp. 17-23, (2002).

\* cited by examiner

Figure 10
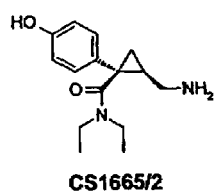
CS1665/2
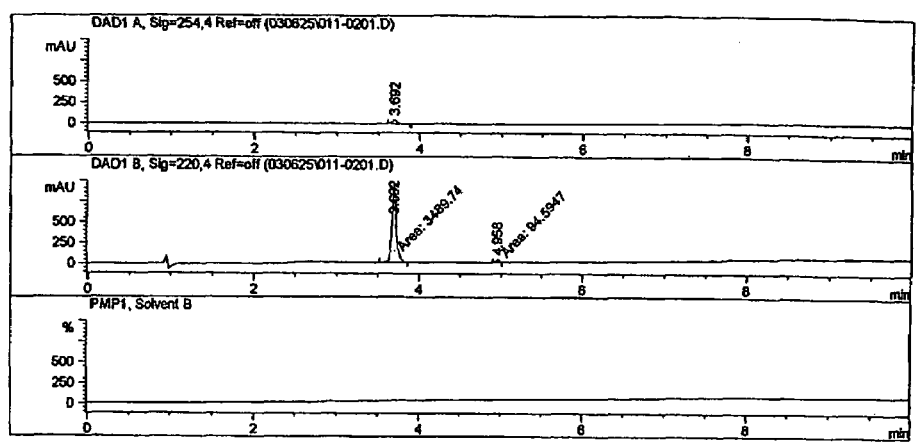

Figure 14
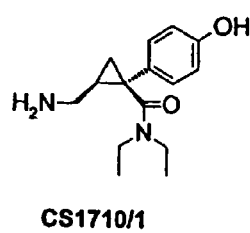
CS1710/1
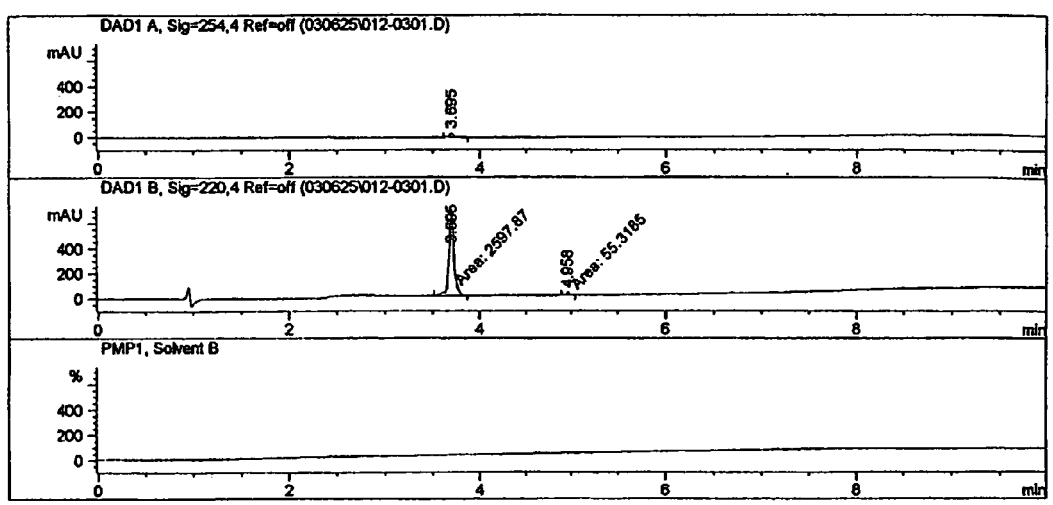

Figure 18
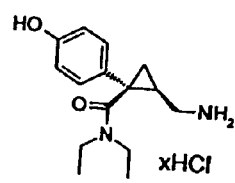
CS1713/1
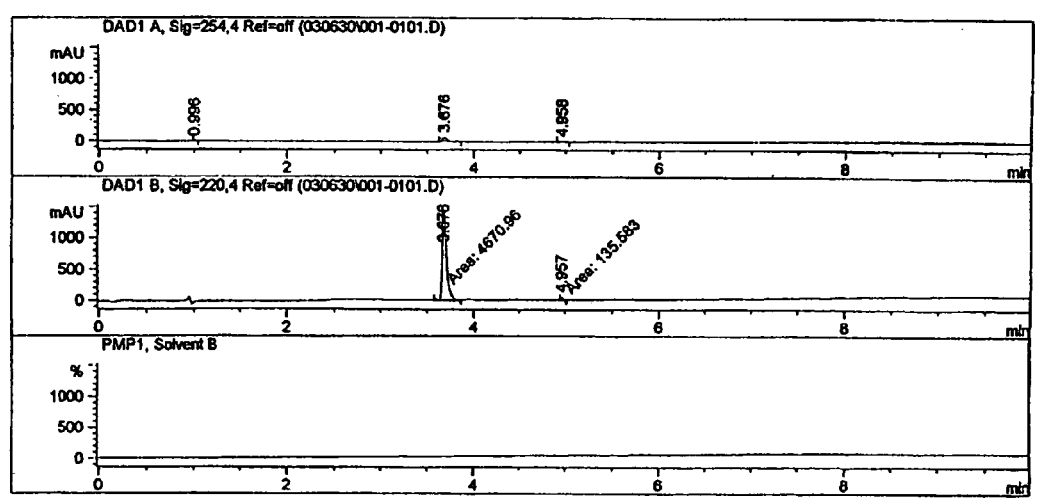

Figure 22
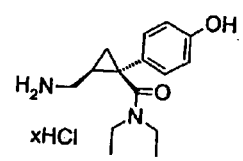
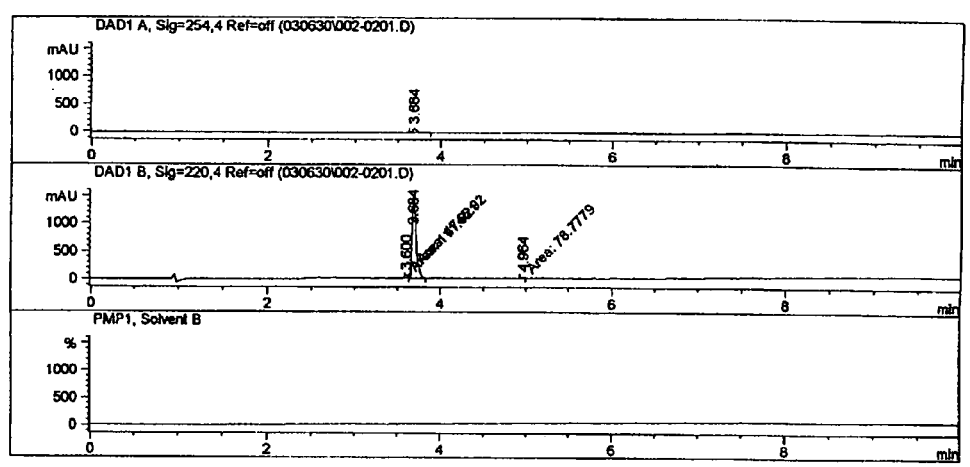

Figure 32

| CAT. # | TARGET | BATCH* | SPP. | n= | CONC. | †% INHIBITION -100 -50 0 50 100 % ↓ ↓ ↓ ↓ ↓ | IC$_{50}$ | K$_i$ | n$_H$ | R |
|---|---|---|---|---|---|---|---|---|---|---|
| 118050 | CYP450, 1A2 | 93172 | hum | 2 | 10 µM | 1 | | | | |
| 118070 | CYP450, 2C19 | 93174 | hum | 2 | 10 µM | 13 | | | | |
| 118060 | CYP450, 2C9 | 93173 | hum | 2 | 10 µM | 7 | | | | |
| 118080 | CYP450, 2D6 | 93175 | hum | 2 | 10 µM | 16 | | | | |
| 118090 | CYP450, 3A4 | 92943 | hum | 2 | 10 µM | 21 | | | | |
| 200510 | Adenosine A$_1$ | 92728 | hum | 2 | 10 µM | -5 | | | | |
| 200610 | Adenosine A$_{2A}$ | 92729 | hum | 2 | 10 µM | -2 | | | | |
| 203100 | Adrenergic α$_{1A}$ | 92918 | rat | 2 | 10 µM | 16 | | | | |
| 203200 | Adrenergic α$_{1B}$ | 92919 | rat | 2 | 10 µM | 5 | | | | |
| 203400 | Adrenergic α$_{1D}$ | 92920 | hum | 2 | 10 µM | 10 | | | | |
| 203620 | Adrenergic α$_{2A}$ | 92621 | hum | 2 | 10 µM | 15 | | | | |
| 203710 | Adrenergic α$_{2B}$ | 92922 | hum | 2 | 10 µM | 14 | | | | |
| 204010 | Adrenergic β$_1$ | 92731 | hum | 2 | 10 µM | 8 | | | | |
| 204110 | Adrenergic β$_2$ | 92732 | hum | 2 | 10 µM | 3 | | | | |
| 212500 | Bradykinin B$_1$ | 92644 | hum | 2 | 10 µM | 10 | | | | |
| 212610 | Bradykinin B$_2$ | 92828 | hum | 2 | 10 µM | 20 | | | | |
| 214510 | Calcium Channel L-Type, Benzothiazepine | 92613 | rat | 2 | 10 µM | 26 | | | | |
| 214600 | Calcium Channel L-Type, Dihydropyridine | 92614 | rat | 2 | 10 µM | -14 | | | | |
| 216000 | Calcium Channel N-Type | 92708 | rat | 2 | 10 µM | -5 | | | | |
| 219500 | Dopamine D$_1$ | 92810 | hum | 2 | 10 µM | -4 | | | | |
| 219600 | Dopamine D$_{2L}$ | 92811 | hum | 2 | 10 µM | -4 | | | | |
| 219800 | Dopamine D$_3$ | 92813 | hum | 2 | 10 µM | -11 | | | | |
| 219900 | Dopamine D$_{4.2}$ | 92814 | hum | 2 | 10 µM | -1 | | | | |
| 224010 | Endothelin ET$_A$ | 92735 | hum | 2 | 10 µM | 0 | | | | |
| 224110 | Endothelin ET$_B$ | 92736 | hum | 2 | 10 µM | -5 | | | | |
| 225500 | Epidermal Growth Factor (EGF) | 92641 | hum | 2 | 10 µM | 3 | | | | |
| 226010 | Estrogen ERα | 92633 | hum | 2 | 10 µM | 7 | | | | |
| 226500 | GABA$_A$, Agonist Site | 92616 | rat | 2 | 10 µM | -10 | | | | |
| 226600 | GABA$_A$, Benzodiazepine, Central | 92830 | rat | 2 | 10 µM | -3 | | | | |
| 228510 | GABA$_B$, Non-Selective | 92715 | rat | 2 | 10 µM | 9 | | | | |
| 232010 | Glucocorticoid | 92894 | hum | 2 | 10 µM | 0 | | | | |

*Batch: Represents compounds tested concurrently in the same assay(s).

†Results with ≥ 50% stimulation or inhibition are boldfaced. (Negative values correspond to <u>stimulation</u> of binding or enzyme activity)
R=Additional Comments
gp=guinea pig; hum=human; syh=syrian hamster

Figure 33

| CAT. # | TARGET | BATCH* | SPP. | n= | CONC. | †% INHIBITION -100-50 0 50 100 % ↓ ↓ ↓ ↓ ↓ | IC$_{50}$ | K$_i$ | n$_H$ | R |
|---|---|---|---|---|---|---|---|---|---|---|
| 232700 | Glutamate, Kainate | 92635 | rat | 2 | 10 μM | 4 | | | | |
| 232810 | Glutamate, NMDA, Agonism | 92720 | rat | 2 | 10 μM | -10 | | | | |
| 232910 | Glutamate, NMDA, Glycine | 92912 | rat | 2 | 10 μM | 5 | | | | |
| 233000 | Glutamate, NMDA, Phencyclidine | 92636 | rat | 2 | 10 μM | 0 | | | | |
| 239610 | Histamine H$_1$ | 92617 | hum | 2 | 10 μM | -16 | | | | |
| 239710 | Histamine H$_2$ | 92618 | hum | 2 | 10 μM | 1 | | | | |
| 239810 | Histamine H$_3$ | 92853 | hum | 2 | 10 μM | -7 | | | | |
| 241000 | Imidazoline I$_2$, Central | 92836 | rat | 2 | 10 μM | -7 | | | | |
| 243510 | Interleukin IL-1, Non-Selective | 92929 | mous | 2 | 10 μM | 0 | | | | |
| 250600 | Leukotriene LTD$_4$ | 92643 | gp | 2 | 10 μM | -1 | | | | |
| 252600 | Muscarinic M$_1$ | 92840 | hum | 2 | 10 μM | 2 | | | | |
| 252700 | Muscarinic M$_2$ | 92841 | hum | 2 | 10 μM | 7 | | | | |
| 252800 | Muscarinic M$_3$ | 92842 | hum | 2 | 10 μM | -2 | | | | |
| 257000 | Neuropeptide Y$_1$ | 92820 | hum | 2 | 10 μM | 10 | | | | |
| 257110 | Neuropeptide Y$_2$ | 92821 | hum | 2 | 10 μM | 4 | | | | |
| 258590 | Nicotinic Acetylcholine | 92737 | hum | 2 | 10 μM | 5 | | | | |
| 260110 | Opiate δ (OP1, DOP) | 92824 | hum | 2 | 10 μM | -12 | | | | |
| 260210 | Opiate κ (OP2, KOP) | 92823 | hum | 2 | 10 μM | 6 | | | | |
| 260410 | Opiate μ (OP3, MOP) | 92822 | hum | 2 | 10 μM | -8 | | | | |
| 264500 | Phorbol Ester | 92834 | mous | 2 | 10 μM | 3 | | | | |
| 265010 | Platelet Activating Factor (PAF) | 92835 | hum | 2 | 10 μM | 3 | | | | |
| 265600 | Potassium Channel [K$_{ATP}$] | 92637 | syh | 2 | 10 μM | 9 | | | | |
| 268700 | Purinergic P$_{2X}$ | 92638 | rabbi | 2 | 10 μM | -1 | | | | |
| 268810 | Purinergic P$_{2Y}$ | 92649 | rat | 2 | 10 μM | -1 | | | | |
| 271110 | Serotonin (5-Hydroxytryptamine) 5-HT$_{1A}$ | 92716 | hum | 2 | 10 μM | -1 | | | | |
| 271910 | Serotonin (5-Hydroxytryptamine) 5-HT$_3$ | 92629 | hum | 2 | 10 μM | -1 | | | | |
| 278110 | Sigma σ$_1$ | 92925 | hum | 2 | 10 μM | 16 | | | | |
| 278200 | Sigma σ$_2$ | 92926 | rat | 2 | 10 μM | 1 | | | | |
| 279450 | Sodium Channel, Site 1 | 92838 | rat | 2 | 10 μM | 0 | | | | |
| 279510 | Sodium Channel, Site 2 | 92619 | rat | 2 | 10 μM | 5 | | | | |

*Batch: Represents compounds tested concurrently in the same assay(s).

†Results with ≥ 50% stimulation or inhibition are boldfaced. (Negative values correspond to <u>stimulation</u> of binding or enzyme activity)
R=Additional Comments
gp=guinea pig; hum=human; syh=syrian hamster

Figure 34

| CAT. # | TARGET | BATCH* | SPP. | n= | CONC. | †% INHIBITION -100 -50 0 50 100 | IC$_{50}$ | K$_i$ | n$_H$ | R |
|---|---|---|---|---|---|---|---|---|---|---|
| 255510 | Tachykinin NK$_1$ | 92831 | hum | 2 | 10 µM | -10 | | | | |
| 285010 | Testosterone | 93005 | rat | 2 | 10 µM | 8 | | | | |
| 220320 | Transporter, Dopamine (DAT) | 92605 | hum | 2 | 10 µM | 9 | | | | |
| 226400 | Transporter, GABA | 92827 | rat | 2 | 10 µM | 0 | | | | |
| 204410 | Transporter, Norepinephrine (NET) | | | | | | | | | |
| ◆ | | 92606 | hum | 2 | 10 µM | 86 | | | | |
| ◆ | | 93798 | hum | 2 | 30 µM | 97 | 0.203 µM | 0.201 µM | 0.733 | |
| ◆ | | | | 2 | 10 µM | 94 | | | | |
| ◆ | | | | 2 | 3 µM | 90 | | | | |
| ◆ | | | | 2 | 1 µM | 77 | | | | |
| ◆ | | | | 2 | 0.3 µM | 55 | | | | |
| | | | | 2 | 0.1 µM | 39 | | | | |
| ◆ | | 94109 | hum | 2 | 3 µM | 84 | 0.237 µM | 0.235 µM | 0.706 | |
| ◆ | | | | 2 | 1 µM | 73 | | | | |
| ◆ | | | | 2 | 0.3 µM | 55 | | | | |
| | | | | 2 | 0.1 µM | 37 | | | | |
| | | | | 2 | 0.03 µM | 16 | | | | |
| ◆ | | 94317 | hum | 2 | 3 µM | 86 | 0.22 µM | 0.218 µM | 0.596 | |
| ◆ | | | | 2 | 1 µM | 71 | | | | |
| ◆ | | | | 2 | 0.3 µM | 51 | | | | |
| | | | | 2 | 0.1 µM | 38 | | | | |
| | | | | 2 | 0.03 µM | 26 | | | | |
| 274020 | Transporter, Serotonin (5-Hydroxytryptamine) (SERT) | | | | | | | | | |
| ◆ | | 92602 | hum | 2 | 10 µM | 99 | | | | |
| ◆ | | 93802 | hum | 2 | 1 µM | 96 | 0.0139 µM | 7.4 nM | 0.704 | |
| ◆ | | | | 2 | 0.3 µM | 87 | | | | |
| ◆ | | | | 2 | 0.1 µM | 85 | | | | |
| ◆ | | | | 2 | 0.03 µM | 63 | | | | |
| | | | | 2 | 10 nM | 38 | | | | |
| | | | | 2 | 3 nM | 30 | | | | |
| ◆ | | 94111 | hum | 2 | 0.1 µM | 89 | 0.0111 µM | 5.89 nM | 0.864 | |
| ◆ | | | | 2 | 0.03 µM | 70 | | | | |
| | | | | 2 | 10 nM | 48 | | | | |
| | | | | 2 | 3 nM | 21 | | | | |
| | | | | 2 | 1 nM | 17 | | | | |

*Batch: Represents compounds tested concurrently in the same assay(s).
◆ Denotes item meeting criteria for significance
†Results with ≥ 50% stimulation or inhibition are boldfaced. (Negative values correspond to <u>stimulation</u> of binding or enzyme activity)
R=Additional Comments
gp=guinea pig; hum=human; syh=syrian hamster

Figure 35

| CAT. # | TARGET | BATCH* | SPP. | n= | CONC. | †% INHIBITION -100 -50 0 50 100 % ↓ ↓ ↓ ↓ ↓ | IC$_{50}$ | K$_i$ | n$_H$ | R |
|---|---|---|---|---|---|---|---|---|---|---|
| 274020 ♦ ♦ | Transporter, Serotonin (5-Hydroxytryptamine) (SERT) | 94318 | hum | 2 2 2 2 2 | 0.1 µM 0.03 µM 10 nM 3 nM 1 nM | 88 69 42 18 15 | 0.013 µM | 6.91 nM | 0.906 | |

*Batch: Represents compounds tested concurrently in the same assay(s).
♦ Denotes item meeting criteria for significance
†Results with ≥ 50% stimulation or inhibition are boldfaced. (Negative values correspond to <u>stimulation</u> of binding or enzyme activity)
R=Additional Comments
gp=guinea pig; hum=human; syh=syrian hamster

Figure 36

| CAT. # | ASSAY NAME | REFERENCE COMPOUND | HISTORICAL IC$_{50}$ | HISTORICAL K$_i$ | n$_H$ | CONCURRENT MIC BATCH* | CONCURRENT MIC IC$_{50}$ |
|---|---|---|---|---|---|---|---|
| 118050 | CYP450, 1A2 | Furafylline | 0.96 µM | | | 93172 | 0.835 µM |
| 118070 | CYP450, 2C19 | Tranylcypromine | 8.1 µM | | | 93174 | 8.68 µM |
| 118060 | CYP450, 2C9 | Sulfaphenazole | 0.77 µM | | | 93173 | 0.453 µM |
| 118080 | CYP450, 2D6 | Quinidine | 0.057 µM | | | 93175 | 0.0368 µM |
| 118090 | CYP450, 3A4 | Ketoconazole | 0.22 µM | | | 92943 | 0.263 µM |
| 200510 | Adenosine A$_1$ | R(-)-PIA | 0.44 µM | 0.26 µM | 0.8 | 92728 | 0.549 µM |
| 200610 | Adenosine A$_{2A}$ | CGS-21680 | 0.46 µM | 0.26 µM | 0.9 | 92729 | 0.118 µM |
| 203100 | Adrenergic α$_{1A}$ | Prazosin | 0.69 nM | 0.28 nM | 0.9 | 92918 | 0.385 nM |
| 203200 | Adrenergic α$_{1B}$ | Prazosin | 0.27 nM | 0.15 nM | 1 | 92919 | 0.238 nM |
| 203400 | Adrenergic α$_{1D}$ | Prazosin | 0.88 nM | 0.43 nM | 0.7 | 92920 | 0.595 nM |
| 203620 | Adrenergic α$_{2A}$ | Yohimbine | 8.4 nM | 3.1 nM | 0.9 | 92621 | 3.35 nM |
| 203710 | Adrenergic α$_{2B}$ | Yohimbine | 0.014 µM | 6.4 nM | 1 | 92922 | 0.0341 µM |
| 204010 | Adrenergic β$_1$ | S(-)-Propranolol | 2.5 nM | 1.4 nM | 0.8 | 92731 | 1.91 nM |
| 204110 | Adrenergic β$_2$ | S(-)-Propranolol | 0.78 nM | 0.54 nM | 1.2 | 92732 | 0.448 nM |
| 212500 | Bradykinin B$_1$ | (Des-Arg$^{10}$)-Kallidin | 1.6 nM | 0.27 nM | 0.9 | 92644 | 2 nM |
| 212610 | Bradykinin B$_2$ | Bradykinin | 0.89 nM | 0.53 nM | 0.9 | 92828 | 0.897 nM |
| 214510 | Calcium Channel L-Type, Benzothiazepine | Diltiazem | 0.036 µM | 0.032 µM | 0.9 | 92613 | 0.0337 µM |
| 214600 | Calcium Channel L-Type, Dihydropyridine | Nitrendipine | 0.72 nM | 0.46 nM | 0.9 | 92614 | 1.31 nM |
| 216000 | Calcium Channel N-Type | ω-Conotoxin GVIA | 0.034 nM | 0.028 nM | 1.6 | 92708 | 0.0117 nM |
| 219500 | Dopamine D$_1$ | R(+)-SCH-23390 | 1.4 nM | 0.7 nM | 0.9 | 92810 | 1.48 nM |
| 219600 | Dopamine D$_{2L}$ | Spiperone | 0.58 nM | 0.19 nM | 1.2 | 92811 | 0.356 nM |
| 219800 | Dopamine D$_3$ | Spiperone | 0.36 nM | 0.12 nM | 0.9 | 92813 | 0.73 nM |
| 219900 | Dopamine D$_{4.2}$ | Spiperone | 0.98 nM | 0.34 nM | 1 | 92814 | 1.87 nM |
| 224010 | Endothelin ET$_A$ | Endothelin-1 | 0.23 nM | 0.14 nM | 1.1 | 92735 | 0.327 nM |
| 224110 | Endothelin ET$_B$ | Endothelin-1 | 0.13 nM | 0.06 nM | 0.9 | 92736 | 0.0785 nM |
| 225500 | Epidermal Growth Factor (EGF) | Epidermal Growth Factor (EGF) (human) | 0.39 nM | 0.15 nM | 1.2 | 92641 | 0.169 nM |
| 226010 | Estrogen ERα | Diethylstilbestrol | 1.1 nM | 0.31 nM | 1.1 | 92633 | 0.52 nM |
| 226500 | GABA$_A$, Agonist Site | GABA | 0.08 µM | 0.063 µM | 0.8 | 92616 | 0.0641 µM |
| 226600 | GABA$_A$, Benzodiazepine, Central | Diazepam | 0.016 µM | 0.013 µM | 0.8 | 92830 | 0.011 µM |
| 228510 | GABA$_B$, Non-Selective | CGP-54626 | 1.8 nM | 1.4 nM | 1 | 92715 | 1.96 nM |
| 232010 | Glucocorticoid | Dexamethasone | 0.041 µM | 0.019 µM | 0.9 | 92894 | 9.03 nM |
| 232700 | Glutamate, Kainate | L-Glutamate | 0.24 µM | 0.17 µM | 0.8 | 92635 | 0.272 µM |
| 232810 | Glutamate, NMDA, Agonism | L-Glutamate | 0.41 µM | 0.37 µM | 0.9 | 92720 | 0.303 µM |
| 232910 | Glutamate, NMDA, Glycine | MDL-105519 | 0.022 µM | 0.021 µM | 0.6 | 92912 | 5.28 nM |
| 233000 | Glutamate, NMDA, Phencyclidine | Dizolcipine (MK-801) | 5.1 nM | 3.4 nM | 0.7 | 92636 | 5.42 nM |

*Batch: Represents compounds tested concurrently in the same assay(s).

Figure 37

| CAT. # | ASSAY NAME | REFERENCE COMPOUND | HISTORICAL IC$_{50}$ | K$_i$ | n$_H$ | CONCURRENT MIC BATCH* | IC$_{50}$ |
|---|---|---|---|---|---|---|---|
| 239610 | Histamine H$_1$ | Pyrilamine | 3.3 nM | 1.6 nM | 1 | 92617 | 3.32 nM |
| 239710 | Histamine H$_2$ | Tiotidine | 0.022 μM | 0.018 μM | 1.1 | 92618 | 0.028 μM |
| 239810 | Histamine H$_3$ | R(-)-α-Methylhistamine (RAMH) | 5.2 nM | 2.3 nM | 0.9 | 92853 | 4.6 nM |
| 241000 | Imidazoline I$_2$, Central | Idazoxan | 0.012 μM | 8 nM | 1 | 92836 | 6.93 nM |
| 243510 | Interleukin IL-1, Non-Selective | Interleukin-1α (IL-1α) | 0.027 nM | 10 pM | 1 | 92929 | 0.0417 nM |
| 250600 | Leukotriene LTD$_4$ | Leukotriene D$_4$ (LTD$_4$) | 1.4 nM | 0.7 nM | 1 | 92643 | 0.731 nM |
| 252600 | Muscarinic M$_1$ | 4-DAMP | 4.3 nM | 1 nM | 1 | 92840 | 3.82 nM |
| 252700 | Muscarinic M$_2$ | 4-DAMP | 0.013 μM | 4.6 nM | 0.9 | 92841 | 0.0219 μM |
| 252800 | Muscarinic M$_3$ | 4-DAMP | 3.9 nM | 0.83 nM | 1 | 92842 | 3.21 nM |
| 257000 | Neuropeptide Y$_1$ | Neuropeptide Y (human, rat) | 4 nM | 3.9 nM | 1 | 92820 | 1.06 nM |
| 257110 | Neuropeptide Y$_2$ | Neuropeptide Y (13-36) (porcine) | 4.4 nM | 2.4 nM | 0.7 | 92821 | 2.28 nM |
| 258590 | Nicotinic Acetylcholine | (+)-Epibatidine | 0.071 nM | 0.049 μM | 0.9 | 92737 | 0.0545 nM |
| 260110 | Opiate δ (OP1, DOP) | Naltrindole | 0.92 nM | 0.32 nM | 1 | 92824 | 0.85 nM |
| 260210 | Opiate κ (OP2, KOP) | U-69593 | 0.016 μM | 6.4 nM | 0.5 | 92823 | 7.68 nM |
| 260410 | Opiate μ (OP3, MOP) | DAMGO | 0.02 μM | 8.1 nM | 0.6 | 92822 | 0.011 μM |
| 264500 | Phorbol Ester | PMA | 9.1 nM | 6.8 nM | 1.1 | 92834 | 9.95 nM |
| 265010 | Platelet Activating Factor (PAF) | PAF | 0.28 nM | 0.15 nM | 0.9 | 92835 | 0.548 nM |
| 265600 | Potassium Channel [K$_{ATP}$] | Glyburide | 0.018 μM | 2 nM | 0.8 | 92637 | 8.04 nM |
| 268700 | Purinergic P$_{2X}$ | α, β-Methylene ATP | 0.082 μM | 0.018 μM | 1.1 | 92638 | 0.0764 μM |
| 268810 | Purinergic P$_{2Y}$ | ATP | 0.018 μM | 0.018 μM | 0.9 | 92649 | 0.038 μM |
| 271110 | Serotonin (5-Hydroxytryptamine) 5-HT$_{1A}$ | Metergoline | 4.1 nM | 2.3 nM | 0.9 | 92716 | 6.6 nM |
| 271910 | Serotonin (5-Hydroxytryptamine) 5-HT$_3$ | MDL-72222 | 0.011 μM | 2.5 nM | 0.8 | 92629 | 0.0157 μM |
| 278110 | Sigma σ$_1$ | Haloperidol | 0.021 μM | 8.8 nM | 0.9 | 92925 | 7.67 nM |
| 278200 | Sigma σ$_2$ | Ifenprodil | 8 nM | 4.9 nM | 0.7 | 92926 | 3.55 nM |
| 279450 | Sodium Channel, Site 1 | Saxitoxin | 1.7 nM | 0.7 nM | 1 | 92838 | 2.31 nM |
| 279510 | Sodium Channel, Site 2 | Dibucaine | 0.61 μM | 0.55 μM | 0.9 | 92619 | 0.892 μM |
| 255510 | Tachykinin NK$_1$ | L-703,606 | 0.025 μM | 0.014 μM | 0.8 | 92831 | 0.0217 μM |
| 285010 | Testosterone | Testosterone | 6.5 nM | 4.3 nM | 1 | 93005 | 6.37 nM |
| 220320 | Transporter, Dopamine (DAT) | GBR-12909 | 1.7 nM | 1.3 nM | 0.9 | 92605 | 0.692 nM |
| 226400 | Transporter, GABA | NO-711 | 0.2 μM | 0.2 μM | 1.1 | 92827 | 0.214 μM |
| 204410 | Transporter, Norepinephrine (NET) | Desipramine | 0.93 nM | 0.92 nM | 0.6 | 92606 | 0.83 nM |
|  |  | Desipramine | 0.93 nM | 0.92 nM | 0.6 | 93798 | 2.06 nM |

*Batch: Represents compounds tested concurrently in the same assay(s).

Figure 38

| CAT. # | ASSAY NAME | REFERENCE COMPOUND | HISTORICAL | | | CONCURRENT MIC | |
|---|---|---|---|---|---|---|---|
| | | | $IC_{50}$ | $K_i$ | $n_H$ | BATCH* | $IC_{50}$ |
| 204410 | Transporter, Norepinephrine (NET) | Desipramine | 0.93 nM | 0.92 nM | 0.6 | 94109 | 2.13 nM |
| | | Desipramine | 0.93 nM | 0.92 nM | 0.6 | 94317 | 1.96 nM |
| 274020 | Transporter, Serotonin (5-Hydroxytryptamine) (SERT) | GBR-12909 | 0.11 µM | 0.057 µM | 0.8 | 92602 | 0.0667 µM |
| | | GBR-12909 | 0.11 µM | 0.057 µM | 0.8 | 93802 | 0.0941 µM |
| | | GBR-12909 | 0.11 µM | 0.057 µM | 0.8 | 94111 | 0.0671 µM |
| | | GBR-12909 | 0.11 µM | 0.057 µM | 0.8 | 94318 | 0.103 µM |

*Batch: Represents compounds tested concurrently in the same assay(s).

| Compound | IC$_{50}$ | K$_i$ | n$_H$ |
|---|---|---|---|
| ● Vial #1 (1036183) | 0.22 ± 0.01 μM | 0.218 ± 0.01 μM | 0.678 ± 0.042 |
| ■ Desipramine | 2.05 ± 0.049 nM | 2.03 ± 0.048 nM | 0.694 ± 0.036 |

| Compound | IC$_{50}$ | K$_I$ | n$_H$ |
|---|---|---|---|
| Vial #1 (1036183) | 0.0127 ± 0.001 µM | 6.73 ± 0.442 nM | 0.825 ± 0.0616 |
| ■ GBR-12909 | 0.088 ± 0.0107 µM | 0.0467 ± 0.006 µM | 1.17 ± 0.088 |

Figure 41

| COMPOUND CODE | PT NUMBER | BATCH* | SPP. | n= | CONC. | †% INHIBITION % | IC₅₀ | Kᵢ | nₕ | R |
|---|---|---|---|---|---|---|---|---|---|---|
| 212610 Bradykinin B₂ | | | | | | | | | | |
| Vial # 2 | 1037044 | 94766 | hum | 2 | 10 μM | -15 | | | | |
| Vial # 3 | 1037045 | 94766 | hum | 2 | 10 μM | -2 | | | | |
| 118090 CYP450, 3A4 | | | | | | | | | | |
| Vial # 2 | 1037044 | 95160 | hum | 2 | 10 μM | 24 | | | | |
| Vial # 3 | 1037045 | 95160 | hum | 2 | 10 μM | 39 | | | | |
| 214510 Calcium Channel L-Type, Benzothiazepine | | | | | | | | | | |
| Vial # 2 | 1037044 | 94767 | rat | 2 | 10 μM | 26 | | | | |
| Vial # 3 | 1037045 | 94767 | rat | 2 | 10 μM | 34 | | | | |
| 204410 Transporter; Norepinephrine (NET) | | | | | | | | | | |
| ♦ Vial # 2 | 1037044 | 94760 | hum | 2 | 10 μM | 92 | | | | |
| ♦ | | 95109 | hum | 2 | 3 μM | 85 | 0.0978 μM | 0.097 μM | 0.62 | |
| ♦ | | | | 2 | 1 μM | 82 | | | | |
| ♦ | | | | 2 | 0.3 μM | 63 | | | | |
| ♦ | | | | 2 | 0.1 μM | 59 | | | | |
| | | | | 2 | 0.03 μM | 30 | | | | |
| | | | | 2 | 10 nM | 16 | | | | |
| ♦ | | 95324 | hum | 2 | 3 μM | 86 | 0.101 μM | 0.1 μM | 0.493 | |
| ♦ | | | | 2 | 1 μM | 74 | | | | |
| ♦ | | | | 2 | 0.3 μM | 63 | | | | |
| ♦ | | | | 2 | 0.1 μM | 51 | | | | |
| | | | | 2 | 0.03 μM | 35 | | | | |
| ♦ | | 95371 | hum | 2 | 3 μM | 84 | 0.138 μM | 0.136 μM | 0.64 | |
| ♦ | | | | 2 | 1 μM | 77 | | | | |
| ♦ | | | | 2 | 0.3 μM | 66 | | | | |
| | | | | 2 | 0.1 μM | 47 | | | | |
| | | | | 2 | 0.03 μM | 23 | | | | |
| ♦ Vial # 3 | 1037045 | 94760 | hum | 2 | 10 μM | 84 | | | | |
| ♦ | | 94891 | hum | 2 | 30 μM | 87 | 1.67 μM | 1.65 μM | 0.745 | |
| ♦ | | | | 2 | 10 μM | 78 | | | | |

\* Batch: Represents compounds tested concurrently in the same assay(s). ‡ Partially soluble in *in vitro* test solvent.
♦ Denotes item meeting criteria for significance
† Results with ≥ 50% stimulation or inhibition are highlighted. (Negative values correspond to <u>stimulation</u> of binding or enzyme activity)
R=Additional Comments
hum=human

Figure 42

| COMPOUND CODE | PT NUMBER | BATCH* | SPP. | n= | CONC. | †% INHIBITION % | IC$_{50}$ | K$_i$ | n$_H$ | R |
|---|---|---|---|---|---|---|---|---|---|---|
| 204410 Transporter, Norepinephrine (NET) | | | | | | | | | | |
| ♦ Vial # 3 | 1037045 | 94891 | hum | 2 | 3 µM | 61 | 1.67 µM | 1.65 µM | 0.745 | |
| | | | | 2 | 1 µM | 46 | | | | |
| | | | | 2 | 0.3 µM | 18 | | | | |
| | | | | 2 | 0.1 µM | 9 | | | | |
| ♦ | | 95109 | hum | 2 | 30 µM | 93 | 1.43 µM | 1.42 µM | 0.77 | |
| ♦ | | | | 2 | 10 µM | 77 | | | | |
| ♦ | | | | 2 | 3 µM | 66 | | | | |
| | | | | 2 | 1 µM | 45 | | | | |
| | | | | 2 | 0.3 µM | 21 | | | | |
| ♦ | | 95324 | hum | 2 | 30 µM | 78 | 1.95 µM | 1.93 µM | 0.523 | |
| ♦ | | | | 2 | 10 µM | 72 | | | | |
| ♦ | | | | 2 | 3 µM | 57 | | | | |
| | | | | 2 | 1 µM | 40 | | | | |
| | | | | 2 | 0.3 µM | 27 | | | | |
| 274020 Transporter, Serotonin (5-Hydroxytryptamine) (SERT) | | | | | | | | | | |
| ♦ Vial # 2 | 1037044 | 94762 | hum | 2 | 10 µM | 98 | | | | |
| ♦ | | 95110 | hum | 2 | 0.3 µM | 95 | 7.17 nM | 3.81 nM | 0.999 | |
| ♦ | | | | 2 | 0.1 µM | 93 | | | | |
| ♦ | | | | 2 | 0.03 µM | 80 | | | | |
| ♦ | | | | 2 | 10 nM | 59 | | | | |
| | | | | 2 | 3 nM | 31 | | | | |
| | | | | 2 | 1 nM | 10 | | | | |
| ♦ | | 95326 | hum | 2 | 0.1 µM | 88 | 8.68 nM | 4.61 nM | 0.906 | |
| ♦ | | | | 2 | 0.03 µM | 77 | | | | |
| ♦ | | | | 2 | 10 nM | 53 | | | | |
| | | | | 2 | 3 nM | 28 | | | | |
| | | | | 2 | 1 nM | 11 | | | | |
| ♦ | | 95372 | hum | 2 | 0.1 µM | 92 | 6.03 nM | 3.2 nM | 0.942 | |
| ♦ | | | | 2 | 0.03 µM | 82 | | | | |
| ♦ | | | | 2 | 10 nM | 62 | | | | |

* Batch: Represents compounds tested concurrently in the same assay(s). ‡ Partially soluble in *in vitro* test solvent.
♦ Denotes item meeting criteria for significance
† Results with ≥ 50% stimulation or inhibition are highlighted. (Negative values correspond to <u>stimulation</u> of binding or enzyme activity)
R=Additional Comments
hum=human

Figure 43

| COMPOUND CODE | PT NUMBER | BATCH* | SPP. | n= | CONC. | †% INHIBITION % | $IC_{50}$ | $K_i$ | $n_H$ | R |
|---|---|---|---|---|---|---|---|---|---|---|
| 274020 Transporter, Serotonin (5-Hydroxytryptamine) (SERT) | | | | | | | | | | |
| Vial # 2 | 1037044 | 95372 | hum | 2 | 3 nM | 35 | 6.03 nM | 3.2 nM | 0.942 | |
| | | | | 2 | 1 nM | 14 | | | | |
| ♦ Vial # 3 | 1037045 | 94762 | hum | 2 | 10 µM | 100 | | | | |
| ♦ | | 95110 | hum | 2 | 1 µM | 96 | 0.014 µM | 7.45 nM | 0.907 | |
| ♦ | | | | 2 | 0.3 µM | 93 | | | | |
| ♦ | | | | 2 | 0.1 µM | 84 | | | | |
| ♦ | | | | 2 | 0.03 µM | 67 | | | | |
| | | | | 2 | 10 nM | 44 | | | | |
| | | | | 2 | 3 nM | 17 | | | | |
| ♦ | | 95326 | hum | 2 | 0.3 µM | 91 | 0.0197 µM | 0.0105 µM | 0.869 | |
| ♦ | | | | 2 | 0.1 µM | 81 | | | | |
| ♦ | | | | 2 | 0.03 µM | 59 | | | | |
| | | | | 2 | 10 nM | 36 | | | | |
| | | | | 2 | 3 nM | 16 | | | | |
| ♦ | | 95372 | hum | 2 | 0.3 µM | 97 | 0.0123 µM | 6.52 nM | 1.05 | |
| ♦ | | | | 2 | 0.1 µM | 89 | | | | |
| ♦ | | | | 2 | 0.03 µM | 72 | | | | |
| | | | | 2 | 10 nM | 45 | | | | |
| | | | | 2 | 3 nM | 18 | | | | |

* Batch: Represents compounds tested concurrently in the same assay(s). ‡ Partially soluble in *in vitro* test solvent.
♦ Denotes item meeting criteria for significance
† Results with ≥ 50% stimulation or inhibition are highlighted. (Negative values correspond to stimulation of binding or enzyme activity)
R=Additional Comments
hum=human

Figure 44

| | | | CELLULAR ASSAYS | | | | %RESPONSE | | | |
|---|---|---|---|---|---|---|---|---|---|---|
| COMPOUND CODE | PT NUMBER | BATCH* | TISSUE, SPECIES | n= | CONC. | CRITERIA | RESP. | AG. | ANT. | R |
| 302100 Cytotoxicity, Norepinephrine Uptake | | | | | | | | | | |
| Vial #1 | 1036183 | 95055 | MDCK cells, hum | 2 | 10 µM | ≥ ± 50% | | | | 9 |
| Vial #1 | 1036183 | 95055 | MDCK cells, hum | 2 | 1 µM | ≥ ± 50% | | | | 8 |
| | | | MDCK cells, hum | 2 | 0.1 µM | ≥ ± 50% | | | | -4 |
| | | | MDCK cells, hum | 2 | 10 nM | ≥ ± 50% | | | | 0 |
| | | | MDCK cells, hum | 2 | 1 nM | ≥ ± 50% | | | | -8 |
| Vial # 2 | 1037044 | 95055 | MDCK cells, hum | 2 | 10 µM | ≥ ± 50% | | | | 11 |
| | | | MDCK cells, hum | 2 | 1 µM | ≥ ± 50% | | | | 14 |
| | | | MDCK cells, hum | 2 | 0.1 µM | ≥ ± 50% | | | | 7 |
| | | | MDCK cells, hum | 2 | 10 nM | ≥ ± 50% | | | | 9 |
| | | | MDCK cells, hum | 2 | 1 nM | ≥ ± 50% | | | | 0 |
| Vial # 3 | 1037045 | 95055 | MDCK cells, hum | 2 | 10 µM | ≥ ± 50% | | | | -6 |
| | | | MDCK cells, hum | 2 | 1 µM | ≥ ± 50% | | | | -1 |
| | | | MDCK cells, hum | 2 | 0.1 µM | ≥ ± 50% | | | | -6 |
| | | | MDCK cells, hum | 2 | 10 nM | ≥ ± 50% | | | | -6 |
| | | | MDCK cells, hum | 2 | 1 nM | ≥ ± 50% | | | | -3 |
| 364100 Cytotoxicity, Serotonin (5-Hydroxytryptamine) Uptake | | | | | | | | | | |
| Vial #1 | 1036183 | 95056 | HEK-293 cells, hum | 2 | 10 µM | ≥ ± 50% | | | | 2 |
| | | | HEK-293 cells, hum | 2 | 1 µM | ≥ ± 50% | | | | -7 |
| | | | HEK-293 cells, hum | 2 | 0.1 µM | ≥ ± 50% | | | | 0 |
| | | | HEK-293 cells, hum | 2 | 10 nM | ≥ ± 50% | | | | -2 |
| | | | HEK-293 cells, hum | 2 | 1 nM | ≥ ± 50% | | | | -3 |
| Vial # 2 | 1037044 | 95056 | HEK-293 cells, hum | 2 | 10 µM | ≥ ± 50% | | | | -8 |
| | | | HEK-293 cells, hum | 2 | 1 µM | ≥ ± 50% | | | | -7 |
| | | | HEK-293 cells, hum | 2 | 0.1 µM | ≥ ± 50% | | | | -2 |
| | | | HEK-293 cells, hum | 2 | 10 nM | ≥ ± 50% | | | | 0 |
| | | | HEK-293 cells, hum | 2 | 1 nM | ≥ ± 50% | | | | 2 |
| Vial # 3 | 1037045 | 95056 | HEK-293 cells, hum | 2 | 10 µM | ≥ ± 50% | | | | -3 |
| | | | HEK-293 cells, hum | 2 | 1 µM | ≥ ± 50% | | | | -6 |
| | | | HEK-293 cells, hum | 2 | 0.1 µM | ≥ ± 50% | | | | -6 |

\* Batch: Represents compounds tested concurrently in the same assay(s). ‡ Partially soluble in *in vitro* test solvent.
♦ Denotes item meeting criteria for significance
Ag.=Agonist; Ant.=Antagonist; Resp.=Response; ND=Assay Test Not Done; R=Additional Comments
hum=human

Figure 45

| | | | CELLULAR ASSAYS | | | | %RESPONSE | | |
|---|---|---|---|---|---|---|---|---|---|
| COMPOUND CODE | PT NUMBER | BATCH* | TISSUE, SPECIES | n= | CONC. | CRITERIA RESP. | AG. | ANT. | R |
| 364100 Cytotoxicity, Serotonin (5-Hydroxytryptamine) Uptake | | | | | | | | | |
| Vial # 3 | 1037045 | 95056 | HEK-293 cells, hum | 2 | 10 nM | ≥ ± 50% | | -4 | |
| | | | HEK-293 cells, hum | 2 | 1 nM | ≥ ± 50% | | -1 | |
| 302000 Uptake, Norepinephrine | | | | | | | | | |
| ♦ Vial #1 | 1036183 | 94864 | MDCK cells, hum | 2 | 10 µM | ≥ ± 50% | | 95 | |
| ♦ | | | MDCK cells, hum | 2 | 1 µM | ≥ ± 50% | | 95 | |
| ♦ | | | MDCK cells, hum | 2 | 0.1 µM | ≥ ± 50% | | 78 | |
| | | | MDCK cells, hum | 2 | 10 nM | ≥ ± 50% | | 25 | |
| | | | MDCK cells, hum | 2 | 1 nM | ≥ ± 50% | | 7 | |
| ♦ Vial # 2 | 1037044 | 94864 | MDCK cells, hum | 2 | 10 µM | ≥ ± 50% | | 99 | |
| ♦ | | | MDCK cells, hum | 2 | 1 µM | ≥ ± 50% | | 98 | |
| ♦ | | | MDCK cells, hum | 2 | 0.1 µM | ≥ ± 50% | | 90 | |
| ♦ | | | MDCK cells, hum | 2 | 10 nM | ≥ ± 50% | | 50 | |
| | | | MDCK cells, hum | 2 | 1 nM | ≥ ± 50% | | 5 | |
| ♦ Vial # 3 | 1037045 | 94864 | MDCK cells, hum | 2 | 10 µM | ≥ ± 50% | | 97 | |
| ♦ | | | MDCK cells, hum | 2 | 1 µM | ≥ ± 50% | | 83 | |
| | | | MDCK cells, hum | 2 | 0.1 µM | ≥ ± 50% | | 48 | |
| | | | MDCK cells, hum | 2 | 10 nM | ≥ ± 50% | | 20 | |
| | | | MDCK cells, hum | 2 | 1 nM | ≥ ± 50% | | 15 | |
| 364000 Uptake, Serotonin (5-Hydroxytryptamine) | | | | | | | | | |
| ♦ Vial #1 | 1036183 | 94865 | HEK-293 cells, hum | 2 | 10 µM | ≥ ± 50% | | 100 | |
| ♦ | | | HEK-293 cells, hum | 2 | 1 µM | ≥ ± 50% | | 94 | |
| ♦ | | | HEK-293 cells, hum | 2 | 0.1 µM | ≥ ± 50% | | 75 | |
| | | | HEK-293 cells, hum | 2 | 10 nM | ≥ ± 50% | | 38 | |
| | | | HEK-293 cells, hum | 2 | 1 nM | ≥ ± 50% | | 4 | |
| ♦ Vial # 2 | 1037044 | 94865 | HEK-293 cells, hum | 2 | 10 µM | ≥ ± 50% | | 99 | |
| ♦ | | | HEK-293 cells, hum | 2 | 1 µM | ≥ ± 50% | | 96 | |
| ♦ | | | HEK-293 cells, hum | 2 | 0.1 µM | ≥ ± 50% | | 80 | |
| | | | HEK-293 cells, hum | 2 | 10 nM | ≥ ± 50% | | 33 | |
| | | | HEK-293 cells, hum | 2 | 1 nM | ≥ ± 50% | | 5 | |

* Batch: Represents compounds tested concurrently in the same assay(s). ‡ Partially soluble in *in vitro* test solvent.
♦ Denotes item meeting criteria for significance
Ag.=Agonist; Ant.=Antagonist; Resp.=Response; ND=Assay Test Not Done; R=Additional Comments
hum=human

Figure 46

| | | | CELLULAR ASSAYS | | | | %RESPONSE | | |
|---|---|---|---|---|---|---|---|---|---|
| COMPOUND CODE | PT NUMBER | BATCH* | TISSUE, SPECIES | n= | CONC. | CRITERIA RESP. | AG. | ANT. | R |
| 364000 Uptake, Serotonin (5-Hydroxytryptamine) | | | | | | | | | |
| ♦ Vial # 3 | 1037045 | 94865 | HEK-293 cells, hum | 2 | 10 µM | ≥ ± 50% | | 100 | |
| ♦ | | | HEK-293 cells, hum | 2 | 1 µM | ≥ ± 50% | | 88 | |
| ♦ | | | HEK-293 cells, hum | 2 | 0.1 µM | ≥ ± 50% | | 65 | |
| | | | HEK-293 cells, hum | 2 | 10 nM | ≥ ± 50% | | 33 | |
| | | | HEK-293 cells, hum | 2 | 1 nM | ≥ ± 50% | | -4 | |

* Batch: Represents compounds tested concurrently in the same assay(s). ‡ Partially soluble in *in vitro* test solvent.
♦ Denotes item meeting criteria for significance
Ag.=Agonist; Ant.=Antagonist; Resp.=Response; ND=Assay Test Not Done; R=Additional Comments
hum=human

| Compound | IC$_{50}$ | n$_H$ |
|---|---|---|
| CEL - 1 (1036183) | 0.0286 µM | 0.94 |
| ■ Desipramine | 0.922 nM | 0.78 |

| Compound | IC$_{50}$ | n$_H$ |
|---|---|---|
| CEL - 1 (1036183) | 0.0217 µM | 0.766 |
| ■ Fluoxetine | 4.36 nM | 0.943 |

| Compound | IC$_{50}$ | K$_i$ | n$_H$ |
|---|---|---|---|
| CEL - 3 (1037044) | 0.112 ± 0.013 µM | 0.111 ± 0.013 µM | 0.584 ± 0.046 |
| ■ Desipramine | 2.78 ± 0.498 nM | 2.76 ± 0.494 nM | 0.872 ± 0.008 |

| Compound | IC$_{50}$ | K$_i$ | n$_H$ |
|---|---|---|---|
| ● CEL - 3 (1037044) | 7.3 ± 0.768 nM | 3.88 ± 0.408 nM | 0.949 ± 0.027 |
| ■ GBR-12909 | 0.0675 ± 0.0105 µM | 0.0359 ± 0.006 µM | 1.01 ± 0.105 |

| Compound | IC$_{50}$ | n$_H$ |
|---|---|---|
| CEL - 3 (1037044) | 0.0103 µM | 1.08 |
| ■ Desipramine | 0.922 nM | 0.78 |

| Compound | IC$_{50}$ | n$_H$ |
|---|---|---|
| CEL - 3 (1037044) | 0.022 µM | 0.909 |
| ■ Fluoxetine | 4.36 nM | 0.943 |

| Compound | IC$_{50}$ | K$_i$ | n$_H$ |
|---|---|---|---|
| CEL - 5 (1037045) | 1.68 ± 0.149 µM | 1.67 ± 0.148 µM | 0.679 ± 0.078 |
| ■ Desipramine | 2.52 ± 0.292 nM | 2.5 ± 0.289 nM | 0.882 ± 0.016 |

| Compound | IC$_{50}$ | K$_i$ | n$_H$ |
|---|---|---|---|
| CEL - 5 (1037045) | 0.0153 ± 0.002 µM | 8.15 ± 1.19 nM | 0.94 ± 0.054 |
| ■ GBR-12909 | 0.0675 ± 0.0105 µM | 0.0359 ± 0.006 µM | 1.01 ± 0.105 |

| Compound | IC$_{50}$ | n$_H$ |
|---|---|---|
| CEL - 5 (1037045) | 0.0885 µM | 0.592 |
| ■ Desipramine | 0.922 nM | 0.78 |

| Compound | IC$_{50}$ | n$_H$ |
|---|---|---|
| CEL - 5 (1037045) | 0.0403 µM | 0.718 |
| ■ Fluoxetine | 4.36 nM | 0.943 |

Figure 57

| CAT. # | ASSAY NAME | REFERENCE COMPOUND | HISTORICAL IC$_{50}$/EC$_{50}$ | CONCURRENT MIC BATCH * | IC$_{50}$/EC$_{50}$ |
|---|---|---|---|---|---|
| 302100 | Cytotoxicity, Norepinephrine Uptake - Antagonist | DMSO | 29 % | 95055 | 19.9 % |
| 364100 | Cytotoxicity, Serotonin Uptake - Antagonist | DMSO | 20 % | 95056 | 27.5 % |
| 302000 | Uptake, Norepinephrine | Desipramine | 1.9 nM | 94864 | 0.922 nM |
| 364000 | Uptake, Serotonin | Fluoxetine | 7.1 nM | 94865 | 4.36 nM |

Figure 58

| CAT. # | ASSAY NAME | REFERENCE COMPOUND | HISTORICAL | | | CONCURRENT MIC | |
|---|---|---|---|---|---|---|---|
| | | | IC$_{50}$ | K$_i$ | n$_H$ | BATCH * | IC$_{50}$ |
| 118090 | CYP450, 3A4 | Ketoconazole | 0.22 µM | | | 95160 | 0.355 µM |
| 212610 | Bradykinin B$_2$ | Bradykinin | 0.89 nM | 0.53 nM | 0.9 | 94766 | 1.66 nM |
| 214510 | Calcium Channel L-Type, Benzothiazepine | Diltiazem | 0.036 µM | 0.032 µM | 0.9 | 94767 | 0.0873 µM |
| 204410 | Transporter, Norepinephrine (NET) | Desipramine | 0.93 nM | 0.92 nM | 0.6 | 94760 | 0.767 nM |
| | | Desipramine | 0.93 nM | 0.92 nM | 0.6 | 94891 | 2.89 nM |
| | | Desipramine | 0.93 nM | 0.92 nM | 0.6 | 95109 | 1.94 nM |
| | | Desipramine | 0.93 nM | 0.92 nM | 0.6 | 95324 | 2.73 nM |
| | | Desipramine | 0.93 nM | 0.92 nM | 0.6 | 95371 | 3.67 nM |
| 274020 | Transporter, Serotonin (5-Hydroxytryptamine) (SERT) | GBR-12909 | 0.11 µM | 0.057 µM | 0.8 | 94762 | 0.0707 µM |
| | | GBR-12909 | 0.11 µM | 0.057 µM | 0.8 | 95110 | 0.0871 µM |
| | | GBR-12909 | 0.11 µM | 0.057 µM | 0.8 | 95326 | 0.0644 µM |
| | | GBR-12909 | 0.11 µM | 0.057 µM | 0.8 | 95372 | 0.0512 µM |

Figure 59

PRIMARY TESTS

| CAT. # | PRIMARY BIOCHEMICAL ASSAY | SPECIES | CONC. | % INH. | IC$_{50}$* | K$_i$ | n$_H$ |
|---|---|---|---|---|---|---|---|
| 204410 | Transporter, Norepinephrine (NET) | hum | 0.3 µM | 51 | 0.22 ± 0.01 µM | 0.218 ± 0.01 µM | 0.678 ± 0.042 |
| 274020 | Transporter, Serotonin (5-Hydroxytryptamine) (SERT) | hum | 0.03 µM | 63 | 0.0127 ± 0.001 µM | 6.73 ± 0.442 nM | 0.825 ± 0.0616 |

ABOVE PRIMARY TESTS IN RANK ORDER OF POTENCY

| CAT. # | PRIMARY RADIOLIGAND ASSAY | SPECIES | CONC. | % INH. | IC$_{50}$* | K$_i$ | n$_H$ |
|---|---|---|---|---|---|---|---|
| 274020 | Transporter, Serotonin (5-Hydroxytryptamine) (SERT) | hum | 0.03 µM | 63 | 0.0127 ± 0.001 µM | 6.73 ± 0.442 nM | 0.825 ± 0.0616 |
| 204410 | Transporter, Norepinephrine (NET) | hum | 0.3 µM | 51 | 0.22 ± 0.01 µM | 0.218 ± 0.01 µM | 0.678 ± 0.042 |

Figure 60

| | | | PRIMARY TESTS | | | | | |
|---|---|---|---|---|---|---|---|---|
| | | | PRIMARY BIOCHEMICAL ASSAY | | | | | |
| | COMPOUND | PT NUMBER | SPECIES | CONC. | % INH. | $IC_{50}$ * | $K_i$ | $n_H$ |
| 204410 | Transporter, Norepinephrine (NET) | | | | | | | |
| | Vial # 2 | 1037044 | hum | 0.1 µM | 51 | 0.112 ± 0.013 µM | 0.111 ± 0.0126 | 0.584 ± 0.046 |
| | Vial # 3 | 1037045 | hum | 3 µM | 57 | 1.68 ± 0.149 µM | 1.67 ± 0.148 µM | 0.679 ± 0.078 |
| 274020 | Transporter, Serotonin (5-Hydroxytryptamine) (SERT) | | | | | | | |
| | Vial # 2 | 1037044 | hum | 10 nM | 53 | 7.3 ± 0.768 nM | 3.88 ± 0.408 nM | 0.949 ± 0.0269 |
| | Vial # 3 | 1037045 | hum | 0.03 µM | 59 | 0.0153 ± 0.002 µM | 8.15 ± 1.19 nM | 0.94 ± 0.054 |

Figure 61

| | | PRIMARY TESTS | | | | | | | | |
|---|---|---|---|---|---|---|---|---|---|---|
| | | PRIMARY CELLULAR ASSAY | | | | % RESPONSE | | | | |
| COMPOUND | PT NUMBER | SPECIES | CELL NAME | CONC. | CRITERIA | RESP. | AG. | ANT. | $EC_{50}/IC_{50}$ | * |
| 302000 Uptake, Norepinephrine | | | | | | | | | | |
| Vial #1 | 1036183 | hum | MDCK cells | 0.1 µM | ≥ ± 50% | | | 78 | 0.0286 µM | |
| Vial # 2 | 1037044 | hum | MDCK cells | 10 nM | ≥ ± 50% | | | 50 | 0.0103 µM | |
| Vial # 3 | 1037045 | hum | MDCK cells | 1 µM | ≥ ± 50% | | | 83 | 0.0885 µM | |
| 364000 Uptake, Serotonin (5-Hydroxytryptamine) | | | | | | | | | | |
| Vial #1 | 1036183 | hum | HEK-293 cells | 0.1 µM | ≥ ± 50% | | | 75 | 0.0217 µM | |
| Vial # 2 | 1037044 | hum | HEK-293 cells | 0.1 µM | ≥ ± 50% | | | 80 | 0.022 µM | |
| Vial # 3 | 1037045 | hum | HEK-293 cells | 0.1 µM | ≥ ± 50% | | | 65 | 0.0403 µM | |

Figure 62

| | | SECONDARY CELLULAR ASSAY | | | | % RESPONSE | | | |
|---|---|---|---|---|---|---|---|---|---|
| COMPOUND | PT NUMBER | SPECIES | CELL NAME | CONC. | CRITERIA | RESP. | AG | ANT. | $EC_{50}/IC_{50}$ * |
| Prim. Cat#: 302000 | Sec. Cat#: 302100 | Cytotoxicity, Norepinephrine Uptake | | | | | | | |
| Vial #1 | 1036183 | hum | MDCK cells | 10 µM | ≥ ± 50% | | | | 9 |
| Vial # 2 | 1037044 | hum | MDCK cells | 10 µM | ≥ ± 50% | | | | 11 |
| Vial # 3 | 1037045 | hum | MDCK cells | 10 µM | ≥ ± 50% | | | | -6 |
| Prim. Cat#: 364000 | Sec. Cat#: 364100 | Cytotoxicity, Serotonin (5-Hydroxytryptamine) Uptake | | | | | | | |
| Vial #1 | 1036183 | hum | HEK-293 cells | 10 µM | ≥ ± 50% | | | | 2 |
| Vial # 2 | 1037044 | hum | HEK-293 cells | 10 µM | ≥ ± 50% | | | | -8 |
| Vial # 3 | 1037045 | hum | HEK-293 cells | 10 µM | ≥ ± 50% | | | | -3 |

Figure 63

| Adverse Event | Frequency of Adverse Experiences (%) | | | |
|---|---|---|---|---|
| | Placebo<br>N = 394 | 50 mg/day<br>twice daily<br>N = 426 | 100 mg/day<br>twice daily<br>N = 1871 | 200 mg/day<br>twice daily<br>N = 865 |
| Nausea | 10.9 | 12.7 | 11.2 | 19.4* |
| Headache | 17.0 | 14.6 | 8.4 | 13.5 |
| Increased Sweating | 1.3 | 14.0 | 4.3* | 11.6* |
| Constipation | 4.3 | 8.0 | 6.5 | 11.4* |
| Insomnia | 10.7 | 9.2 | 6.1 | 11.3 |
| Dry mouth | 5.6 | 9.4 | 7.9 | 9.0 |
| Vomiting | 3.6 | 3.8 | 3.9 | 7.9* |
| Abdominal Pain | 5.1 | 6.1 | 6.5 | 7.6 |
| Tremor | 1.5 | 0.9 | 2.5 | 6.7* |
| Anxiety | 1.3 | 2.8 | 4.1 | 5.1 |
| Palpitations | 1.8 | 2.3 | 2.7 | 4.6 |
| Vertigo | 1.8 | 1.6 | 5.0 | 4.5 |
| Fatigue | 3.0 | 2.8 | 2.5 | 4.4 |
| Dysuria | 0.3 | 1.4 | 2.1* | 3.7* |
| Hot flushes | 0 | 1.6 | 3.0 | 3.6 |
| Somnolence | 3.8 | 5.4 | 2.3 | 3.5 |
| Agitation | 3.0 | 1.6 | 3.3 | 2.9 |
| Nervousness | 2.0 | 4.2 | 2.0 | 2.8 |
| Dyspepsia | 4.1 | 3.5 | 2.1 | 2.2 |

* Significantly greater than placebo

STEREOISOMERS OF P-HYDROXY-MILNACIPRAN, AND METHODS OF USE THEREOF

RELATED APPLICATIONS

This application claims the benefit of priority to U.S. Provisional Patent Application Ser. No. 60/445,142, filed Feb. 5, 2003; U.S. Provisional Patent Application Ser. No. 60/423,062, filed Nov. 1, 2002; and U.S. Provisional Patent Application Ser. No. 60/421,640, filed Oct. 25, 2002.

BACKGROUND OF THE INVENTION

Efficacy and tolerability are important factors determining the choice of a medication for treatment of mental depression and other mental disorders including Functional Somatic Disorders. The move from tricyclic antidepressants (TCAs) to selective serotonin reuptake inhibitors (SSRIs) involved not only the loss of the direct receptor interactions responsible for the adverse side effects of TCAs, but also the ability to inhibit the reuptake of norepinephrine. Selectivity for the single neurotransmitter, serotonin, may explain why SSRIs tend to be less efficacious than the TCAs, especially in more serious forms of depression (Lopez-Ibor J. et al., 1996, Int. Clin. Psychopharm., 11:41–46). Older TCAs are associated with significant behavioral toxicity, notably psychomotor and cognitive impairment and sedation. SSRIs are largely devoid of these effects, but gastrointestinal disturbances such as nausea and dyspepsia are common with these agents (Hindmarch I., 1997, Human Psychopharmacology, 12:115–119). For example, for widely prescribed SSRI sertraline (Zoloft®, Pfizer) the top three adverse events associated with discontinuation of treatment were nausea, insomnia, and diarrhea (Physician's Desk Reference, 57th Edition, 2003, Thomson Medical).

Efforts toward improving antidepressant medications are guided by cumulative evidence from neurochemical and clinical studies supporting the therapeutic potential of enhancing monoamine function in depression. A number of antidepressant drugs, serotonin and norepinephrine reuptake inhibitors (SNRIs), including duloxetine, venlafaxine, and milnacipran, have been developed based on their interaction with both serotonin (5-HT) and norepinephrine (NE) receptors. Milnacipran is also often referred to as norepinephrine and serotonin reuptake inhibitor (NSRI) since its norepinephrine ("NE") to serotonin ("5-HT") ratio is 2:1 (Moret et al., 1985, Neuropharmacology, 24:1211–1219; Palmier et al., 1989, Eur. J. Clin. Pharmacol., 37:235–238). Current clinical evidence suggests that these new agents may offer improved efficacy and/or faster onset of action compared with SSRIs (Tran P. V. et al., 2003, J. Clin. Psychopharmacol., 23:78–86). Recent trials with milnacipran suggest that this compound is effective in relieving pain both associated with, and independent of, depression (Briley M., 2003, Curr. Opin. Investig. Drugs, 4:42–45; Cypress Bioscience Inc., Cypress Bioscience Inc. Announces Final Results of Milnacipran Phase II Clinical Trial in Fibromyalgia, Media Release, March 21, 2003, Available from: URL: http://www.cypressbio.com).

Milnacipran and methods for its synthesis are described in U.S. Pat. No. 4,478,836. Milnacipran (midalcipran, midacipran, F 2207) inhibits the uptake of both, norepinephrine (NE) and serotonin (5-HT), with an NE to 5-HT ratio of 2:1 (Moret et al., 1985, Neuropharmacology, 24:1211–1219; Palmier et al., 1989, Eur. J. Clin. Pharmacol., 37:235–238) but does not affect the uptake of dopamine. Milnacipran has no affinity for alpha or beta adrenergic, muscarinic, histaminergic, and dopaminergic receptors. This suggests that milnacipran has a low potential to produce anticholinergic, sedative, and stimulant effects. Milnacipran does not affect the number of beta adrenoceptors in rat cortex after chronic administration (Briley M. et al., Int. Clin. Psychopharmac., 1996, 11:10–14). Additional information regarding milnacipran may be found in the Merck Index, 12th Edition, at entry 6281.

Milnacipran (Ixel®, Pierre Fabre), has demonstrated numerous adverse reactions in human clinical trials with tolerability decreasing with increasing dose (Puech A. et al., 1997, Int. Clin. Psychopharm., 12:99–108). In the double-blind, randomized, multicenter clinical study the most frequent spontaneously reported adverse events for 100 mg/day milnacipran twice daily were as follows: abdominal pain (13%), constipation (10%), and headache (9%). Interestingly, when in the same study milnacipran was given 200 mg/day twice daily, pain related adverse reactions decreased (headache to 8% and abdominal pain to 7%) but nausea and vomiting were more pronounced side effects and were reported by 7% of the patients (Guelfi J. D., 1998, Int. Clin. Psychopharm., 13:121–128). In a double-blind comparative study involving 219 elderly patients with depression the only adverse event reported more frequently for milnacipran recipients than for TCA imipramine recipients was nausea. Patients received either milnacipran or imipramine 75–100 mg/day twice daily for 8 weeks (Tignol J. et al., 1998, Acta Psychiatrica Scandinavica, 97:157–165). It was also observed that when milnacipran was administered intravenously to 10 patients, five of them reported transient nausea. Nausea was primarily reported at the moment of peak of milnacipran plasma level (Caron J. et al., 1993, Eur. Neuropsychopharmacol., 3:493–500). This study clearly demonstrates that nausea is directly correlated with the milnacipran blood plasma concentration. In addition, it strongly suggests that the nausea can be a centrally mediated side effect since the drug was given intravenously in this study. Data from other studies suggest that milnacipran may also induce a locally mediated nausea via gastric irritation (the rapid onset of the nausea was observed even prior to achieving peak plasma levels).

The incidence of spontaneously reported milnacipran adverse experiences in placebo-controlled clinical trials is given in FIG. 63 (adverse effect is listed if frequency was more than 2% in milnacipran 100 mg/day group). As it can be clearly seen from data presented in FIG. 63, the incidence of certain adverse events increases with dosage, including nausea, vomiting, sweating, hot flashes, palpitations, tremor, anxiety, dysuria, and insomnia.

It is important to note that in one of the early depression trials, even after one week of milnacipran dose escalation employed to reduce side effects, the most commonly reported reason for discontinuation of treatment because of adverse effects was nausea and vomiting (Leinonen E., 1997, Acta Psychiatr. Scand., 96:497–504). In the recent fibromyalgia clinical trial with the long dose escalation period (four weeks) which was implemented in order to reduce milnacipran side effects and increase patient's tolerance, the most common dose-related side effect reported by patients was nausea (Cypress Bioscience Inc., Cypress Bioscience Inc. Announces Final Results of Milnacipran Phase II Clinical Trial in Fibromyalgia, Media Release, Mar. 21, 2003).

The data presented in FIG. 63 demonstrates that the currently immediate available release formulation of milnacipran is not suitable for the treatment of health conditions that require milnacipran doses equal or above 100 mg/day given either as once a day or twice a day due to high incidence of treatment-emergent side effects that leads to poor patient's tolerance. Higher doses are required in the treatment of severe depression and other associated disorders. As shown in one of the early antidepressant clinical trials, milnacipran dosage of 200 mg/day was superior to the lower doses (Von Frenckell R et al., 1990, Int. Clin. Psychopharmacology., 5:49–56). Milnacipran dosing regime of 100–250 mg daily was recently reported for the treatment of fibromyalgia (U.S. Pat. No. 6,602,911). It would be very difficult to reach the upper limits of the dose range using the currently available formulation due to the dose related treatment emergent side effects and the need to titrate over a long period to reach the required dose.

The (+)-dextro enantiomer of milnacipran (F2695, (+)-1S,2R-milnacipran) is roughly twice as active in inhibiting norepinephrine and serotonin reuptake as the racemic mixture. See Viazzo et al. *Tetrahedron Lett.* 1996, 37, 4519–4522; Deprez et al. *Eur. J. Drug Metab. Pharmacokinet.* 1998, 23, 166–171. Moreover, the (−)-levro enantiomer of milnacipran (F2696, (−)-1R,2S-milnacipran) is much less potent. See id.

In sum, although milnacipran is reasonably effective in treating major depressive episodes, more efficacious methods are needed to treat effectively major depressive episodes and other mental disorders including Functional Somatic Disorders.

SUMMARY OF THE INVENTION

One aspect of the present invention relates to the enantiomers of para-hydroxy-milnacipran or congeners thereof. Biological assay studies revealed that (+)-para-hydroxy-milnacipran is an approximately two-fold more potent inhibitor of norepinephrine uptake compared to inhibition of serotonin uptake. In contrast, (−)-para-hydroxy-milnacipran is an approximately two-fold more potent inhibitor of serotonin uptake compared to inhibition of norepinephrine uptake. The inhibition properties of each enantiomer of para-hydroxy-milnacipran stand in contrast to that of the racemic mixture which inhibits serotonin uptake and norepinephrine uptake with approximately equal potency. Another aspect of the present invention relates to salts and prodrug forms of the aforementioned compounds. A third aspect of the present invention relates to methods of treating mammals suffering from various mental disorders including Functional Somatic Disorders, e.g. depression, chronic pain, or fibromyalgia, comprising administering to a mammal in need thereof a therapeutically effective amount of a compound of the present invention. Yet another aspect of the present invention relates to formulations comprising a compound of the present invention, and a pharmaceutically acceptable excipient.

BRIEF DESCRIPTION OF THE FIGURES

FIG. 10 depicts a HPLC chromatogram of CS1665 (HPLC Conditions: 10% to 95% acetonitrile within 8 min; 2 min at 95%, LM with 0.1% TFA, Flow: 2.0 mL/min, Säule: Zorbax XDB-C8).
FIG. 14 depicts a HPLC chromatogram of CS1710 (HPLC Conditions: 10% to 95% acetonitrile within 8 min; 2 min at 95%, LM with 0.1% TFA, Flow: 2.0 mL/min, Säule: Zorbax XDB-C8).
FIG. 18 depicts a HPLC chromatogram of CS1713(HPLC Conditions: 10% to 95% acetonitrile within 8 min; 2 min at 95%, LM with 0.1% TFA, Flow: 2.OmL/min, Säule: Zorbax XDB-C8).
FIG. 22 depicts a HPLC chromatogram of CS1714 (HPLC Conditions: 10% to 95% acetonitrile within 8 min; 2 min at 95%, LM with 0.1% TFA, Flow: 2.0 mL/min, Säule: Zorbax XDB-C8).
FIG. 32 depicts biological activity data for CS1814 in assays using receptors from human (hum) and rat.
FIG. 33 depicts biological activity data for CS1814 in assays using receptors from human (hum), mouse, guinea pig (gp), syrian hamster (syh), and rat.
FIG. 34 depicts biological activity data for CS1814 in assays using receptors from human (hum) and rat.
FIG. 35 depicts biological activity data for CS1814 in assays using receptors from human (hum).
FIG. 36 depicts biological activity data for various reference compounds.
FIG. 37 depicts biological activity data for various reference compounds.
FIG. 38 depicts biological activity data for various reference compounds.
FIG. 41 depicts biological activity data for CS1713 (Vial #2) and CS1714 (Vial #3).
FIG. 42 depicts biological activity data for CS1713 (Vial #2) and CS1714 (Vial #3).
FIG. 43 depicts biological activity data for CS1713 (Vial #2) and CS1714 (Vial #3).
FIG. 44 depicts biological activity data for CS1713 (Vial #2), CS1714 (Vial #3), and CS1814 (Vial#1).

FIG. 45 depicts biological activity data for CS1713 (Vial #2), CS1714 (Vial #3), and CS1814 (Vial#1).

FIG. 46 depicts biological activity data for CS1714 (Vial #3).

FIG. 57 depicts cellular assay data for reference compounds.

FIG. 58 depicts cellular assay data for reference compounds.

FIG. 59 depicts a summary of significant primary results for CS1814.

FIG. 60 depicts a summary of significant primary results for CS1713 (Vial #2) and CS1714 (Vial #3).

FIG. 61 depicts a summary of significant primary results for CS1814 (Vial #1), CS1713 (Vial #2) and CS1714 (Vial #3).

FIG. 62 depicts a summary of secondary results for CS1814 (Vial #1), CS1713 (Vial #2) and CS1714 (Vial #3).

FIG. 63 depicts incidences of spontaneously reported milnacipran adverse experiences in placebo-controlled clinical trials.

DETAILED DESCRIPTION OF THE INVENTION

Definitions

Figure 1:
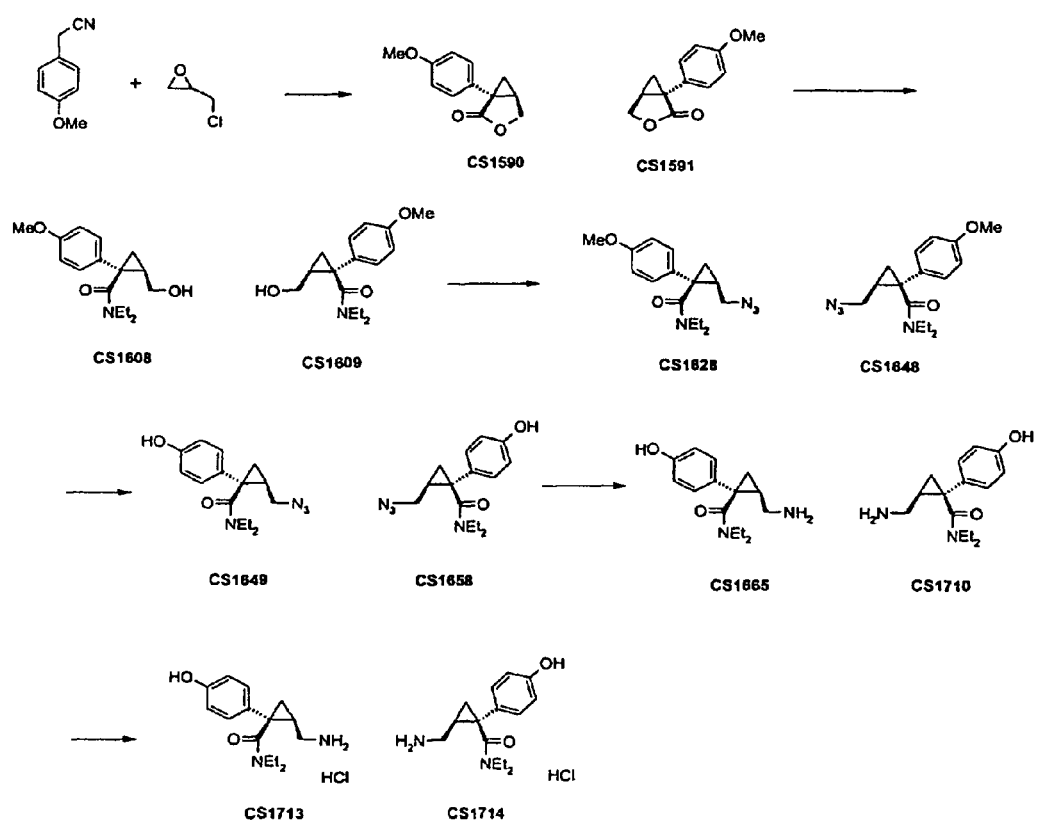
FIG. 1 depicts the synthetic route used to prepare the individual enantiomers of p-hydroxy-milnacipran.
Figure 2:
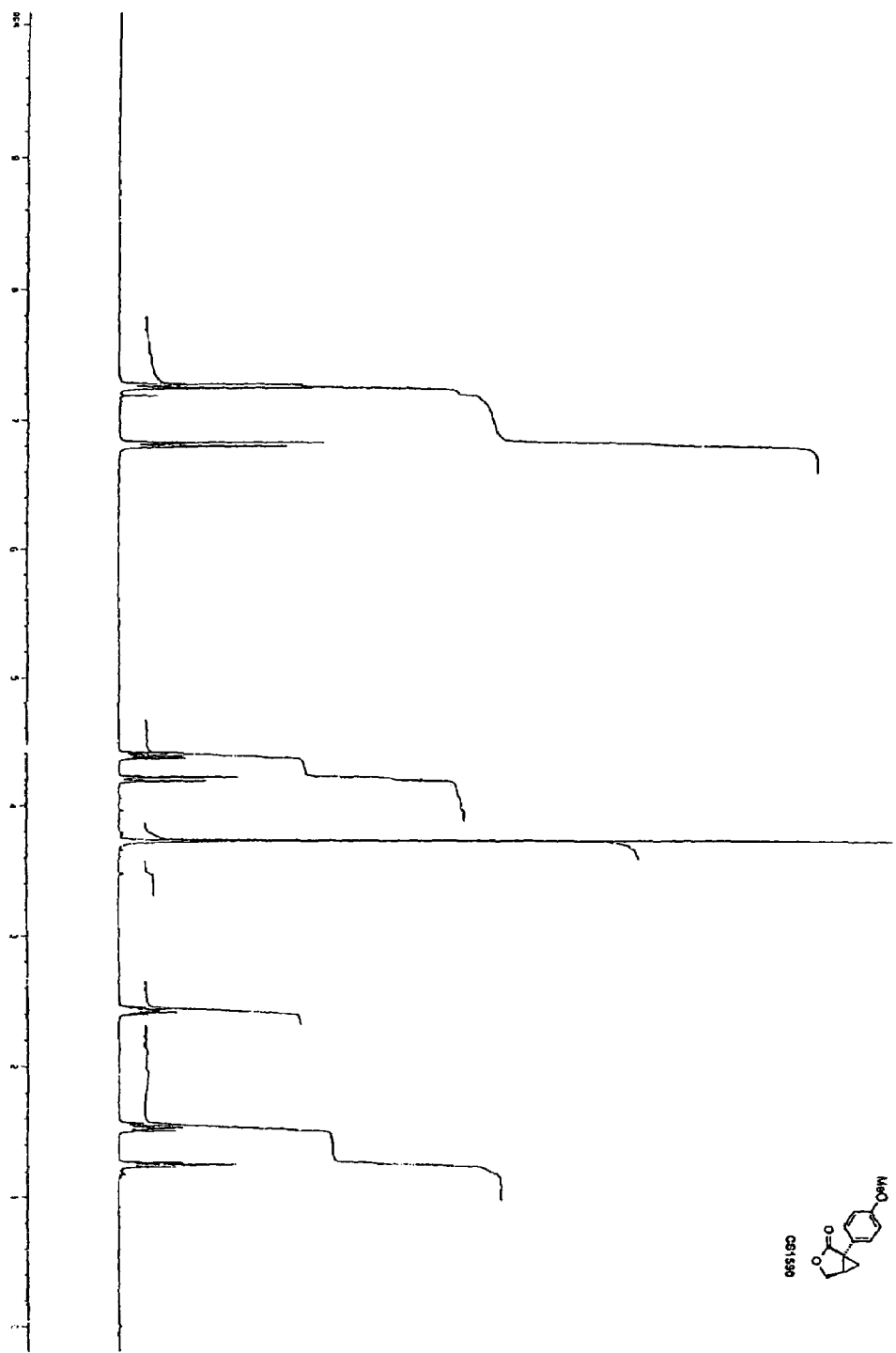
FIG. 2 depicts a $^1$H NMR spectrum of lactone CS1590.
Figure 3:
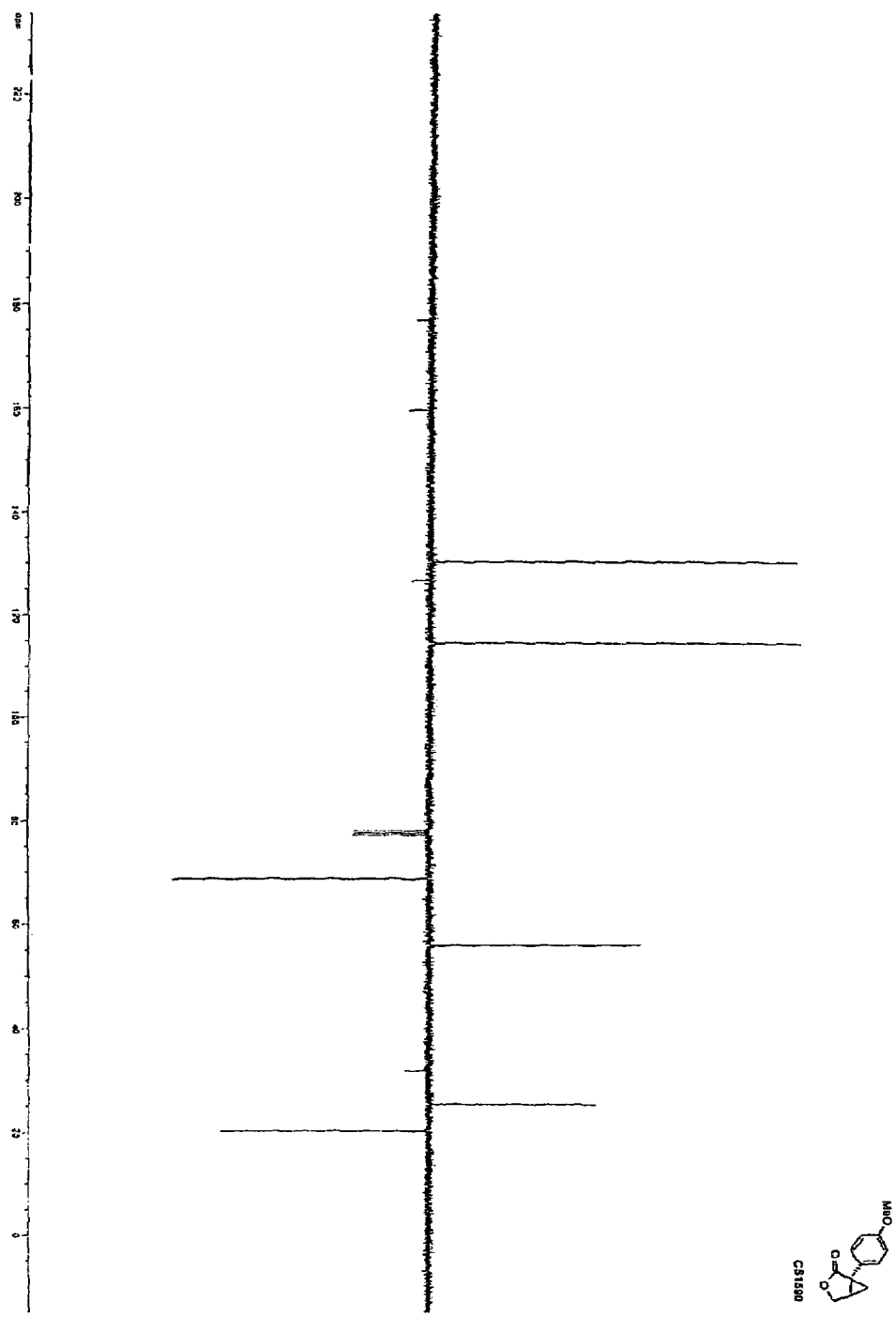
FIG. 3 depicts a $^{13}$C NMR spectrum of lactone CS1590.
Figure 4:
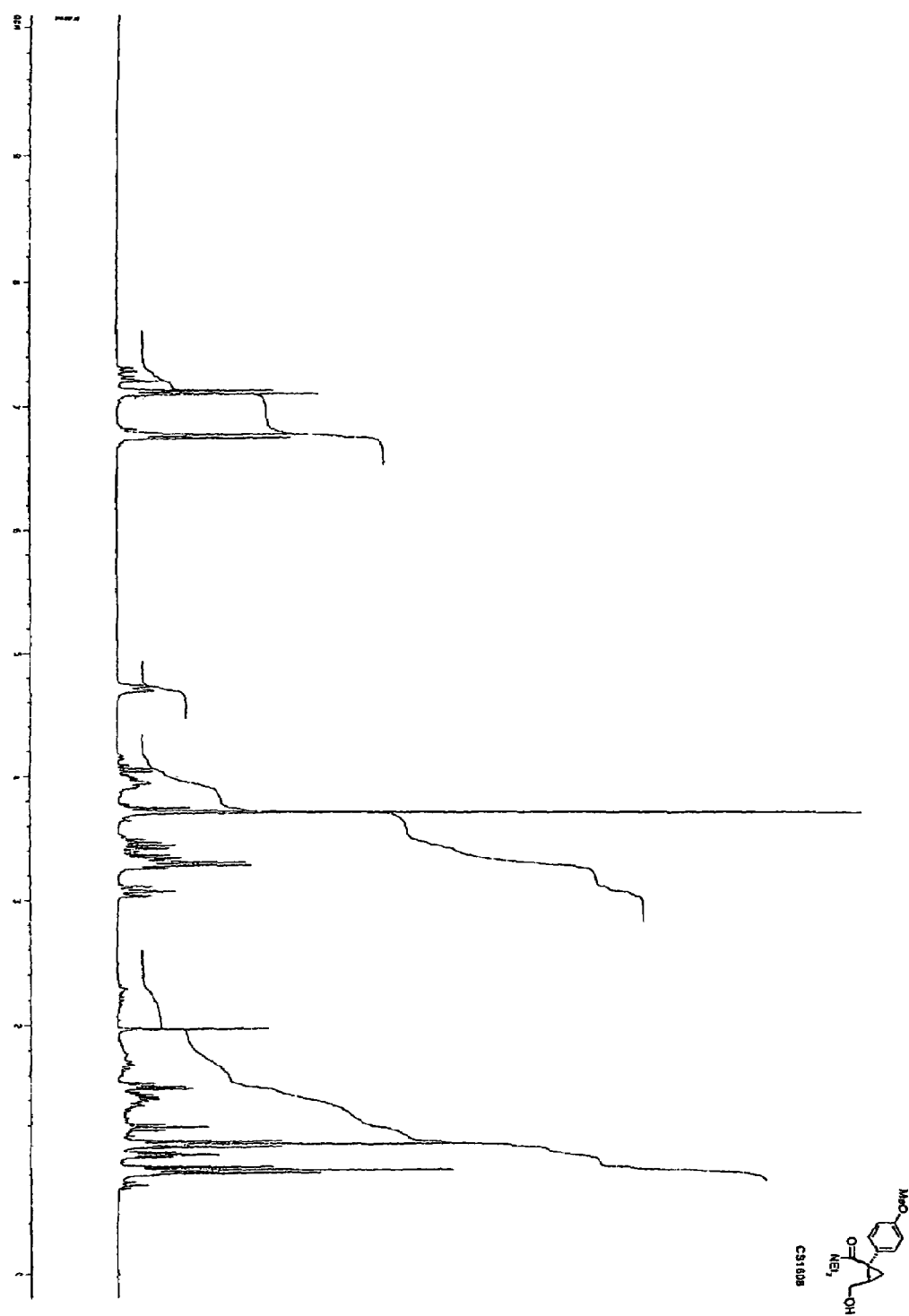
FIG. 4 depicts a $^1$H NMR spectrum of amide CS1608.
Figure 5:
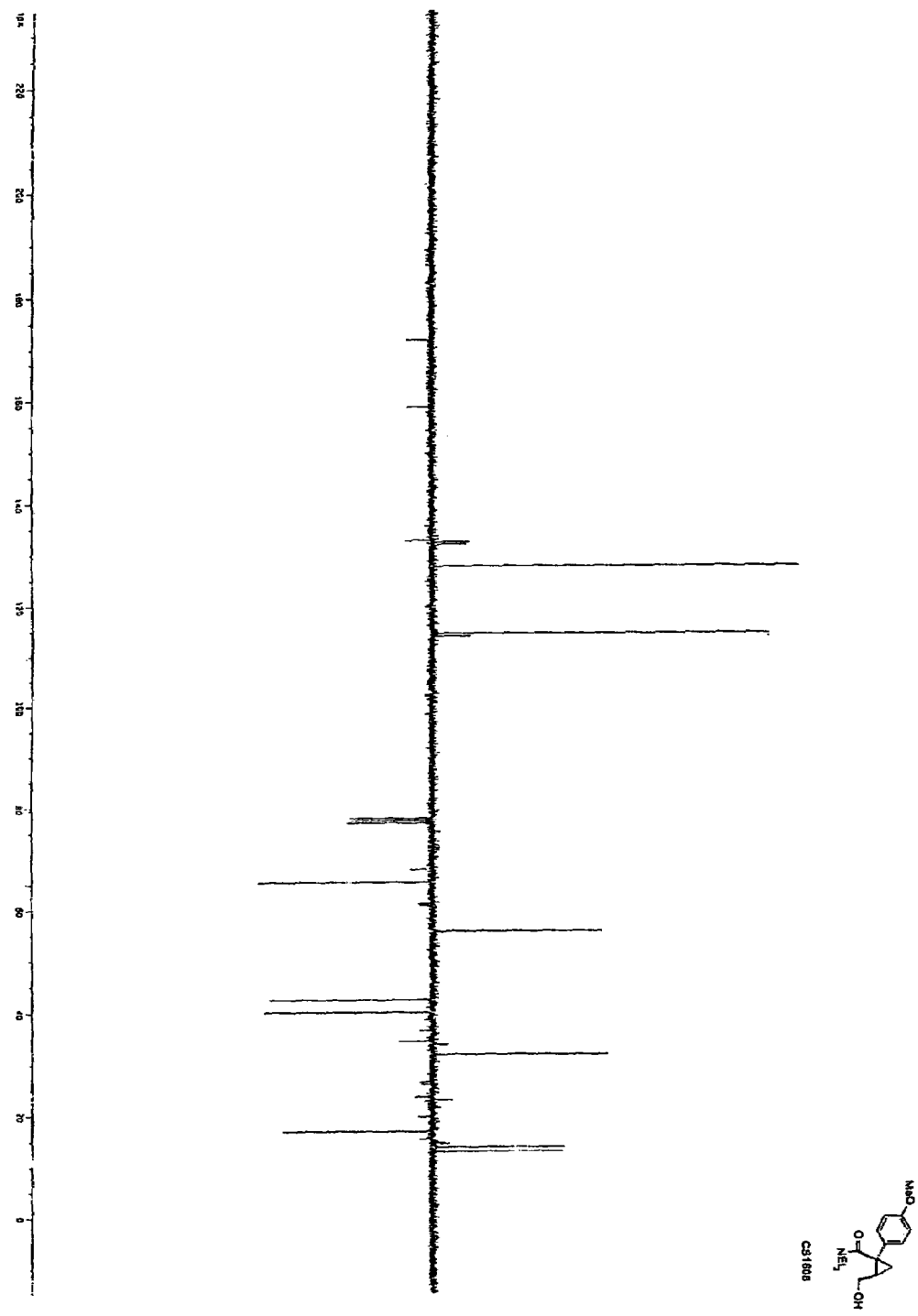
FIG. 5 depicts a $^{13}$C NMR spectrum of amide CS1608.
Figure 6:
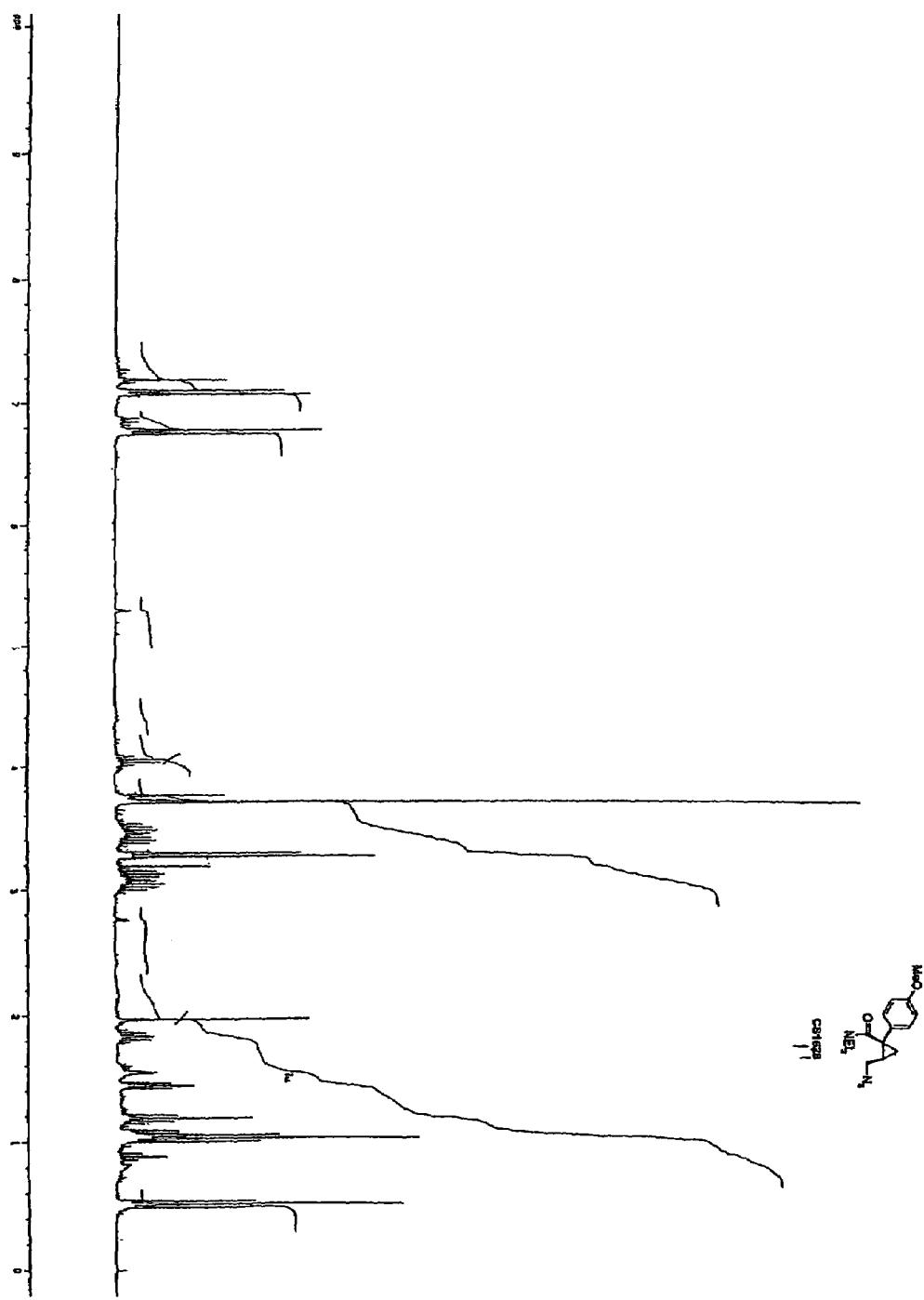
FIG. 6 depicts a $^1$H NMR spectrum of CS1628.
Figure 7:
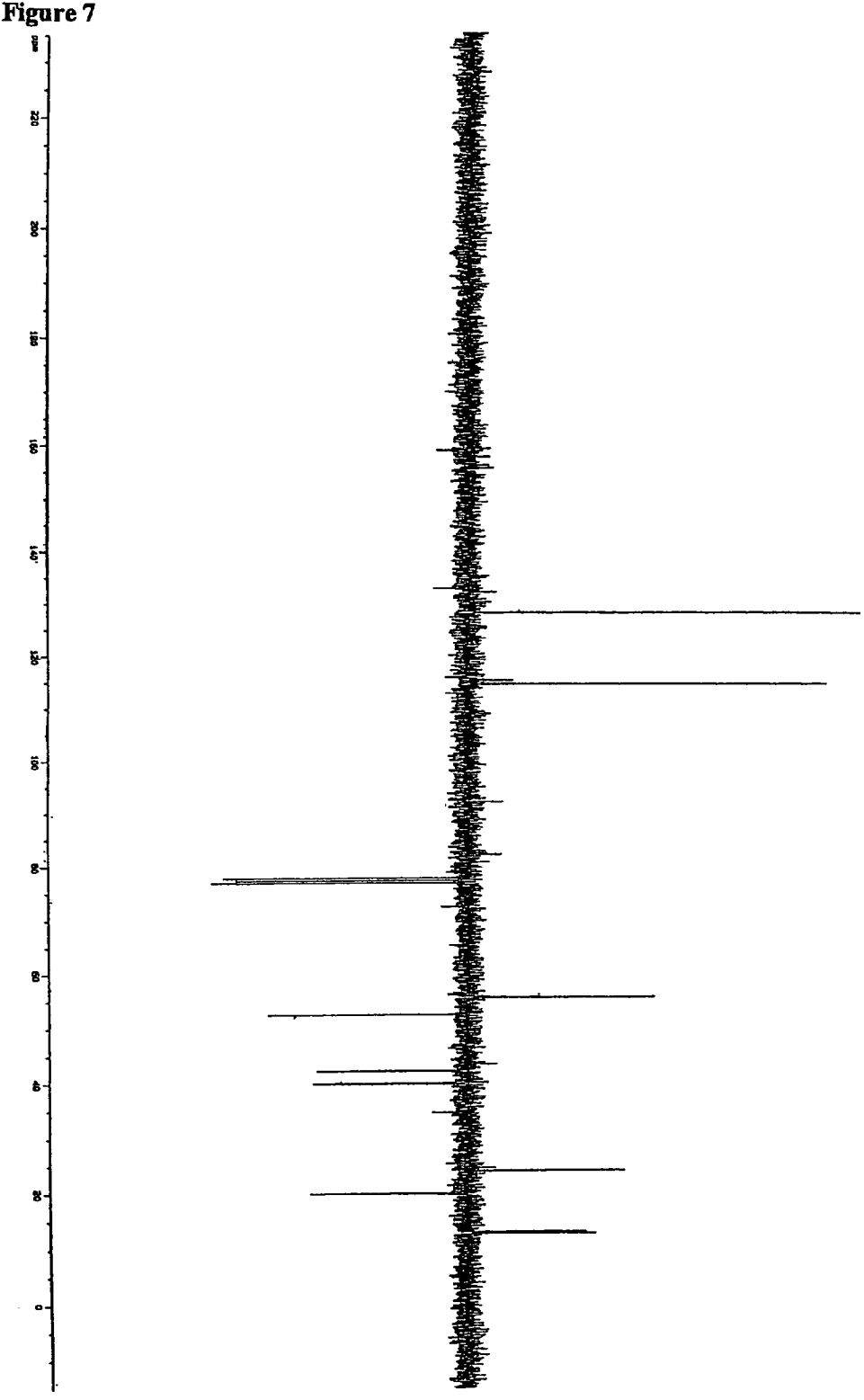
FIG. 7 depicts a $^{13}$C NMR spectrum of CS1628.
Figure 8:
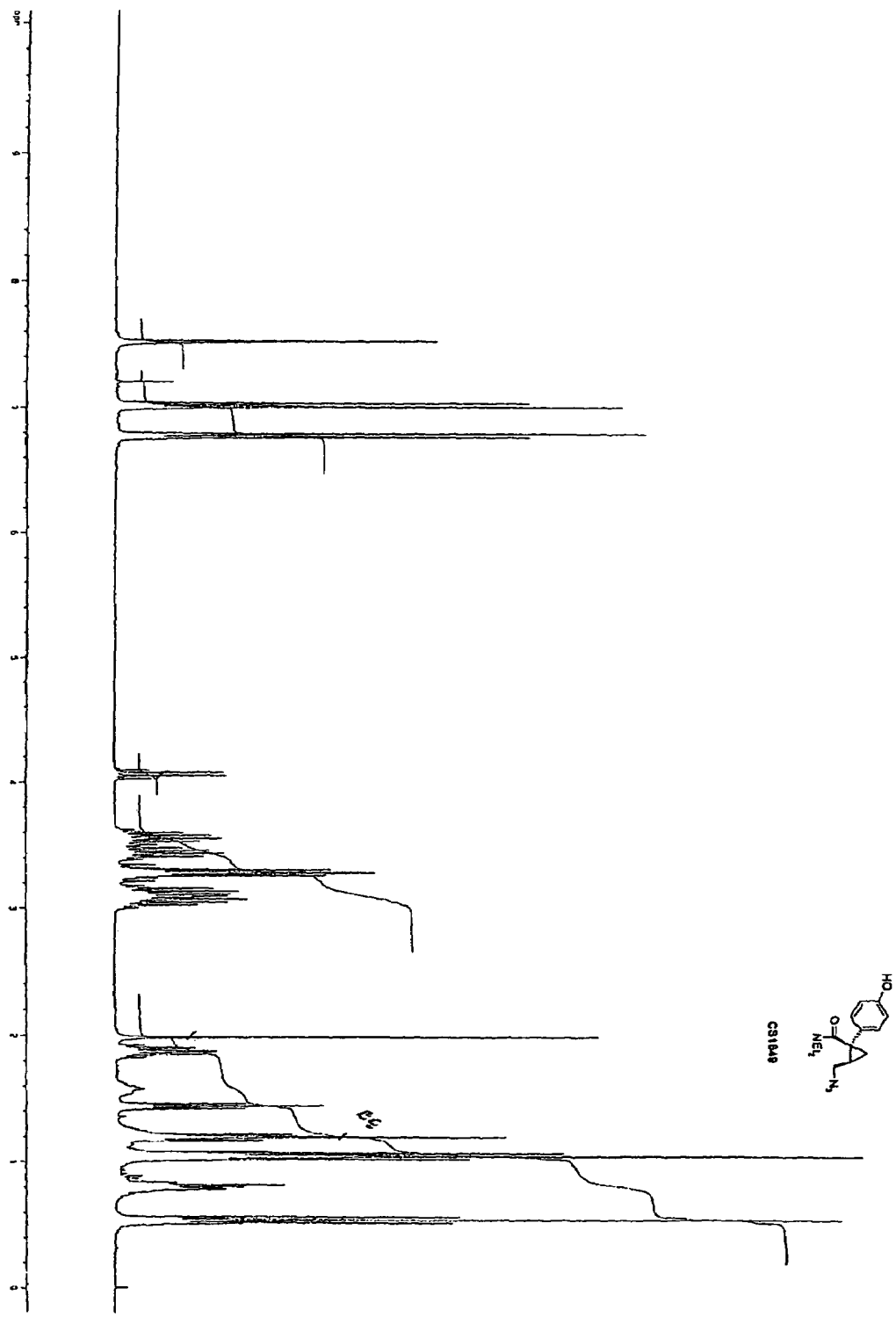
FIG. 8 depicts a $^1$H NMR spectrum of CS1649.
Figure 9:
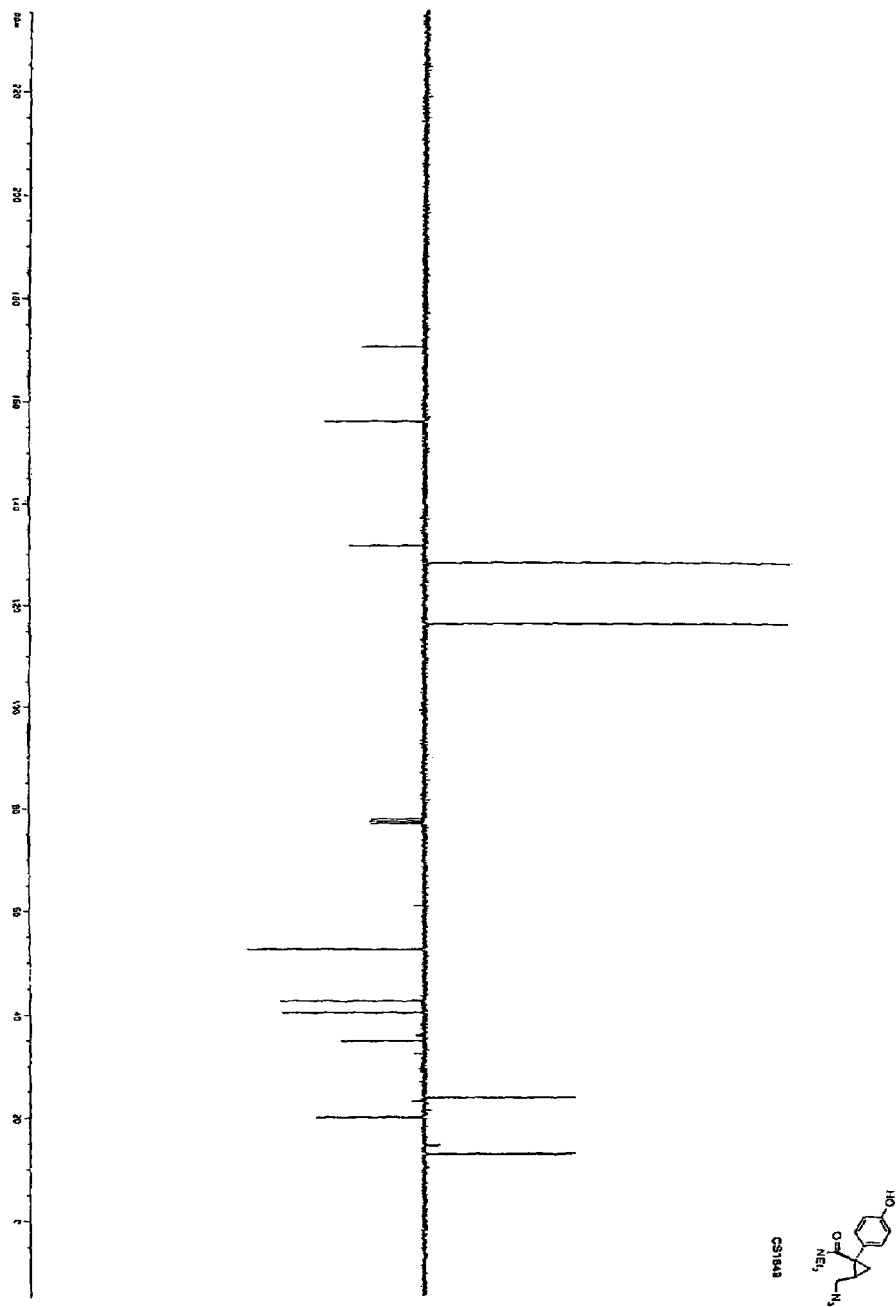
FIG. 9 depicts a $^{13}$C NMR spectrum of CS1649.
Figure 11:
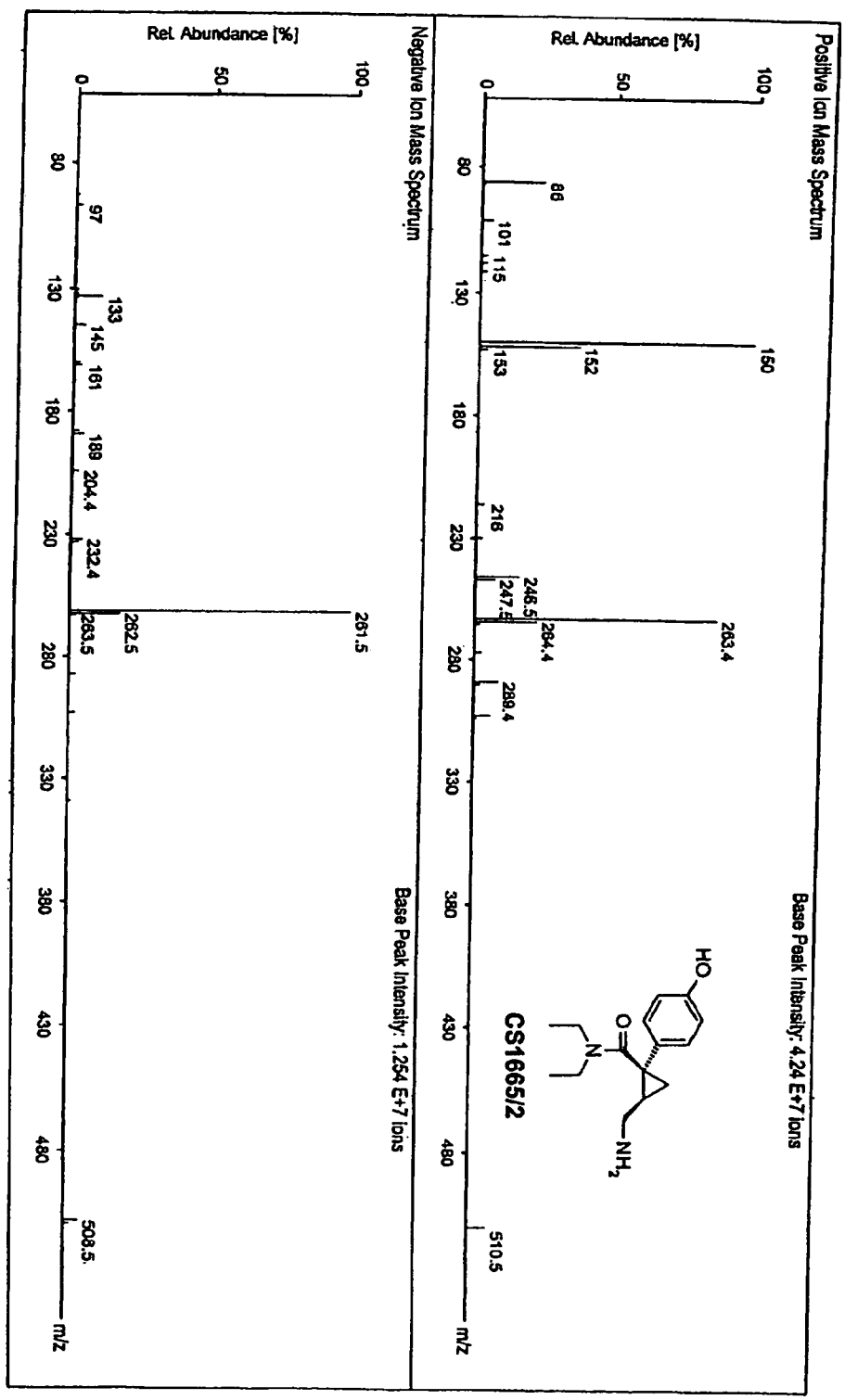
FIG. 11 depicts a mass spectrum of CS1665.

For convenience, certain terms employed in the specification, examples, and appended claims are collected here.

The term "milnacipran" refers to the racemic mixture of the tri-substituted cyclopropane depicted below.

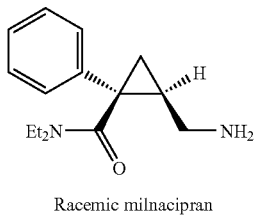

Racemic milnacipran

The term "$ED_{50}$" means the dose of a drug which produces 50% of its maximum response or effect. Alternatively, the dose which produces a pre-determined response in 50% of test subjects or preparations.

Compounds refered to in the specification and figures are identified using a six-character alpha-numeric code. For example, racemic p-hydroxy-milnacipran is CS1814. In certain instances, the six-character alpha-numeric code is followed by forward slash and a number. The forward slash followed by a number indicates the batch from which the data was taken. For example, CS1814/1 indicates that the compound is p-hydroxy-milnacipran and the data was taken from batch 1.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "inverse agonist" refers to a compound that binds to a constitutively active receptor site and reduces its physiological function.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigina ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, alkylsulfonyl, arylsulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, alkylsulfonyl, arylsulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, alkylsulfonyl, arylsulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, alkylsulfonyl, arylsulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the terms "hydroxy" and "hydroxyl" mean —OH; and the term "sulfonyl" means —SO$_2$—.

The terms "akin" and "amino" are art-recognized and refer to both unsubstituted and substituted amines, e.g., a moiety that can be represented by the general formula:

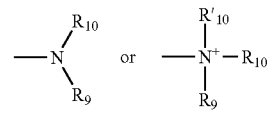

wherein R$_9$, R$_{10}$ and R'$_{10}$ each independently represent a group permitted by the rules of valence.

The term "acylamino" is art-recognized and refers to a moiety that can be represented by the general formula:

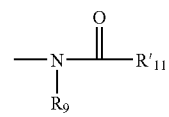

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

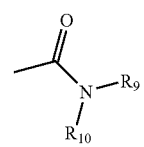

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

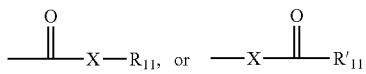

wherein X is a bond or represents an oxygen or a sulfur, and $R_{11}$ represents a hydrogen, an alkyl, an alkenyl, $—(CH_2)_m—R_8$ or a pharmaceutically acceptable salt, $R'_{11}$ represents a hydrogen, an alkyl, an alkenyl or $—(CH_2)_m—R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, $—O—(CH_2)_m—R_8$, where m and $R_8$ are described above.

The term "sulfonate" is art recognized and includes a moiety that can be represented by the general formula:

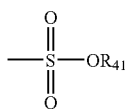

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesuflonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

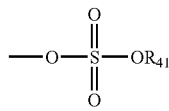

in which $R_{41}$ is as defined above.

The term "sulfonyamino" is art recognized and includes a moiety that can be represented by the general formula:

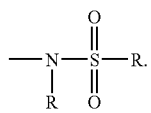

The term "sulfamoyl" is art-recognized and includes a moiety that can be represented by the general formula:

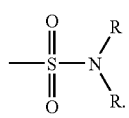

The term "sulfony", as used herein, refers to a moiety that can be represented by the general formula:

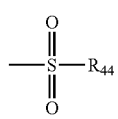

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

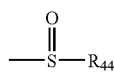

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and $—Se—(CH_2)_m—R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Synthesis of Individual Enanteriomers of p-Hydroxy-Milnacipran

The condensation reaction of 4-methoxybenzylcyanide and enantiomerically pure epichlorhydrin (FIG. 1), which are both commercially available, gave access to the corresponding lactones CS1590 and CS1591 in satisfactory yield. Subsequent opening of the lactone in the presence of lithiumdiethylamide, generated from n-butyllithium and diethylamine, furnished CS1608 and the corresponding enantiomer, respectively. Conversion of the primary alcohols CS1608 and CS1609 to the azides CS1628 and C1648 was accomplished in a pot procedure by in situ generation of the corresponding mesylates followed by nucleophilic displacement with sodium azide. Following this protocol the desired azides were obtained in 36–40% yield. Subsequent removal of the protecting group was carried out in the presence of borontribromide at −30° C. for 48 h and produced the deprotected phenols CS1649 and CS1658 in 66% yield. Final reduction of the azide moiety in CS1649 and CS1658 under standard reaction conditions furnished the desired target compounds CS1665 and CS1710. Preparation of the corresponding hydrochloric acid salts was accomplished by using hydrochloric acid in dioxane and subsequent removal of the solvent.

Methods for the Resolution of Enantiomers

One alternative procedure for the isolation of an individual enantiomer is by resolution of an enantiomer from a racemic mixture. Today, chiral separations of cationic drugs by capillary electrophoresis are generally carried out by adding negatively charged cyclodextrins (CDs) to the running buffer, while anionic or neutral drug separations require the use of dual-CD systems (mixtures of neutral and charged CDs). Chiral separation of some basic drugs (idazoxan, efaroxan, milnacipran) has been studied by mixtures of sulfated-β-CD (S-βCD) and hydroxypropl-γ-CD (HP-γ-CD). The influence of the following parameters (nature and concentration of neutral CD, concentration of S-β-CD) on many separation factors (electrophoretic mobility, selectivity, efficiency, asymmetry factor, resolution) demonstrated that dual-CD systems are useful for chiral separation of basic drugs in order to improve the symmetry of the second-migrating enantiomer. Indeed, the neutral CD reduces the extent of electromigration dispersion by mobility tuning. Finally, the 0.5 mg/mL S-β-CD/5 mg/mL HPγ-CD dual system has allowed the chiral separation of idazoxan, efaroxan and milnacipran enantiomers in less than 9 min. See generally Grard, S. et al. *Electrophoresis* 2000, 21, 3028–3034.

Biological Activity Analysis

The results from the biological testing of CS1814, CS1713, CS1714, and various reference compounds are presented in FIGS. 32–62. CS1814 (Vial #1), CS1713 (Vial #2), and CS1714 (Vial #3) were evaluated in various radioligand binding assays, and for inhibition of CYP450 3A4 at initial concentrations of 10 μM. As depicted in FIGS. 59 and 60, significant activity (≧50%) was observed for displacement of radioligand from Serotonin Transporter binding sites (Vial #1 Ki=6.73 nM, Vial #2 Ki=3.88 nM, Vial #3 Ki=8.15 nM) and Norepinephrine Transporter binding sites (Vial #1 Ki=0.218 μM, Vial #2 Ki=0.112 μM, Vial #3 Ki=1.68 μM).

In addition, CS1713 (Vial #2), CS1714 (Vial #3), and CS1814 (Vial #1) were evaluated for inhibition of cellular Serotonin and Norepinephrine Uptake. As depicted in FIG. 61, CS1814 (Vial #1) is approximately equipotent in inhibiting serotonin and norepinephrine uptake ($IC_{50}$=28.6 nM for norepinephrine, $IC_{50}$=21.7 nM for serotonin). Interestingly, CS1713 (Vial #2) is a more potent inhibitor of norepinephrine uptake than serotonin uptake ($IC_{50}$=10.3 nM for norepinephrine, $IC_{50}$=22 nM for serotonin). In contrast, CS1714 (Vial #3) is a more potent inhibitor of serotonin uptake compared to norepinephrin uptake ($IC_{50}$=88.5 nM for norepinephrine, $IC_{50}$=40.3 nM for serotonin). The fact that CS1713 (Vial #2) is a more potent inhibitor of norepinephrine uptake would render it a superior therapeutic agent for treating diseases linked to norepinephrine uptake. In addition, the CS1714 (Vial #3) would useful for treating conditions requiring selective inhibition of serotonin uptake.

Importantly, no cytotoxicity was observed for CS1713 (Vial #2), CS1714 (Vial #3), or CS1814 (Vial #1) at 10 μM. In addition, CS1814 (Vial #1) is a selective inhibitor of norepinephrine and serotonin receptors. The fact that CS1814 generally does not bind well to other receptors, as depicted in FIGS. 32 and 33, substantially reduces the risk of negative side effects associated with administering the compound to a patient. Therefore, it is likely that CS1713 and CS1714 will not have detrimental side effects.

Compounds & Methods of the Invention

In certain embodiments, a compound of the present invention is an isolated compound represented by A:

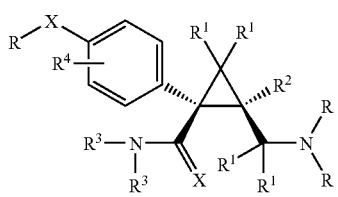

A wherein

X represents independently for each occurrence O, S, or NR;

R represents independently for each occurrence H, alkyl, cycloalkyl, alkenyl, aryl, heteroaryl, arylalkyl, formyl, acyl, silyl, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;

$R^1$ represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;

$R^2$ represents independently for each occurrence H, alkyl, cycloalkyl, alkenyl, aryl, heteroaryl, arylalkyl, or —(CH$_2$)$_m$—R$_{80}$;

$R^3$ represents independently for each occurrence H, alkyl, cycloalkyl, alkenyl, aryl, heteroaryl, arylalkyl, or —(CH$_2$)$_m$—R$_{80}$;

$R^4$ is absent or present between one and four times inclusive;

$R^4$, if present, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

In certain embodiments, the compounds of the present invention are represented by A and the attendant definitions, wherein X represents O.

In certain embodiments, the compounds of the present invention are represented by A and the attendant definitions, wherein R represents H.

In certain embodiments, the compounds of the present invention are represented by A and the attendant definitions, wherein $R^1$ represents H.

In certain embodiments, the compounds of the present invention are represented by A and the attendant definitions, wherein $R^2$ represents H.

In certain embodiments, the compounds of the present invention are represented by A and the attendant definitions, wherein $R^3$ represents alkyl.

In certain embodiments, the compounds of the present invention are represented by A and the attendant definitions, wherein $R^4$ is absent.

In certain embodiments, the compounds of the present invention are represented by A and the attendant definitions, wherein X represents O; and R represents H.

In certain embodiments, the compounds of the present invention are represented by A and the attendant definitions, wherein X represents O; R represents H; and $R^1$ represents H.

In certain embodiments, the compounds of the present invention are represented by A and the attendant definitions, wherein X represents O; R represents H; $R^1$ represents H; and $R^2$ represents H.

In certain embodiments, the compounds of the present invention are represented by A and the attendant definitions, wherein X represents O; R represents H; $R^1$ represents H; $R^2$ represents H; and $R^3$ represents alkyl.

In certain embodiments, the compounds of the present invention are represented by A and the attendant definitions, wherein X represents O; R represents H; $R^1$ represents H; $R^2$ represents H; $R^3$ represents alkyl; and $R^4$ is absent.

In certain embodiments, the compounds of the present invention are represented by A and the attendant definitions, wherein X represents O; R represents H; $R^1$ represents H; $R^2$ represents H; $R^3$ represents ethyl; and $R^4$ is absent.

In an assay based on a mammalian GPCR, certain compounds according to structure A have $IC_{50}$ values less than 10 μM, more preferably less than 1 μM, even more preferably less than 100 nM, and most preferably less than 10 nM.

In an assay based on a mammalian GPCR, certain compounds according to structure A have $EC_{50}$ values less than 10 μM, more preferably less than 1 μM, even more preferably less than 100 nM, and most preferably less than 10 nM.

In certain embodiments, compounds according to structure A are effective in the treatment of a mammal suffering from depression.

In certain embodiments, compounds according to structure A are effective in the treatment of a mammal suffering from fibromyalgia syndrome.

In certain embodiments, compounds according to structure A are effective in the treatment of a mammal suffering from mental disorders including Functional Somatic Disorders, for example, depression, fibromyalgia syndrome, chronic fatigue syndrome, pain, attention deficit/hyperactivity disorder, and visceral pain syndromes (VPS), such as irritable bowel syndrome (IBS), noncardiac chest pain (NCCP), functional dyspepsia, interstitial cystitis, essential vulvodynia, urethral syndrome, orchialgia, and affective disorders, including depressive disorders (major depressive disorder, dysthymia, atypical depression) and anxiety disorders (generalized anxiety disorder, phobias, obsessive compulsive disorder, panic disorder, post-traumatic stress disorder), premenstrual dysphoric disorder, temperomandibular disorder, atypical face pain, migraine headache, and tension headache.

In certain embodiments, a compound of the present invention is an isolated compound represented by B:

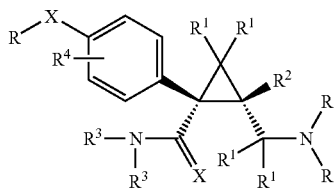

B wherein

X represents independently for each occurrence O, S, or NR;

R represents independently for each occurrence H, alkyl, cycloalkyl, alkenyl, aryl, heteroaryl, arylalkyl, formyl, acyl, silyl, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

$R^1$ represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

$R^2$ represents independently for each occurrence H, alkyl, cycloalkyl, alkenyl, aryl, heteroaryl, arylalkyl, or —$(CH_2)_m$—$R_{80}$;

$R^3$ represents independently for each occurrence H, alkyl, cycloalkyl, alkenyl, aryl, heteroaryl, arylalkyl, or —$(CH_2)_m$—$R_{80}$;

$R^4$ is absent or present between one and four times inclusive;

$R^4$, if present, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

In certain embodiments, the compounds of the present invention are represented by B and the attendant definitions, wherein X represents O.

In certain embodiments, the compounds of the present invention are represented by B and the attendant definitions, wherein R represents H.

In certain embodiments, the compounds of the present invention are represented by B and the attendant definitions, wherein $R^1$ represents H.

In certain embodiments, the compounds of the present invention are represented by B and the attendant definitions, wherein $R^2$ represents H.

In certain embodiments, the compounds of the present invention are represented by B and the attendant definitions, wherein $R^3$ represents alkyl.

In certain embodiments, the compounds of the present invention are represented by B and the attendant definitions, wherein $R^4$ is absent.

In certain embodiments, the compounds of the present invention are represented by B and the attendant definitions, wherein X represents O; and R represents H.

In certain embodiments, the compounds of the present invention are represented by B and the attendant definitions, wherein X represents O; R represents H; and $R^1$ represents H.

In certain embodiments, the compounds of the present invention are represented by B and the attendant definitions, wherein X represents O; R represents H; $R^1$ represents H; and $R^2$ represents H.

In certain embodiments, the compounds of the present invention are represented by B and the attendant definitions, wherein X represents O; R represents H; $R^1$ represents H; $R^2$ represents H; and $R^3$ represents alkyl.

In certain embodiments, the compounds of the present invention are represented by B and the attendant definitions, wherein X represents O; R represents H; $R^1$ represents H; $R^2$ represents H; $R^3$ represents alkyl; and $R^4$ is absent.

In certain embodiments, the compounds of the present invention are represented by B and the attendant definitions, wherein X represents O; R represents H; $R^1$ represents H; $R^2$ represents H; $R^3$ represents ethyl; and $R^4$ is absent.

In an assay based on a mammalian GPCR, certain compounds according to structure B have $IC_{50}$ values less than 10 μM, more preferably less than 1 μM, even more preferably less than 100 nM, and most preferably less than 10 nM.

In an assay based on a mammalian GPCR, certain compounds according to structure B have $EC_{50}$ values less than 10 µM, more preferably less than 1 µM, even more preferably less than 100 nM, and most preferably less than 10 nM.

In certain embodiments, compounds according to structure B are effective in the treatment of a mammal suffering from depression.

In certain embodiments, compounds according to structure B are effective in the treatment of a mammal suffering from fibromyalgia syndrome.

In certain embodiments, compounds according to structure B are effective in the treatment of a mammal suffering from mental disorders including Functional Somatic Disorders, for example, depression, fibromyalgia syndrome, chronic fatigue syndrome, pain, attention deficit/hyperactivity disorder, and visceral pain syndromes (VPS), such as irritable bowel syndrome (IBS), noncardiac chest pain (NCCP), functional dyspepsia, interstitial cystitis, essential vulvodynia, urethral syndrome, orchialgia, and affective disorders, including depressive disorders (major depressive disorder, dysthymia, atypical depression) and anxiety disorders (generalized anxiety disorder, phobias, obsessive compulsive disorder, panic disorder, post-traumatic stress disorder), premenstrual dysphoric disorder, temperomandibular disorder, atypical face pain, migraine headache, and tension headache.

In certain embodiments, the compound of the invention is selected from the group 1S, 2R 1-(4-Methoxy-phenyl9-3-oxa-bicyclo[3.1.0]hexan-2-one (CS1590), 1R, 2S 1-(4-Methoxy-phenyl9-3-oxa-bicyclo[3.1.0]hexan-2-one (CS1591), 1S, 2R 2-Hydroxymethyl-1-(4-methoxy-phenyl)-cyclopropanecarboxylic acid diethylamide (CS1608), 1R, 2S 2-Hydroxymethyl-1-(4-methoxy-phenyl)-cyclopropanecarboxylic acid diethylamide (CS1609), 1S, 2R 2-Azidomethyl-1-(4-methoxy-phenyl)-cyclopropanecarboxylic acid diethylamide (CS1628), 1R, 2S 2-Azidomethyl-1-(4-methoxy-phenyl)-cyclopropanecarboxylic acid diethylamide (CS1648), 1S, 2R 2-Azidomethyl-1-(4-hydroxy-phenyl)-cyclopropanecarboxylic acid diethylamide (CS1649), 1R, 2S 2-Azidomethyl-1-(4-hydroxy-phenyl)-cyclopropanecarboxylic acid diethylamide (CS1658), 1S, 2R 2-Aminomethyl-1-(4-hydroxy-phenyl)-cyclopropanecarboxylic acid diethyl amide (CS1665), 1R, 2S 2-Aminomethyl-1-(4-hydroxy-phenyl)-cyclopropanecarboxylic acid diethyl amide (CS1710), and racemic 2-Aminomethyl-1-(4-hydroxy-phenyl)-cyclopropanecarboxylic acid diethyl amide (CS1814).

In certain embodiments, the present invention relates to a formulation, comprising a compound represented by any of the structures outlined above; and a pharmaceutically acceptable excipient.

In certain embodiments, the compounds of this invention can be administered adjunctively with other active compounds such as analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, antinarcoleptic, and anorectics.

Specific examples of compounds that can be adjunctively administered with the compounds of this invention include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepamn, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil, molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

By adjunctive administration is meant simultaneous administration of the compounds, in the same dosage form, simultaneous administration in separate dosage forms, and separate administration of the compounds.

In certain embodiments, the present invention relates to ligands for a GPCR, e.g., a receptor for a neurotransmitter, wherein the ligands are represented by a structure outlined above, and any of the sets of definitions associated with a structure. In certain embodiments, the ligands of the present invention are antagonists, agonists, partial agonists or inverse agonists of a GPCR. In certain preferred embodiments, the ligands of the present invention are antagonists of the reuptake of serotonin or norepinephrine or both. In any event, the ligands of the present invention preferably exert their effect on a GPCR at a concentration less than about 10 micromolar, more preferably less than about 1 micromolar, even more preferably at a concentration less than about 100 nanomolar, and most preferably at a concentration less than 10 nanomolar. In certain preferred embodiments, the ligands of the present invention are antagonists of a the reuptake of serotonin or norepinephrine or both at a concentration less than about 10 micromolar, more preferably less than about 1 micromolar, even more preferably at a concentration less than about 100 nanomolar, and most preferably at a concentration less than 10 nanomolar.

The compounds of the invention are indicated for use in the treatment of inflammatory, immunological, bronchopulmonary, cardiovascular, oncological or CNS-degenerative disorders; preferably for oral or topical treatment of inflammatory and/or immunological disorders, such as the oral or topical treatment of airway diseases involving inflammatory conditions, e.g. asthma, bronchitis; or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants. The compounds of the invention are also indicated for use in treatment of heart failure, and in treatment of diabetic patients with macular edema or diabetic retinopathy.

One embodiment of the invention is the treatment of a patient having inflammatory pain. For example, administration of certain kinase inhibitors significantly diminishes both acute and chronic hyperalgesia resulting from exposure to the inflammatory agent carrageenan; moreover, administration of certain kinase inhibitors diminishes hyperalgesia due to diabetes, chemotherapy or traumatic nerve injury. Such inflammatory pain may be acute or chronic and can be due to any number of conditions characterized by inflammation including, without limitation, sunburn, rheumatoid arthritis, osteoarthritis, colitis, carditis, dermatitis, myositis, neuritis and collagen vascular diseases. In addition, administration of a compound of the present invention to a subject immediately prior to, during or after an inflammatory event can ameliorate both the acute pain and the chronic hyperalgesia that the subject would otherwise experience.

Another preferred embodiment of the invention is the treatment of a patient having neuropathic pain. Such patients can have a neuropathy classified as a radiculopathy, mononeuropathy, mononeuropathy multiplex, polyneuropathy or plexopathy. Diseases in these classes can be caused by a variety of nerve-damaging conditions or procedures, including, without limitation, trauma, stroke, demyelinating diseases, abscess, surgery, amputation, inflammatory diseases of the nerves, causalgia, diabetes, collagen vascular diseases, trigeminal neuralgia, rheumatoid arthritis, toxins, cancer (which can cause direct or remote (e.g. paraneoplastic) nerve damage), chronic alcoholism, herpes infection, AIDS, and chemotherapy. Nerve damage causing hyperalgesia can be in peripheral or CNS nerves. This embodiment of the invention is based on the fact that administration of certain kinase inhibitors significantly diminishes hyperalgesia due to diabetes, chemotherapy or traumatic nerve injury.

Preferred embodiments of the present invention include a composition combining a compound of the present invention with one or more additional pain-reducing agents and a method of administering such a composition. An individual pain medication often provides only partially effective pain alleviation because it interferes with just one pain-transducing pathway out of many. Alternatively, a compound of the present invention can be administered in combination with a pain-reducing (analgesic) agent that acts at a different point in the pain perception process.

Fibromyalgia syndrome is a chronic and debilitating condition characterized by widespread pain and stiffness throughout the body, accompanied by severe fatigue and headache. It affects an estimated 2%–4% of the population worldwide and is the second most common diagnosis by rheumatologists in the United States, after osteoarthritis. Despite the high prevalence and severity of this syndrome, there are no approved treatments specifically for FMS in the United States or elsewhere. Another preferred embodiment of the present invention relates to treating fibromyalgia by adminstering a therapeutically effective amount of a compound of the present invention to a mammal in need thereof.

Prodrugs and Intermediates

It will be appreciated by those skilled in the art that, although certain protected derivatives of the compounds of the present invention, which may be made prior to a final deprotection stage, may not possess pharmacological activity as such, they may be administered parenterally or orally and thereafter metabolized in the body to form compounds of the invention which are pharmacologically active. Such derivatives may therefore be described as "prodrugs". Moreover, certain compounds of the present invention may act as prodrugs of other compounds of the present invention. Critically, all prodrugs of compounds of the present invention are included within the scope of the present invention. Novel intermediates as described hereinbefore and their use in the manufacture of other compounds of the present invention also form part of the invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary akin. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion ethod. In a congealing method, the drug is mixed with a wax material and either spray-congealed or congealed and screened and processed.

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit®. L30D-55 and L100-55 (soluble at pH 5.5 and above), Eudragit®. L-100 (soluble at pH 6.0 and above), Eudragit®. S (soluble at pH 7.0 and above, as a result of a higher degree of esterification), and Eudragits®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an antifoaming agent, such as a silicone (e.g., simethicone), may also be added to the coating composition.

Alternatively, a delayed release tablet may be formulated by dispersing the drug within a matrix of a suitable material such as a hydrophilic polymer or a fatty compound. The hydrophilic polymers may be comprised of polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Combination Therapy

The compounds of the invention may be administered to a patient in combination with one or more therapeutic agents. The complementary drug or drugs may be mixed with the primary drug and formulated into a single tablet, pill, capsule, or solution for parenteral administration, and the like. Alternatively, the primary drug and complementary drug may be administered via separate compositions, e.g. separate tablets or solutions. The primary drug may be administered at the same time as the complementary drug or the primary drug may be administered intermittently with the complementary drug. The dosage of the complementary drug will generally be dependent upon a number of factors including the health of the patient being treated, the extent of treatment desired, the nature and kind of concurrent therapy, if any, and the frequency of treatment and the nature of the effect desired. In general, dosage ranges of the complementary drugs often range from about 0.001 to about 250 mg/kg body weight per day. For a normal adult having a body weight of about 70 kg, a dosage in the range of from about 0.1 to about 25 mg/kg body weight is typically preferred. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. However, the determination of dosage ranges and optimal dosages for a particular mammal is also well within the ability of one of ordinary skill in the art having the benefit of the instant disclosure. In certain embodiments, the compounds of this invention can be administered adjunctively with other active compounds such as analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastrointestinal drugs, muscle relaxants, nutritional agents, vitamins, parasympathomimetics, stimulants, antinarcoleptic, and anorectics.

Another embodiment of the present invention relates to a combination therapy comprising the compounds of the invention and one or more compounds that inhibit the serotonin transporter, norepinephrine transporter, or both. The relative proportion of the therapeutic agents in the combination therapy is selected to achieve a specific level of inhibition for the serotonin transporter and the norepinephrine transporter. For example, in certain embodiments it may be beneficial to treat a patient using a combination therapy that inhibits the serotonin transporter and the norepinephrine transporter with equal potency. However, in certain embodiments, it may be beneficial to treat a patient using a combination therapy that inhibits the serotonin transporter to a greater extent than the norepinephrine transporter. For example, in certain embodiments, the ratio of inhibition of the serotonin transporter relative to the norepinephrine transporter is two, four, six, or ten. Alternatively, in certain embodiments, the ratio of inhibition of the norepinephrine transporter relative to the serotonin transporter is two, four, six, or ten. In certain embodiments, the combination therapy comprises two therapeutic agents. However, the combination therapy could include more than two therapeutic agents, e.g. three, four, five, etc.

In certain embodiments, the combination therapy comprises a selective serotonin reuptake inhibitor (SSRI) and compound of formula A or B. In certain embodiments, the combination therapy comprises a selective norepinephrine reuptake inhibitor (SNRI) and compound of formula A or B. In certain embodiments, the combination therapy comprises a SSRI, a SNRI, and a compound of formula A or B. In certain embodiments, the combination therapy comprises at least one of the compounds of the invention, a SSRI, and a SNRI. In certain embodiments, a SNRI is milnacipran.

In certain embodiments, the combination therapy comprises CS1713 and a SSRI. In certain embodiments, the combination therapy comprises CS1713 and a SNRI. In certain embodiments, the combination therapy comprises CS1713, a SSRI, and a SNRI. In certain embodiments, the invention relates to the above-mentioned combination therapies of CS1713 which further comprise CS1814.

In certain embodiments, the combination therapy comprises CS1714 and a SSRI. In certain embodiments, the combination therapy comprises CS1714 and a SNRI. In certain embodiments, the combination therapy comprises CS1714, a SSRI, and a SNRI. In certain embodiments, the invention relates to the above-mentioned combination therapies of CS1714 which further comprise CS1814.

In certain embodiments, the combination therapy comprises CS1814 and a SSRI. In certain embodiments, the combination therapy comprises CS1814 and a SNRI. In certain embodiments, the combination therapy comprises CS1814, a SSRI, and a SNRI.

Combinatorial Libraries

The subject compounds readily lend themselves to preparation using the methods of combinatorial chemistry, providing access to combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the akin linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available akin groups of a peptide library via a photocleavable o-nitrobenzyl linker. This approach is convenient when preparing combinatorial libraries of peptide-like or other akin-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to akin groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Toxicological Assessments

During the drug development process, potential therapeutic agents or drug candidates must be demonstrated to be both safe and effective for their intended use. In drug development processes, potential drug candidates are subjected to toxicology assessments in an effort to demonstrate safety.

In general, following contact of a compound with a population, the effect of the compound on the members of the population is determined. The effect of the compound on the members of the population is generally determined by evaluating one or more of a number of different phenotypic parameters. Phenotypic parameters that are evaluated in a given assay of the subject invention may vary widely depending, at least in part, on the nature of the multi-cellular organisms being employed. Typically, phenotypic parameters that are evaluated in any given assay include one or more of the following: (1) viability; (2) morphological defects; and (3) fecundity. Specific parameters that may be evaluated include one or more of: (1) lethal dose, e.g. $LD_{50}$, $LD_{10}$ etc.); (2) growth defects; (3) sterility effect dose; (4) developmental defects; (5) neurologic impairment; (5) life-span modulation, e.g. life span enhancing or shortening; and the like.

A number of different types of non-mammalian multi-cellular organisms may be employed in toxicological assessments, where these types of organisms include insects, amphibians, fish, and the like. Specific organisms of interest include: Xenopus, Zebrafish, Caenerhabditis, Drosophila and the like. Of particular interest are invertebrate animals, particularly members of the phylum arthropoda, and more particularly members of the class insecta. Of particular interest are flies. For example, flies of the family Drosophilidae, where the animal is often a Drosophila melanogaster. The multi-cellular organisms employed may be at any stage of their life, e.g. in the larval stage, in the adult stage, etc.

For example, a compound is brought into contact with a population of multi-cellular organisms in a manner such that the compound is capable of exerting activity on at least a substantial portion of, if not all of, the individual organisms of the population. By substantial portion is meant at least 40 number %, usually at least 50 number % and more usually at least 60 number %, where the number % may be substantially higher and can be as high as 80, 90 or 95 number % or higher. Generally, each compound is contacted with the members of the population in a manner such that it is internalized by the organisms. Typically internalization will be by ingestion, i.e. orally, such that that each compound will generally be contacted with the plurality of organisms by incorporating the compound in the nutrient medium, e.g. water, aqueous solution of additional nutrient agents, etc., of the organisms. For example, where the multi-cellular organism is a fly, the candidate agent is generally orally administered to the fly by mixing the agent into the fly nutrient medium and placing the medium in the presence of the fly, (either the larva or adult fly, usually the larva) such that the fly feeds on the medium.

In addition to the above parameters, the gene expression levels of the test organisms can be assayed, e.g. gene expression levels in treated larva, pupa, and/or flies can be evaluated. The genes can be from "housekeeping" genes that provide basic metabolic information to developmental and tissue specific genes to gauge which tissue or cell type is affected and when. A variety of different gene expression protocols, including arrays based protocols, are known to those of skill in the art, including those described in: EP 0 328 829 B1 and U.S. Pat. Nos. 5,468,613; 5,580,726; 5,599,672; 5,512,462; 5,162,209 and 5,162,209, the disclosures of which are herein incorporated by reference. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299–304; Nguyen et al., Genomics (1995) 29: 207–216; Pietu et al., Genome Res. (1996) 6: 492–503; and Zhao et al., Gene (1995) 166: 207–213.

The effect of a compound on a particular physical parameter or parameters being evaluated may be determined manually or robotically, such that in many embodiments determination of the effect of the compound on the organism is accomplished via an automated procedure.

The effect of the compound on the phenotypic parameter or parameters is then related to the toxicity of the compound. As such, the effect on the phenotypic parameter(s) is employed to derive a toxicity profile for the assayed compound, where toxicity profile refers to the toxic activity of a given compound, i.e. its collection of one or more toxic activities, such as lethality, sterility causing activity, etc.

Fly Model for Toxicology

A candidate chemical is dissolved in water at or near its saturation point. Serial dilutions of this stock solution are used to rehydrate instant fly media (Fisher Scientific). Specifically, one toxicity assay will comprise of instant fly media rehydrated with pure stock solution of a chemical, while another will be rehydrated with a 10% solution of the chemical (in water). This format will be used to generate data over a 4 to 5 log dose range for each chemical tested.

A known quantity of embryos, typically between 40–50, is used as the input. Specifically, 40 to 50 embryos are counted and placed in the receptacle that contains the media/chemical mixture to be tested. The embryos may be counted manually or by automation (e.g., liquid suspension of embryos flowing through a diode). The larva feed on the media/chemical mixture. All aspects of development from larva stage to adult must proceed normally in the presence of the chemical. The only food and water source available to the larva and flies contains the chemical. It is shown that the variability of and intake amount that can be expected using this protocol by feeding the larva chemicals that are easy to assay. Specifically, iron, copper, and zinc have been selected. Sensitive and accurate kits are commercially available to analyze these chemicals down to a concentration of 1 part per million. This will assign quantitative analyses to determine variability between larva in a test receptacle and between larva in different receptacles.

The developing larva and pupa are examined for normal growth and development. Then the adult flies are analyzed for lethality, sterility, developmental defects, and life span alterations. Lethality is determined by dividing the number of adult flies that enclose by the total number of embryos that were placed in the receptacle. Sterility is examined for both males and females by crossing them to normal flies. A physical examination of the adults reveals any visible defects, such as limb defects, tissue formation defects, abnormal coordination etc. Finally the flies are allowed to live the natural span of their life to determine whether an effect occurred to either shorten or lengthen the average lifespan of the fly.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of CS1590 and CS1591

A 200 mL three neck round bottom flask, equipped with a stir bar, a thermometer and a gas adapter was charged with 4-methoxyphenylacetonitrile (9.38 g, 63.76 mmol) and benzene (70 mL). The reaction mixture was allowed to cool to 0° C. followed by the addition of sodium amide (4.97 g, 127.5 mmol) and stirred an additional 2 hours at this temperature. After this period of time (R)-epichlorhydrine (5.9 g, 63.76 mmol) was added and the resulting reaction mixture was stirred overnight, the solvent was reduced under reduced pressure and the residue was dissolved in ethanol (50 mL) and aqueous potassium hydroxide (1 mol/L, 40 mL). The solution was then heated to reflux overnight followed by addition of concentrated hydrochloric acid to adjust the pH=1. The aqueous phase was extracted with tert.-butylmethylether (200 mL) and ethyl aceate (200 ml). The organic phases were combined, washed with sat. sodium chloride, dried (MgSO4) and the solvent was reduced under reduced pressure to afford crude CS1590 which was purified by column chromatography on silica gel using ethyl acetate/dichloromethane 1:4 as an eluent. The fractions containing the desired product were combined and reduced under reduced pressure to afford CS1590 (5.42 g, 41.7%) as an off white solid.

In a similar fashion the desired enantiomer CS1591 was synthesized.

EXAMPLE 2

Synthesis of CS1608 and CS1609

A 200 mL three neck round bottom flask, equipped with a stir bar, a thermometer and a gas adapter was charged with n-butyllithium (1.6 mol/L, 29.8 mL, 47.7 mmol), cooled to 0° C. followed by the addition of diethylamine (3.49 g, 47.7 mmol). The solution was stirred for 20 min, allowed to cool to −78° C. followed by the addition of a solution of CS1590 (6.08 g, 29.8 mmol) in tetrahydrofuran (50 mL). The reaction mixture was allowed to warm to room temperature overnight, followed by quenching the reaction mixture into an aqueous saturated solution of ammonium chloride (200 ml) and subsequent extraction with ethyl acetate. The organic phase was separated, dried (MgSq4) and the solvent was reduced under reduced pressure to afford crude CS1608 (8.10 g, 98%) which was used without further purification for the next step.

In a similar fashion the desired enantiomer CS1609 was synthesized.

EXAMPLE 3

Synthesis of CS1628 and CS1648

A 200 mL three neck round bottom flask, equipped with a stir bar, a thermometer and a gas adapter was charged with CS1608 (5.6 g, 20.19 mmol) and N,N-dimethylformamide (20 mL), cooled to 0° C., followed by the addition of sodium azide (5.2 g, 80.76 mmol), triethylamine (10.2 g, 100.95 mmol) and methanesulfochloride (4.6 g, 60.57 mmol). The suspension was stirred for 24 hours at room temperature, quenched into water (200 ml-) and extracted with ethylacetate (2×200 mL), dried (MgS04) and the solvent was reduced under reduced pressure to afford crude CS1628, which was purified by column chromatography on silica gel using heptane/ethyl actetate 5:1 as an eluent to afford CS1628 (2.2 g, 36%) as an off white solid.

In a similar fashion the desired enantiomer CS1648 was synthesized.

EXAMPLE 4

Synthesis of CS1649 and CS1658

A 50 mL three neck round bottom flask, equipped with a stir bar, a thermometer and a gas adapter was charged with CS1628 (2.2 g, 7.27 mmol) and dichloromethane (200 mL), cooled to −35° C. followed by the addition of a solution borontribromide in dichloromethane (1.0 mol/L, 21.8 mL, 21.8 mmol). The reaction mixture was kept for 48 h at −28° C., cooled back to −40° C. followed by the addition of methanol. The resulting mixture was poured into water (200 mL), extracted with ethyl acetate (2×200 mL), dried (MgSq4) and the solvent was reduced under reduced pressure to afford crude CS1649, which was purified by column chromatography on silica gel using heptane/ethyl actetate 2:1 as an eluent to afford CS1649 (1.39 g, 66.5 %) as an off white solid.

In a similar fashion the desired enantiomer CS1658 was synthesized.

EXAMPLE 5

Synthesis of CS1665 and CS1710

A 200 mL hydrogenation bottle was charged with CS1649 (1.1 g, 3.81 mmol), methanol (50 ml-) and catalytic amounts of Pd/C. The reaction was subjected to 1 bar of hydrogen pressure until full conversion was observed, the reaction mixture was filtered through a pad of Celite and the solvent removed under reduced pressure to afford crude CS1655, which was purified by column chromataograph on silica gel using dichloromethane/methanol/triethylamine 10:0.5:0.25 as eluent to afford CS1665 (0.80 g, 80%) as an off white solid.

In a similar fashion the desired enantiomer CS1710 was synthesized.

Figure 12:
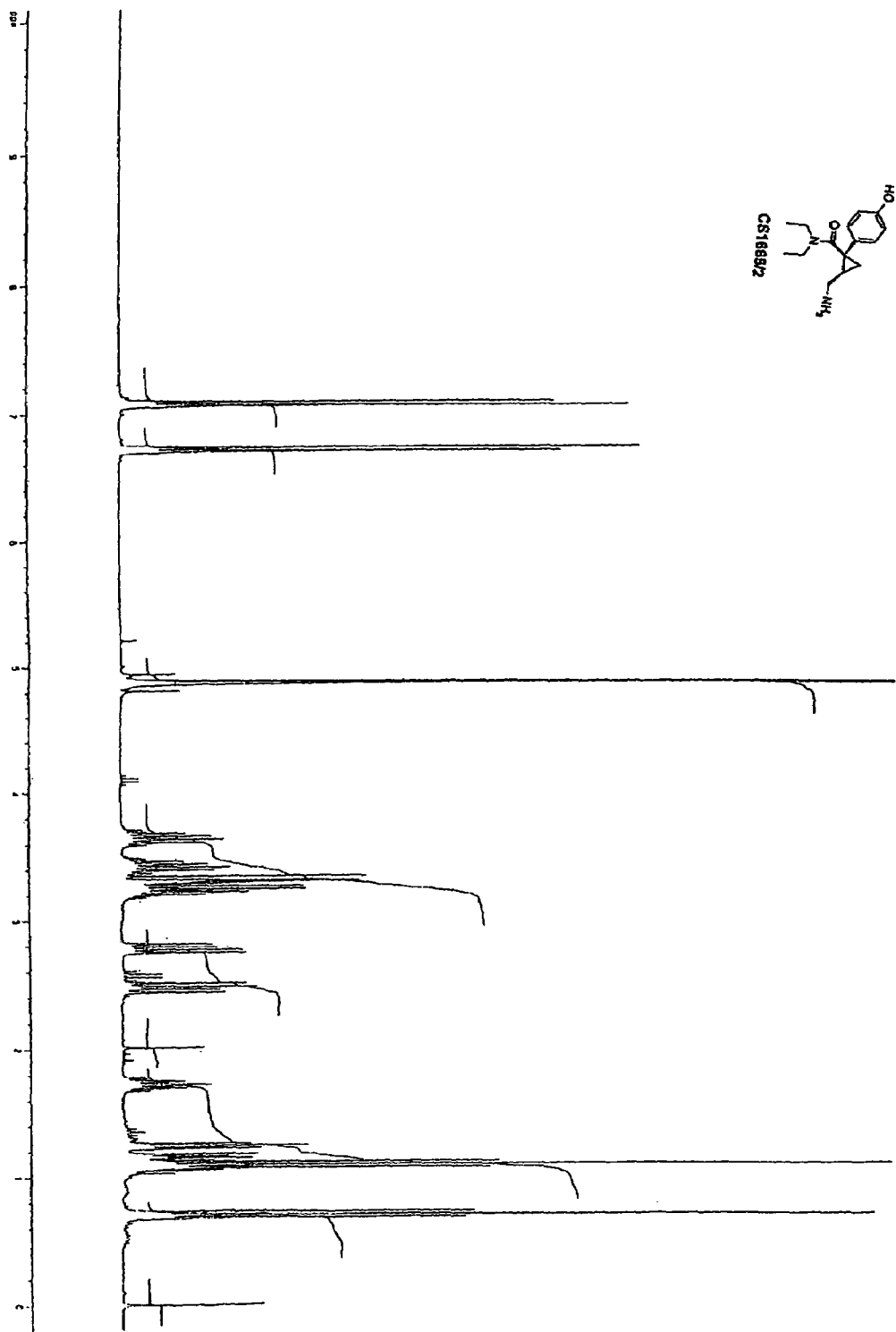
FIG. 12 depicts a $^1$H NMR spectrum of CS1665.
Figure 13:
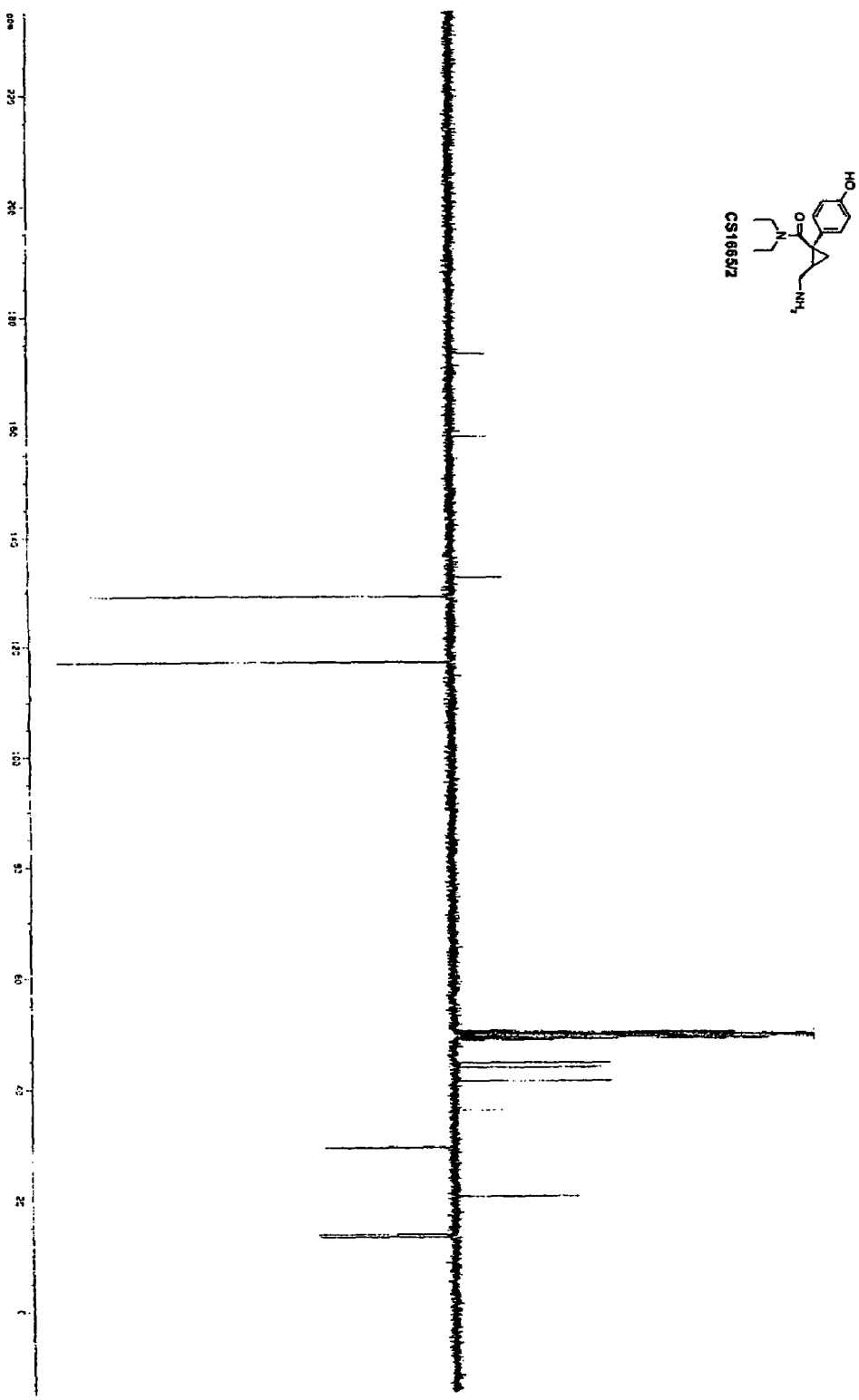
FIG. 13 depicts a $^{13}$C NMR spectrum of CS1665.
Figure 15:
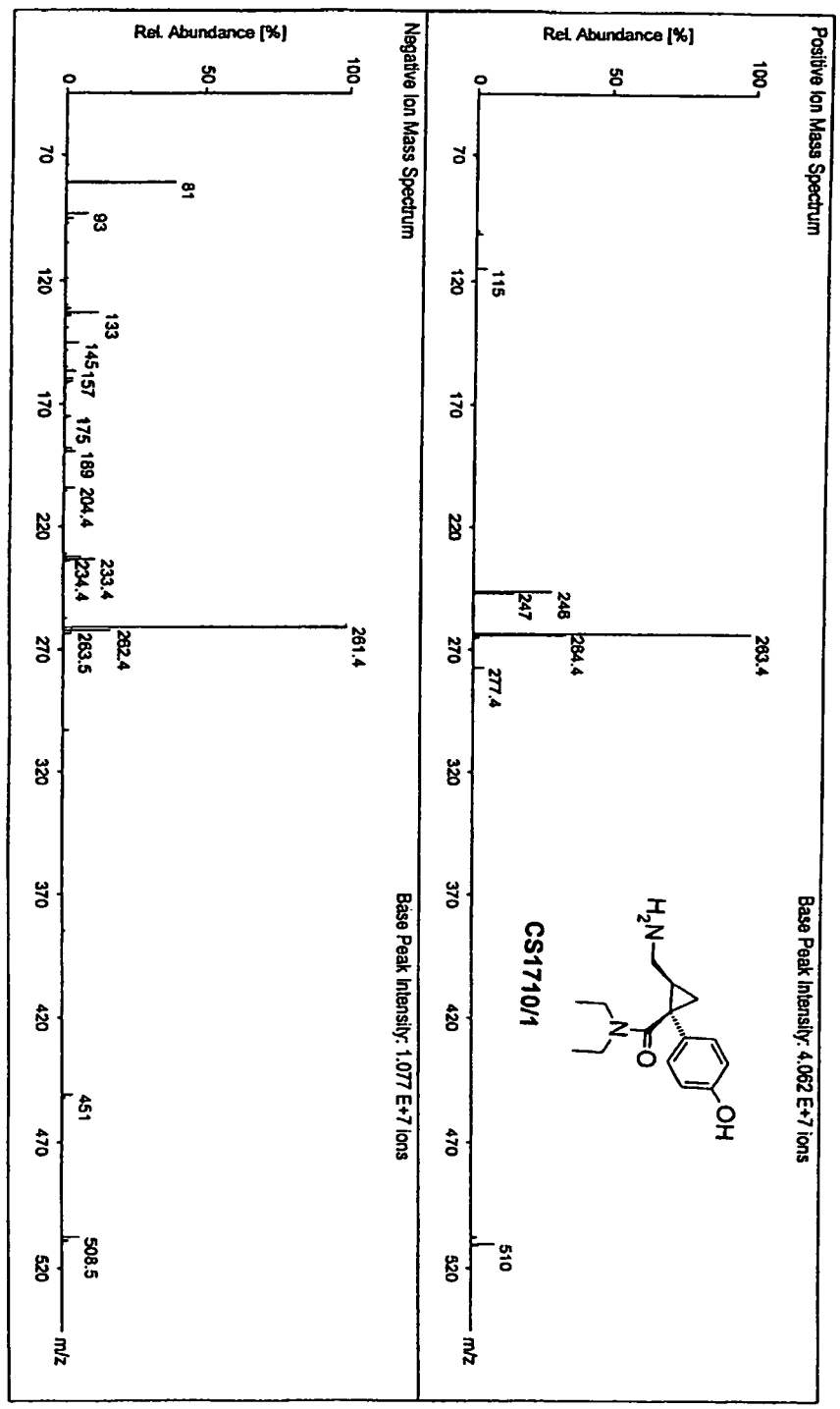
FIG. 15 depicts a mass spectrum of CS1710.

| Analytical Data for CS1665 | |
|---|---|
| Appearance: | Off white solid |
| $^1$H NMR (MeOd-4): | FIG. 12 |
| $^{13}$C{$^1$H} NMR (apt) (MeOd-4): | FIG. 13 |
| Optical Rotation $[a]^{20}_D$ (c 0.5, Methanol): | −89 |
| IR (KBr, Neat, Solvent): | N/A |
| HPLC: | Purity: 97% @ 220 nm, 100% @ 254 nm Method: Gradient of 10% acetonitrile to 95% acetonitrile over 8 min, equilibrate 2 min at 95%, 0.1% TFA, Flowrate: 2.0 mL/min Column: Zorbax XDB-C8 |
| Elemental Analysis: | N/A |
| Mass Spectrum (ESI): | m/z = 263 [$C_{15}H_{22}N_2O_2$ + H]$^+$ |

Figure 16:
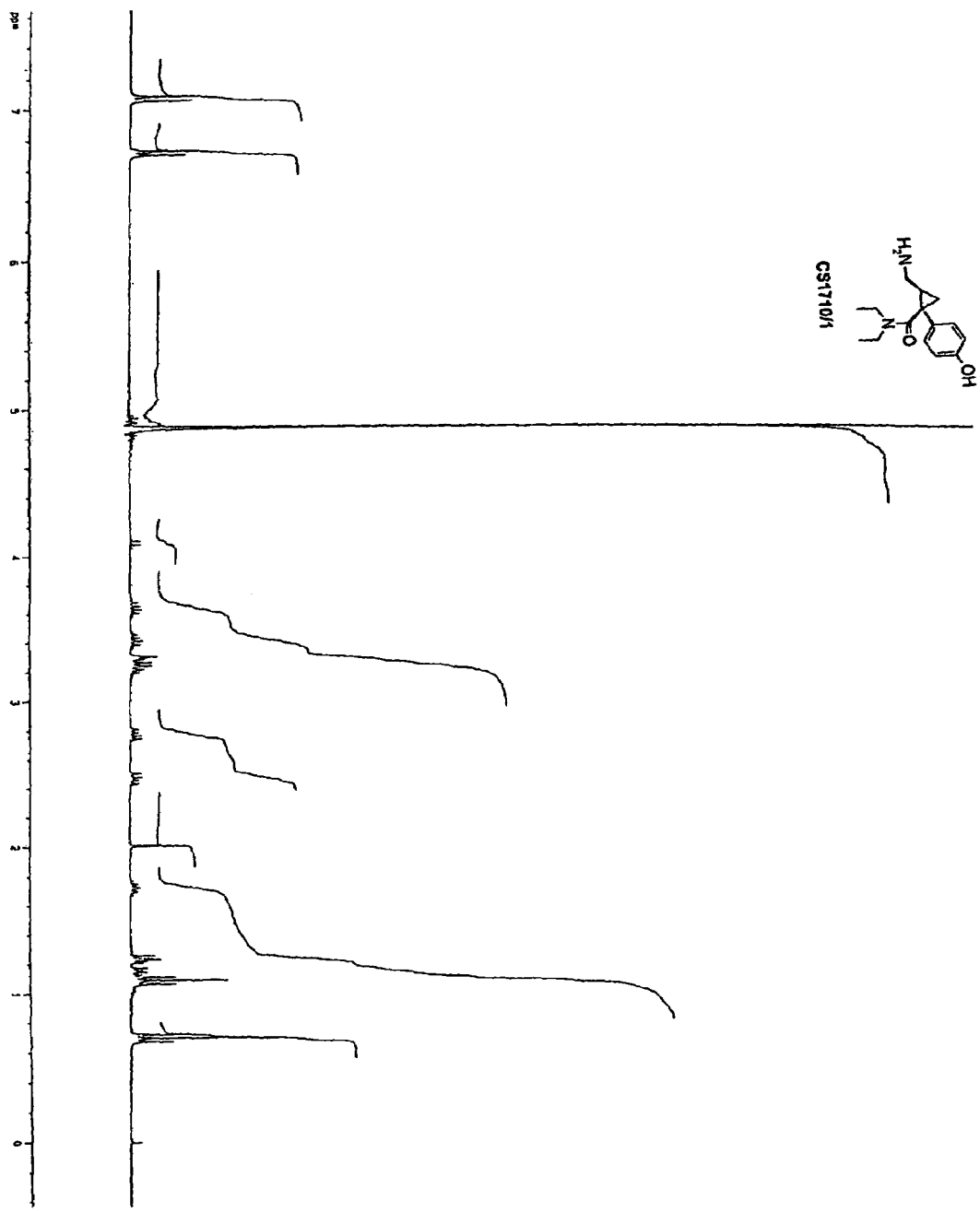
FIG. 16 depicts a $^1$H NMR spectrum of CS1710.
Figure 17:
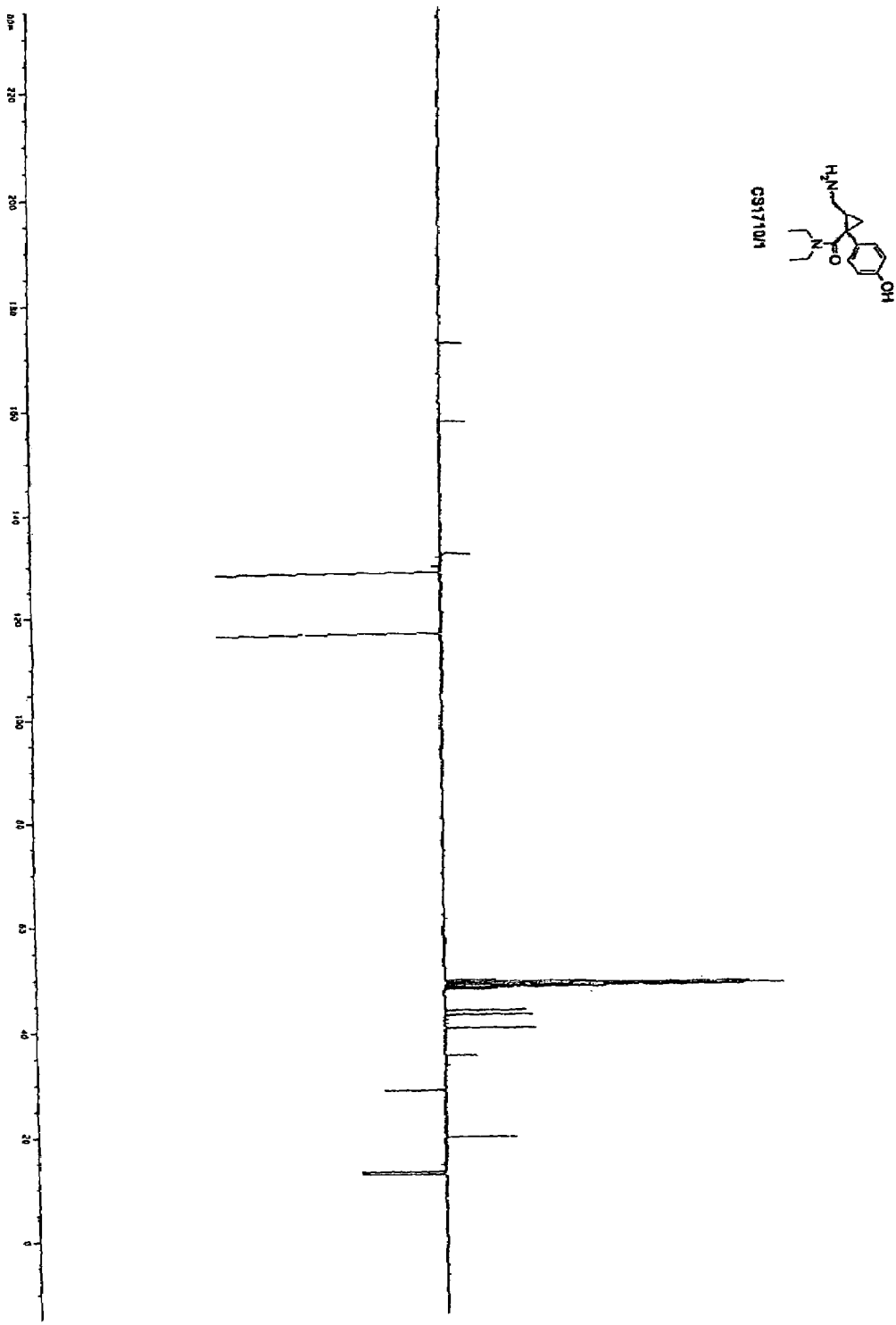
FIG. 17 depicts a $^{13}$C NMR spectrum of CS1710.
Figure 19:
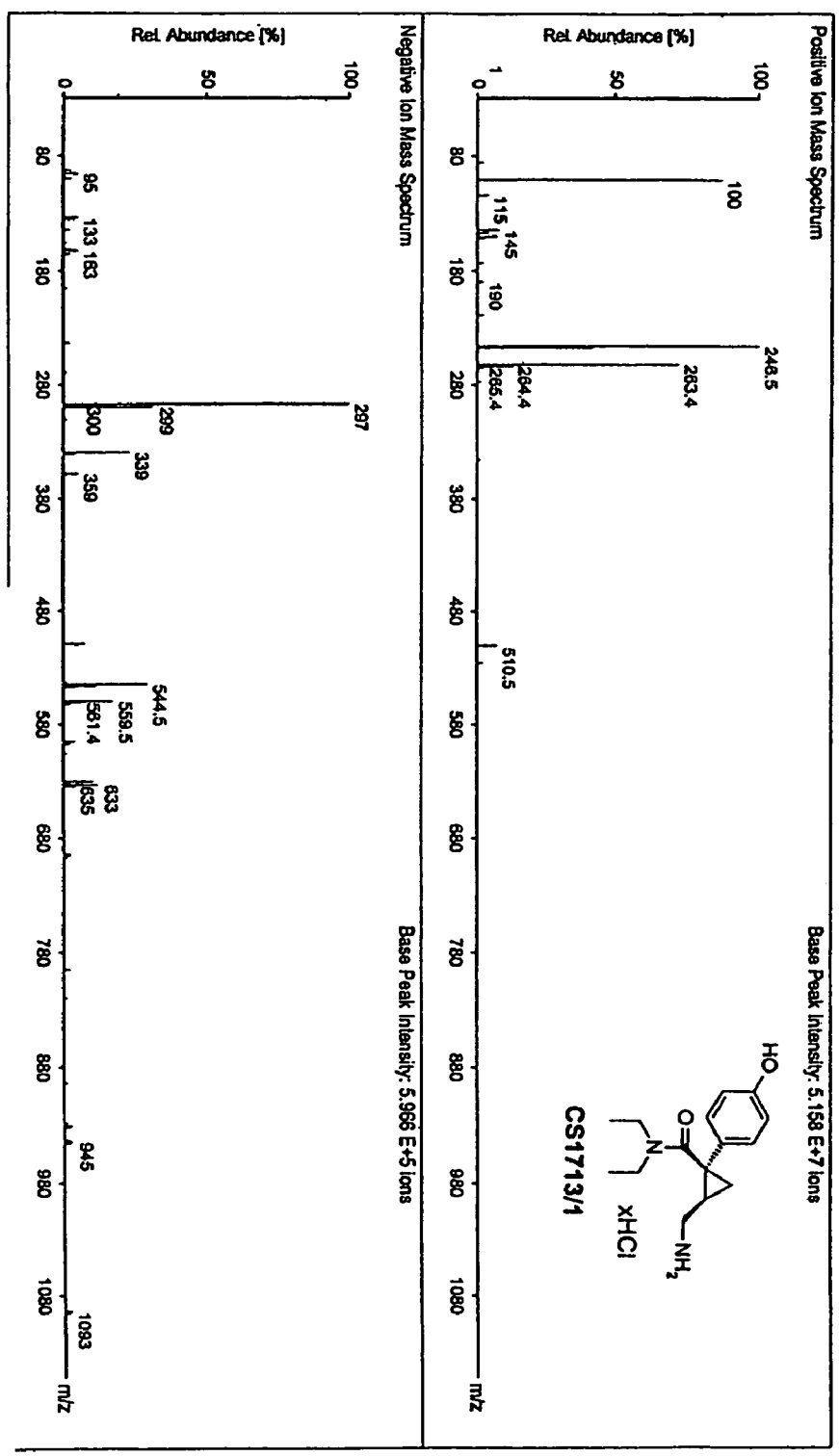
FIG. 19 depicts a mass spectrum of CS1713.

| Analytical Data for CS1710 | |
|---|---|
| Appearance: | Off white solid |
| $^1$H NMR (MeOd-4): | FIG. 16 |
| $^{13}$C{$^1$H}-NMR (apt) (MeOd-4): | FIG. 17 |
| Optical Rotation $[a]^{20}_D$ (c 0.5, Methanol): | +86.2 |
| IR (KBr, Neat, Solvent): | N/A |
| HPLC: | Purity: 98% @ 220 nm, 100% @ 254 nm Method: Gradient of 10% acetonitrile to 95% acetonitrile over 8 min, equilibrate 2 min at 95%, 0.1% TFA, Flowrate: 2.0 mL/min Column: Zorbax XDB-C8 |
| Elemental Analysis: | N/A |
| Mass Spectrum (ESI): | m/z = 263 [$C_{15}H_{22}N_2O_2$ + H]$^+$ |

EXAMPLE 6

Synthesis of CS1713 and CS1714

A 10 mL round bottom flask was charged with CS1665 (0.51 g, 1.71 mmol) and hydrochloric acid in dioxane (5 mol/L, 10 mL). The mixture was stirred for 1 hour at room temperature, followed by removal of the solvent under reduced pressure to afford CS1713 (0.43 g, 84%) as an off white solid.

In a similar fashion the desired enantiomer CS1714 was synthesized.

Figure 20:
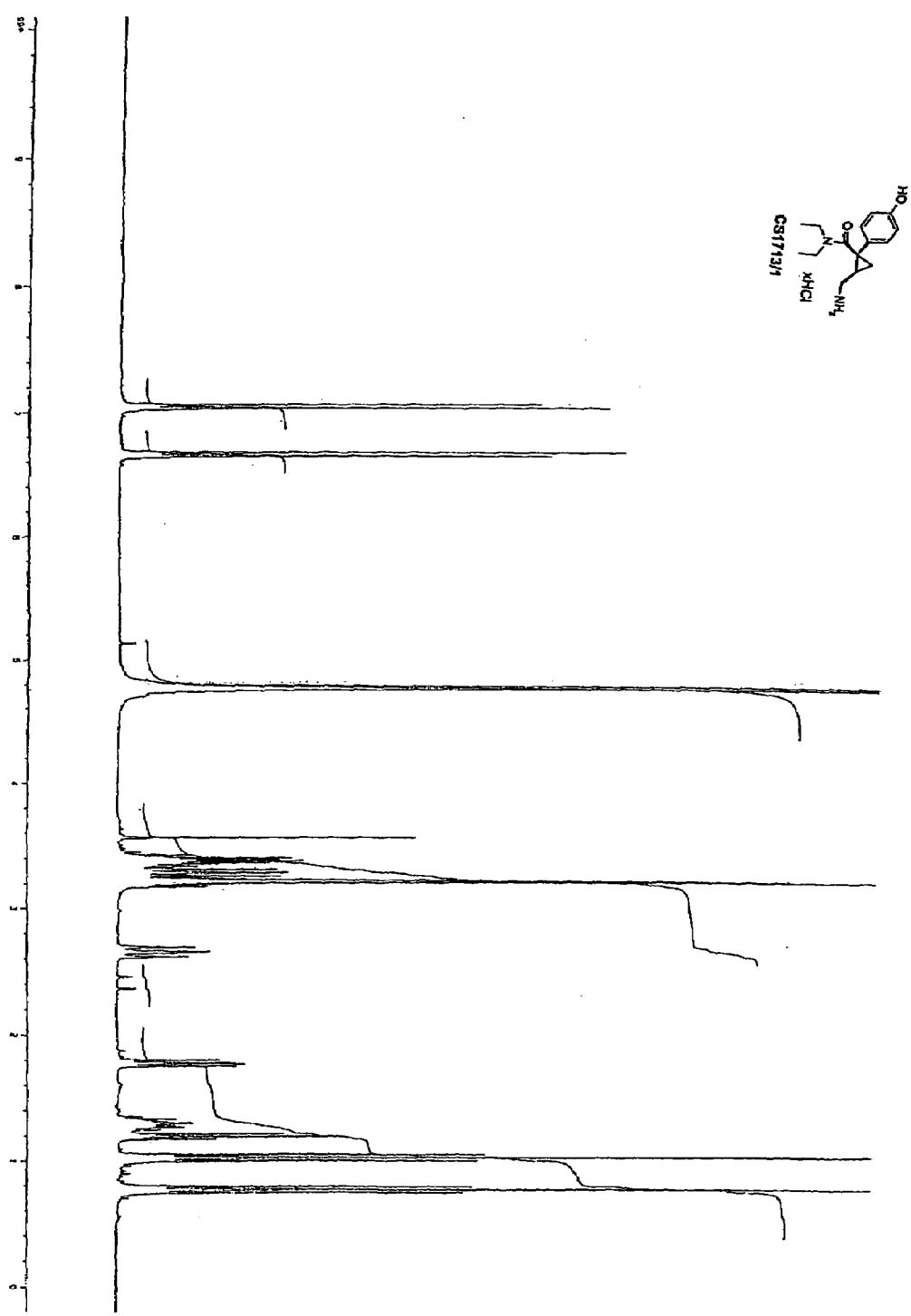
FIG. 20 depicts a $^1$H NMR spectrum of CS1713.
Figure 21:
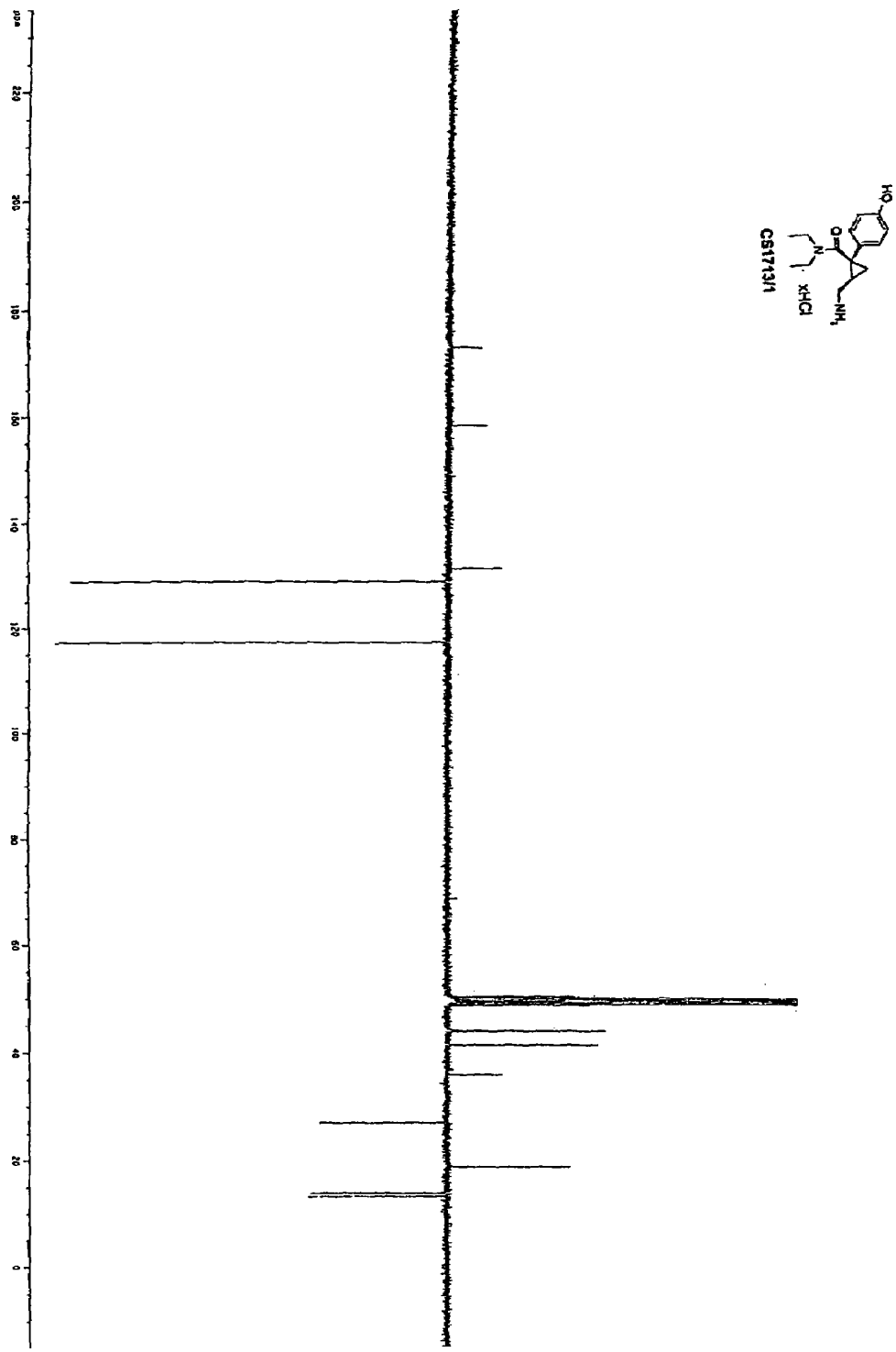
FIG. 21 depicts a $^{13}$C NMR spectrum of CS1713.
Figure 23:
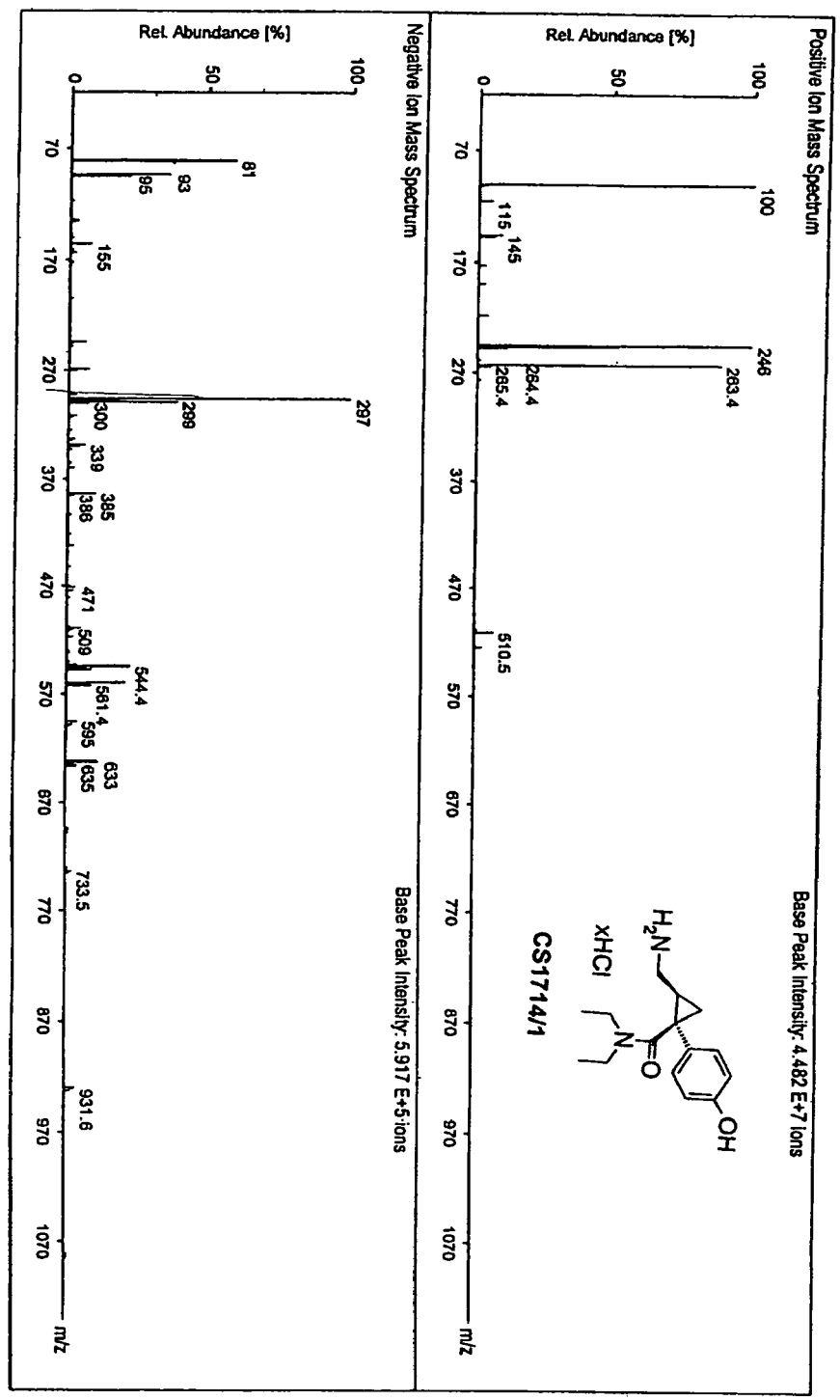
FIG. 23 depicts a mass spectrum of CS1714.

| Analytical Data for CS1713 | |
|---|---|
| Appearance: | Off white solid |
| $^1$H NMR (MeOd-4): | FIG. 20 |
| $^{13}$C{$^1$H}-NMR (apt) (MeOd-4): | FIG. 21 |
| Optical Rotation $[a]^{20}_D$ (c 0.1, Methanol): | +80 |
| IR (KBr, Neat, Solvent): | N/A |
| HPLC: | Purity: 97% @ 220 nm, 98% @ 254 nm Method: Gradient of 10% acetonitrile to 95% acetonitrile over 8 min, equilibrate 2 min at 95%, 0.1% TFA, Flowrate: 2.0 mL/min Column: Zorbax XDB-C8 |
| Elemental Analysis: | N/A |
| Mass Spectrum (ESI): | m/z = 263 [$C_{15}H_{22}N_2O_2$ + H]$^+$ |

Figure 24:
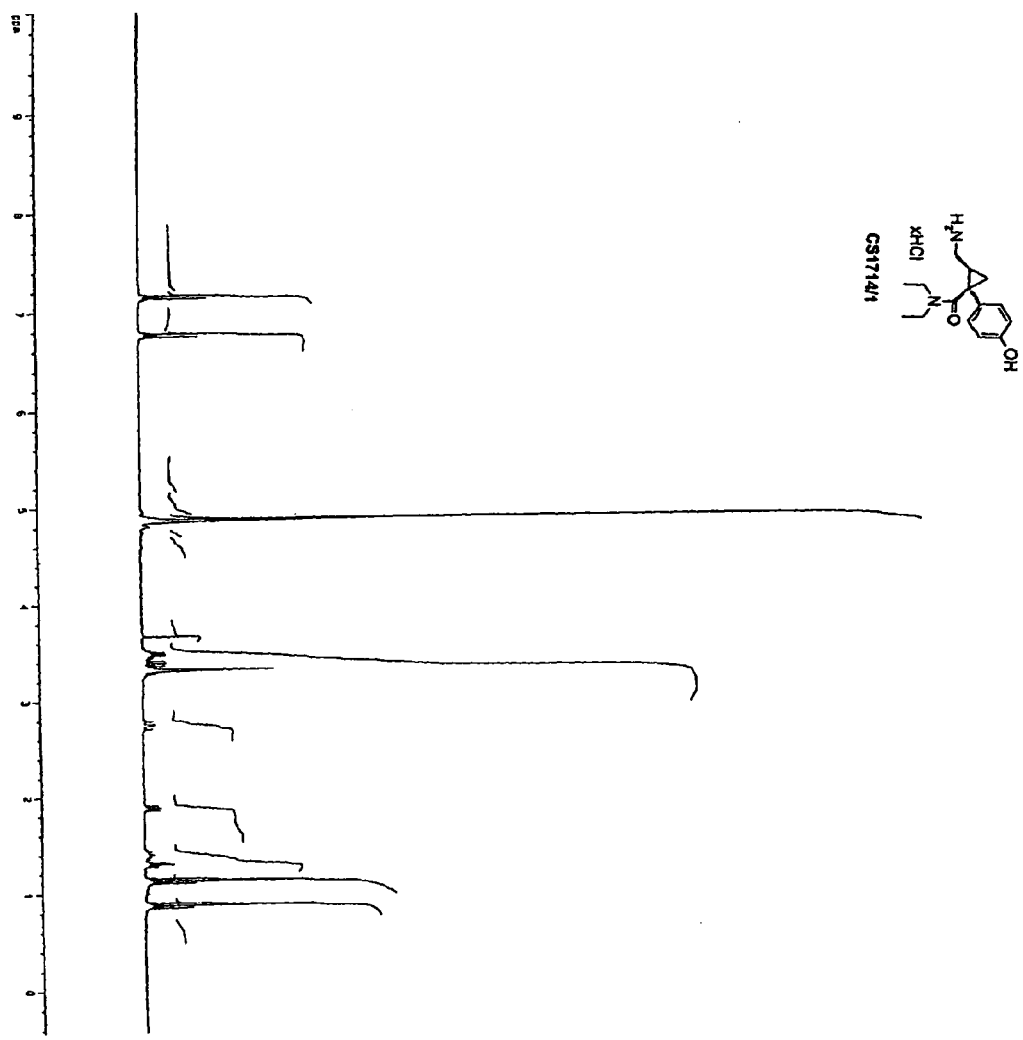
FIG. 24 depicts a $^1$H NMR spectrum of CS1714.
Figure 25:
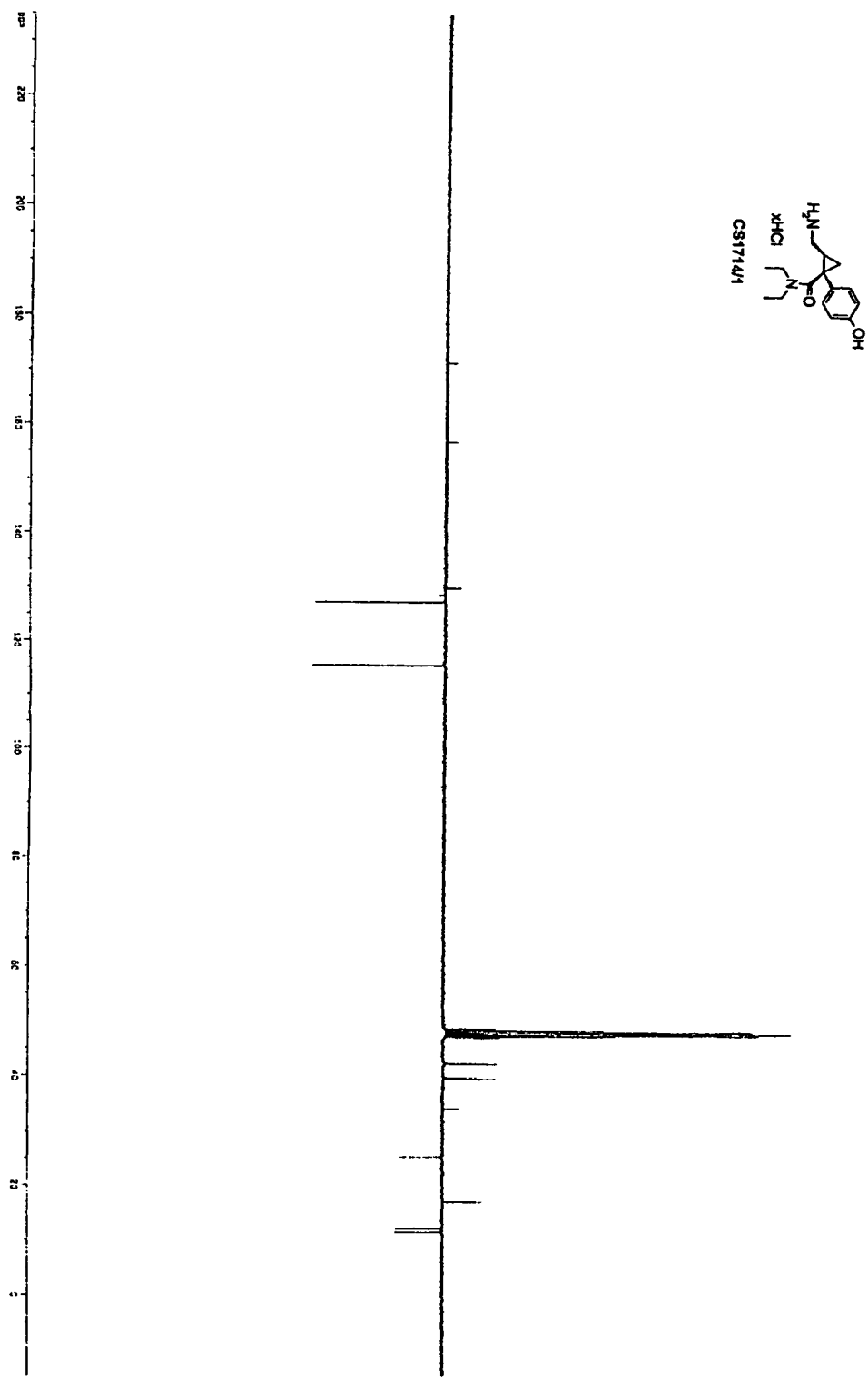
FIG. 25 depicts a $^{13}$C NMR spectrum of CS1714.
Figure 26:
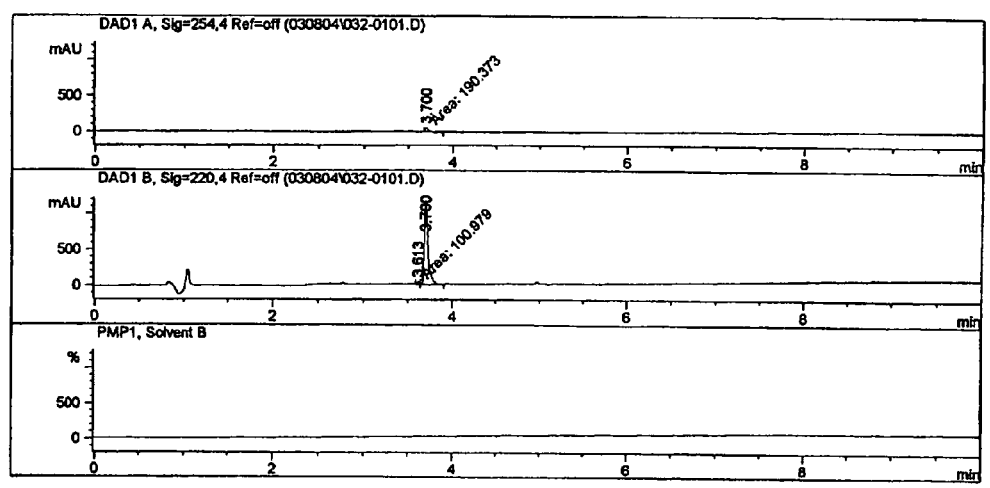
FIG. 26 depicts a HPLC chromatogram of CS1814 (racemic p-Hydroxy-Milnacipran Hydrochloride; HPLC Conditions: 10% to 95% acetonitrile within 8 min; 2 min at 95%, LM with 0.1% TFA, Flow: 2.0 mL/min, Säule: Zorbax XDB-C8).
Figure 27:
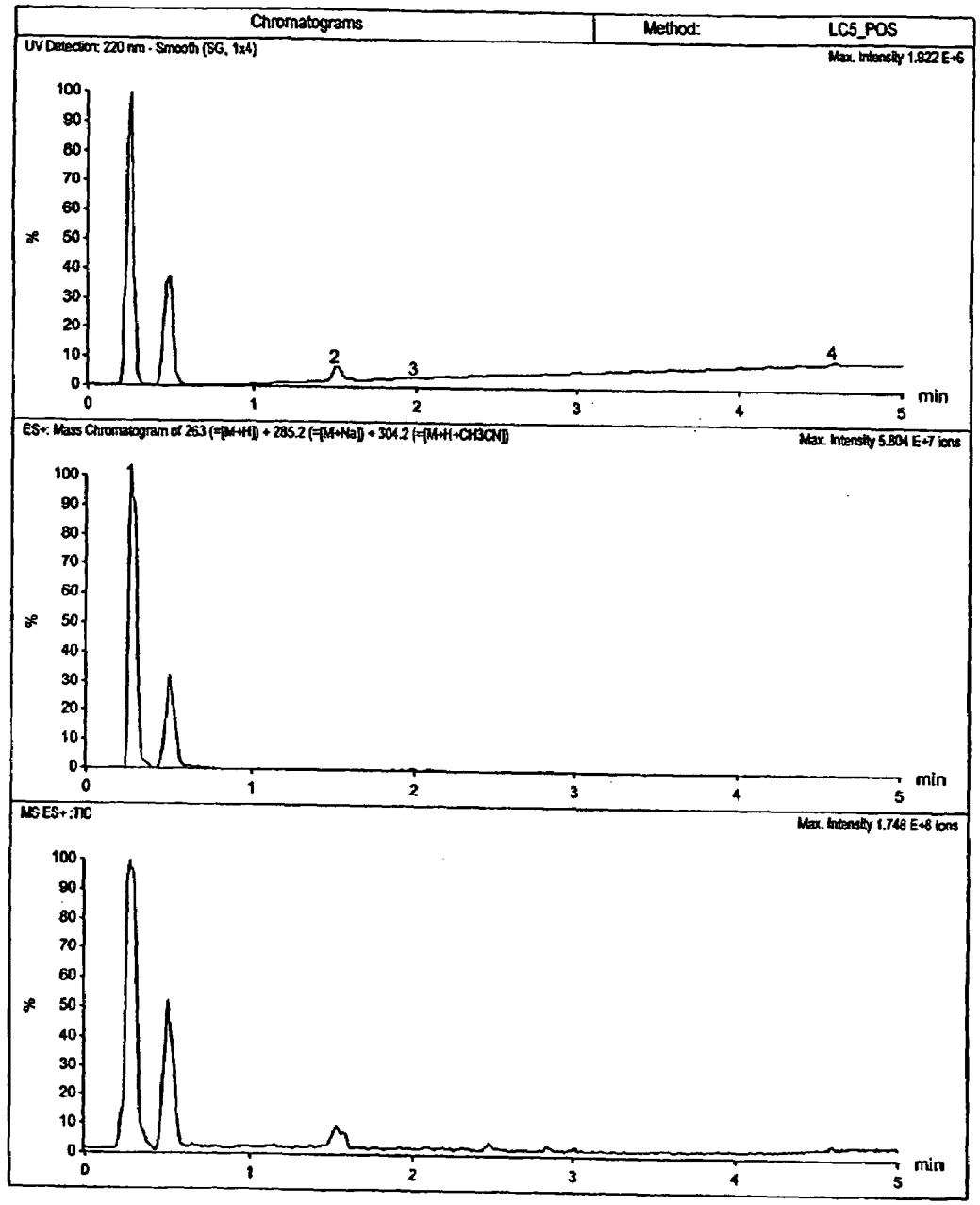
FIG. 27 depicts a LC/MS chromatogram of CS1814.
Figure 28:
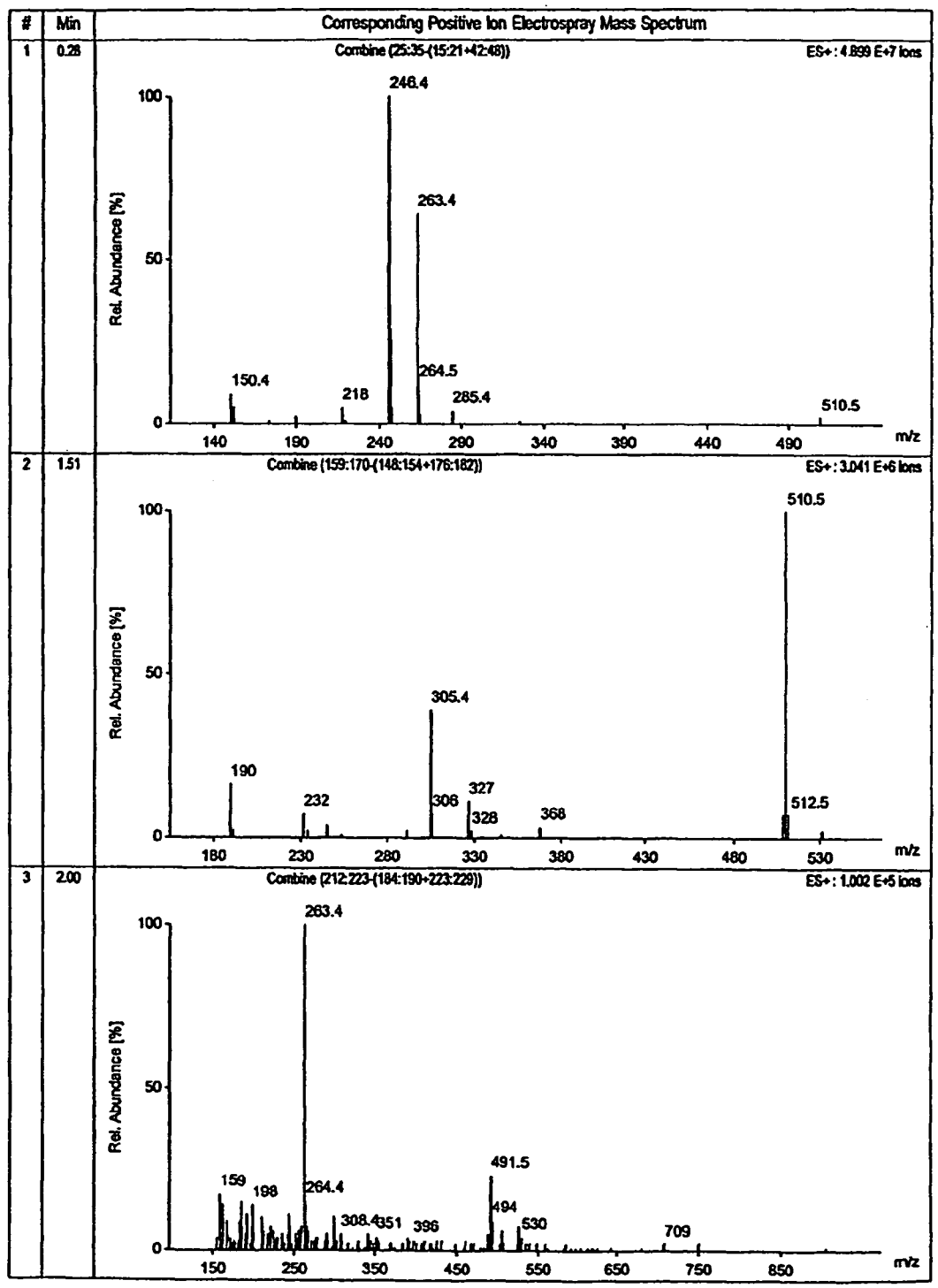
FIG. 28 depicts a mass spectrum of selected peaks from the LC/MS chromatogram of CS1814.
Figure 29:
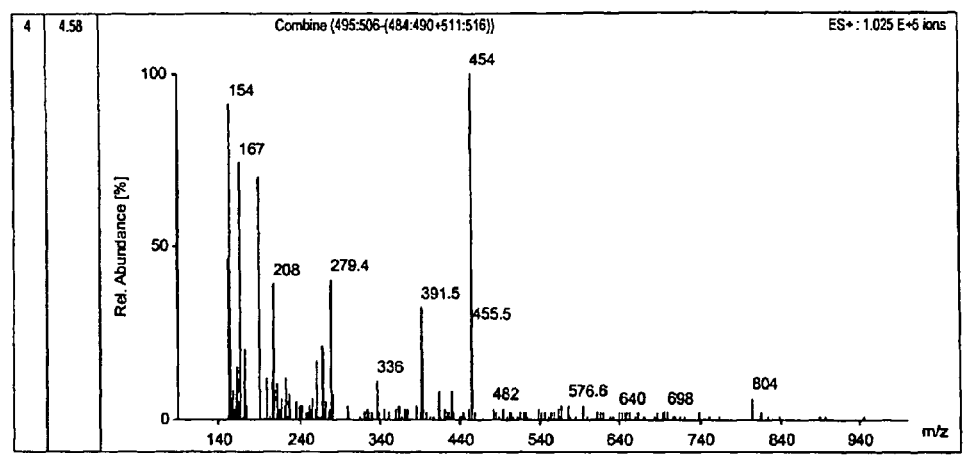
FIG. 29 depicts a mass spectrum of a peak from the LC/MS chromatogram of CS1814.

| Analytical Data for CS1714 | |
|---|---|
| Appearance: | Off white solid |
| $^1$H NMR (MeOd-4): | FIG. 24 |
| $^{13}$C{$^1$H}-NMR (apt) (MeOd-4): | FIG. 25 |
| Optical Rotation $[a]^{20}_D$ (c 0.1, Methanol): | −74 |
| IR (KBr, Neat, Solvent): | N/A |
| HPLC: | Purity: 96% @ 220 nm, 100% @ 254 nm Method: Gradient of 10% acetonitrile to 95% acetonitrile over 8 min, equilibrate 2 min at 95%, 0.1% TFA, Flowrate: 2.0 mL/min Column: Zorbax XDB-C8 |
| Elemental Analysis: | N/A |
| Mass Spectrum (ESI): | m/z = 263 [$C_{15}H_{22}N_2O_2$ + H]$^+$ |

EXAMPLE 7

Preparation of CS1814

A 10 mL flask equipped with a magnetic stir bar was charged with CS1665/2 (120 mg, 0.46 mmol), CS1710/1 (120 mg, 0.46 mmol) and hydochloric acid in dioxan (5 mol/L, 5 ml). The suspension was stirred for 1 hour, reduced under reduced pressure and the residue was again taken up in hydrochloric acid in dioxan (5 mol/L, 1 mL). The suspension was stirred for another hour and reduced under reduced pressure to afford CS1814 (240 mg, quant) as an off white solid. The solid was dissolved in methanol (10 mL, homogenous solution), transferred to a 20 mL round bottom flask and the flask was washed out with additional 5 mL of methanol, combined with the above solution (total volume of approximately 15 mL, homogenous solution) and reduced under reduced pressure to afford CS1814 (240 mg, quant) as an off white solid. The solid was dried under high vacuum. 50 mg of this material were taken and dissolved in methanol (10 ml-) followed by measuring the optical rotation. The solution was later transferred back to the 20 mL flask (homogenous solution) and the solvent removed under reduced pressure.

Figure 30:
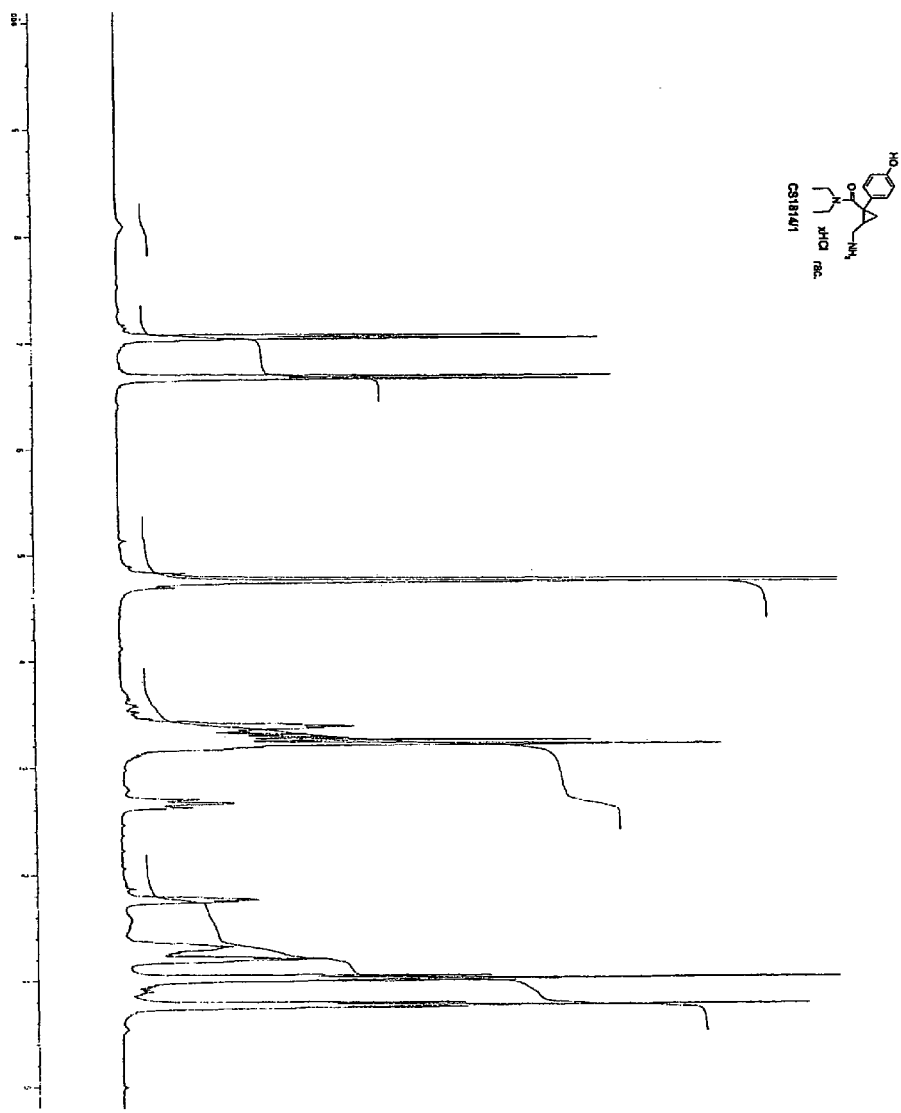
FIG. 30 depicts a $^1$H NMR spectrum of CS1814.
Figure 31:
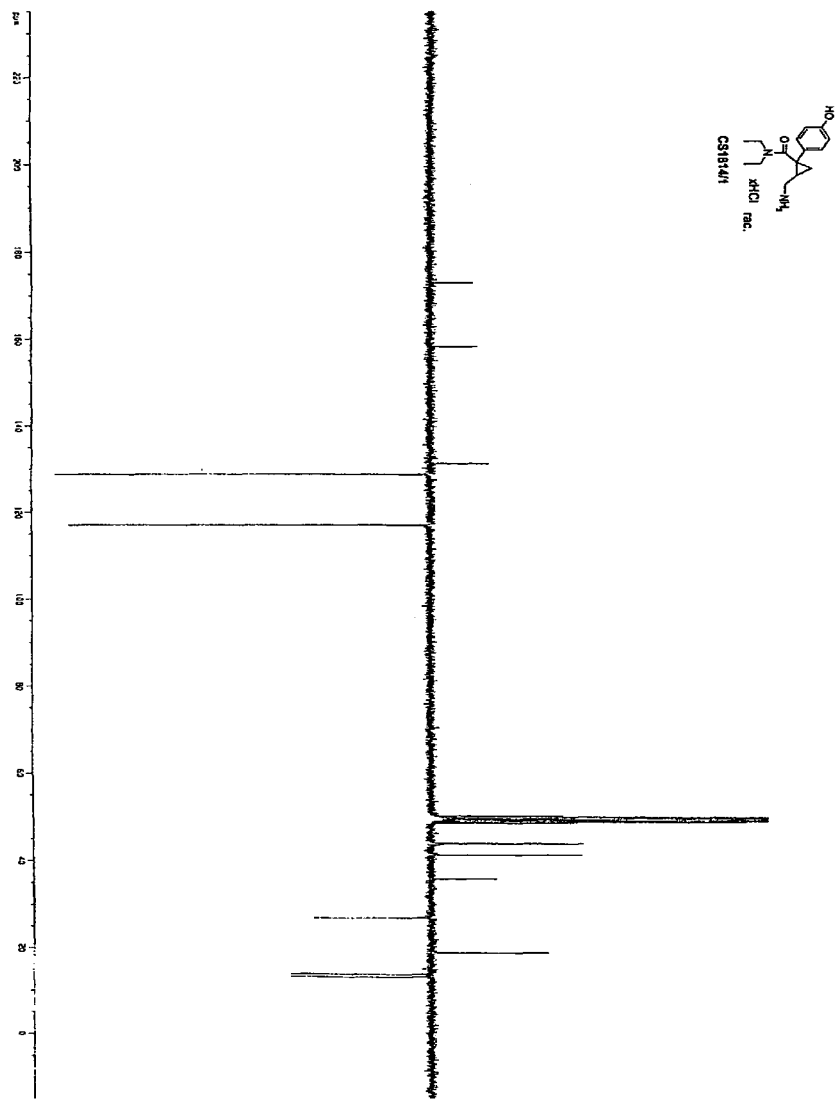
FIG. 31 depicts a $^{13}$C NMR spectrum of CS1814.
Figure 39:
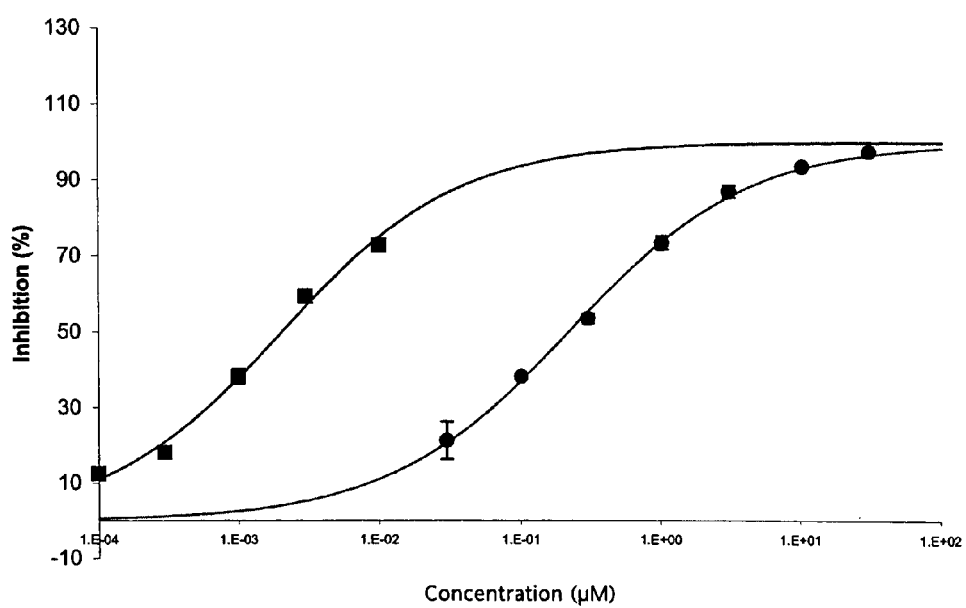
FIG. 39 depicts a graph of % inhibition of Norephinephrine Transporter (NET) by CS1814 (Vial #1).
Figure 40:
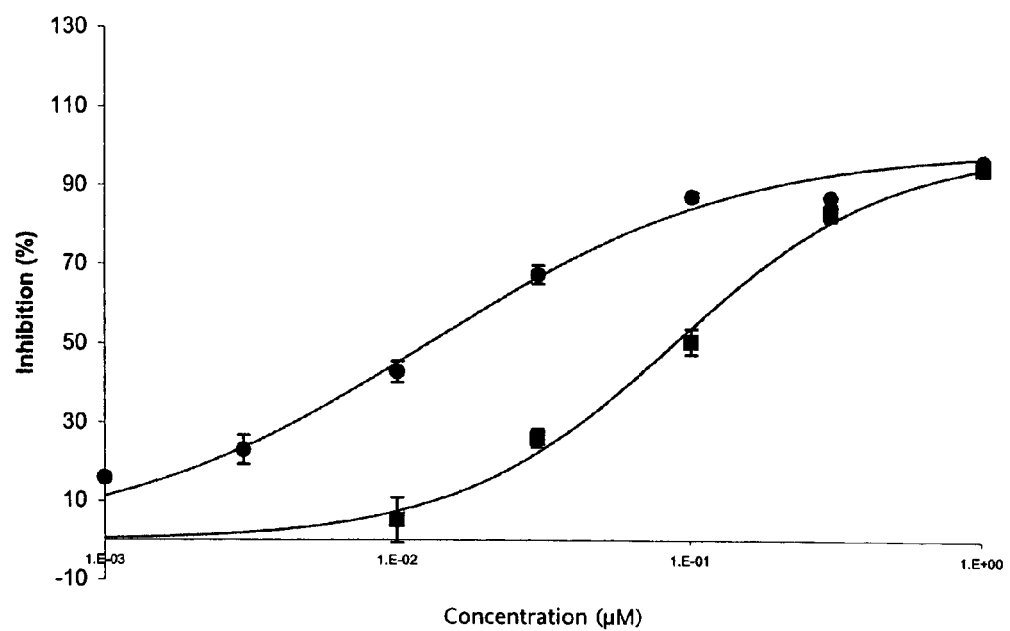
FIG. 40 depicts a graph of % inhibition of Serotonin Transporter (SERT) by CS1814 (Vial #1).
Figure 47:
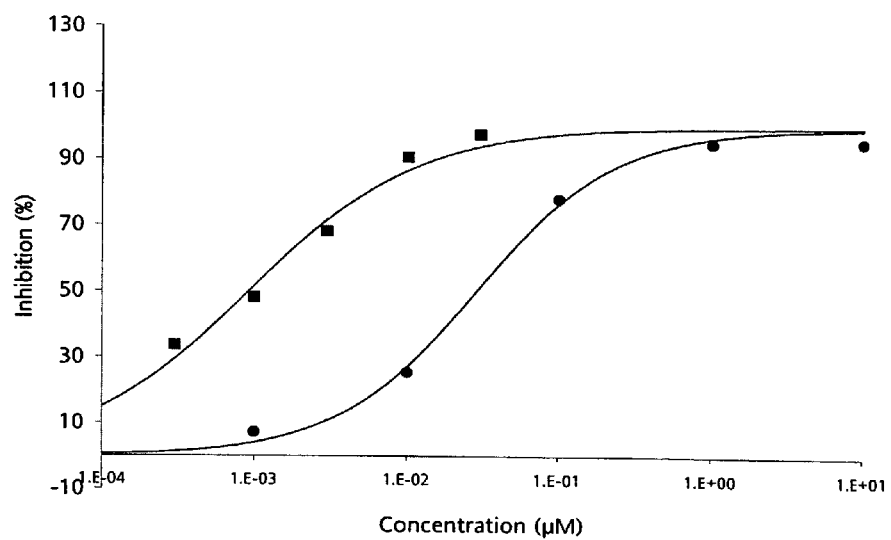
FIG. 47 depicts a graph of % inhibition of Norepinephrine Uptake by CS1814 (CEL-1) and Desipramine.
Figure 48:
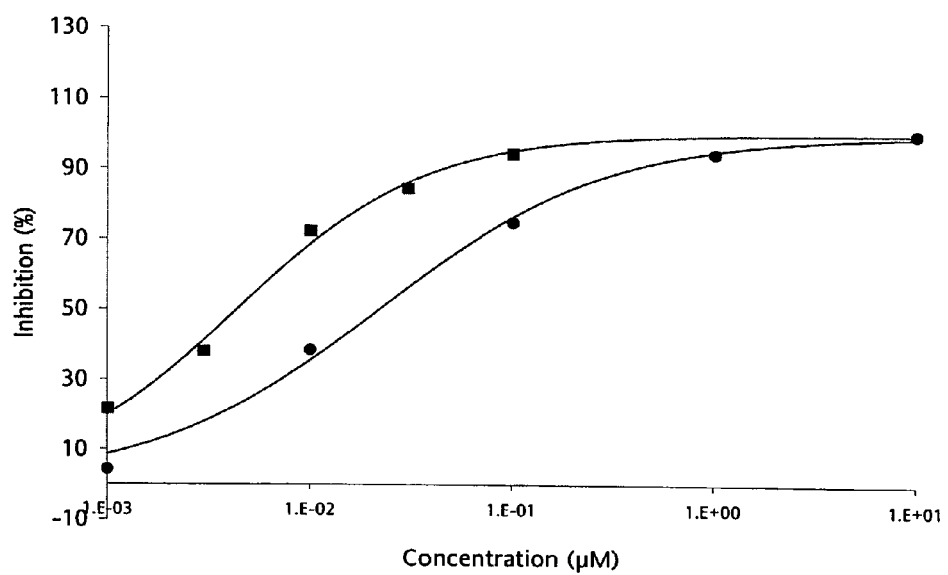
FIG. 48 depicts a graph of % inhibition of Serotonin Uptake by CS1814 (CEL-1) and Fluoxetine.
Figure 49:
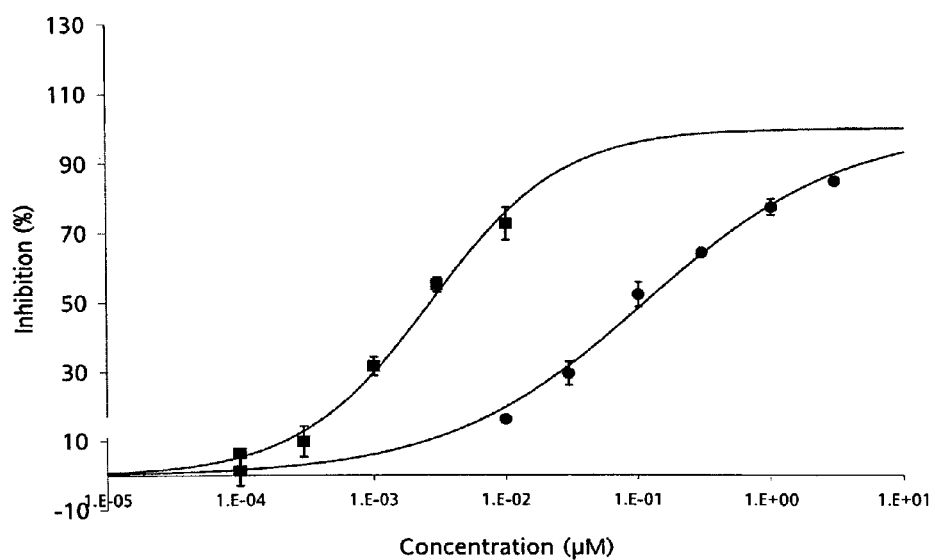
FIG. 49 depicts a graph of % inhibition of Norepinephrine Transporter by CS1713 (CEL-3) and Desipramine.
Figure 50:
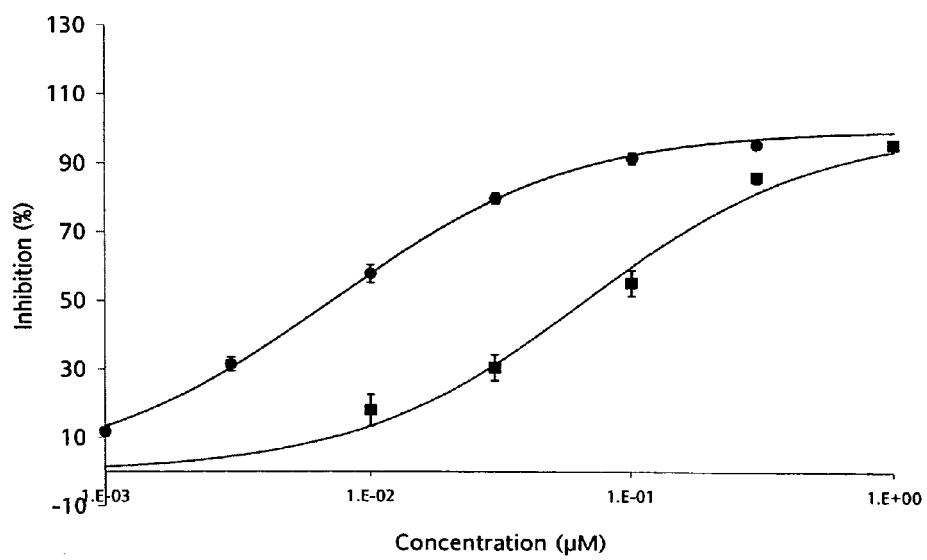
FIG. 50 depicts a graph of % inhibition of Serotonin Transporter by CS1713 (CEL-3) and GBR-12909.
Figure 51:
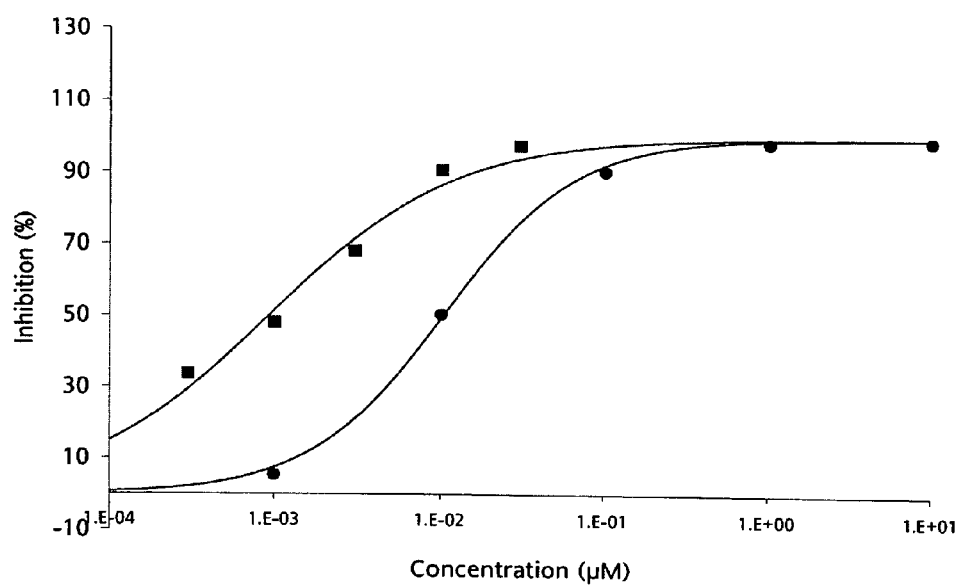
FIG. 51 depicts a graph of % inhibition of Norepinephrine Uptake by CS1713 (CEL- 3) and Desipramine.
Figure 52:
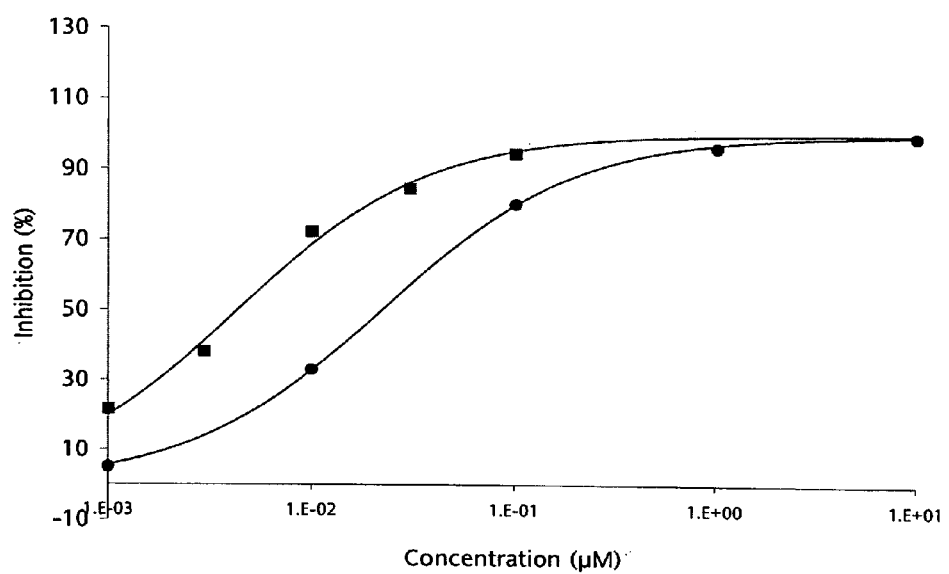
FIG. 52 depicts a graph of % inhibition of Serotonin Uptake by CS1713 (CEL-3) and Fluoxetine.
Figure 53:
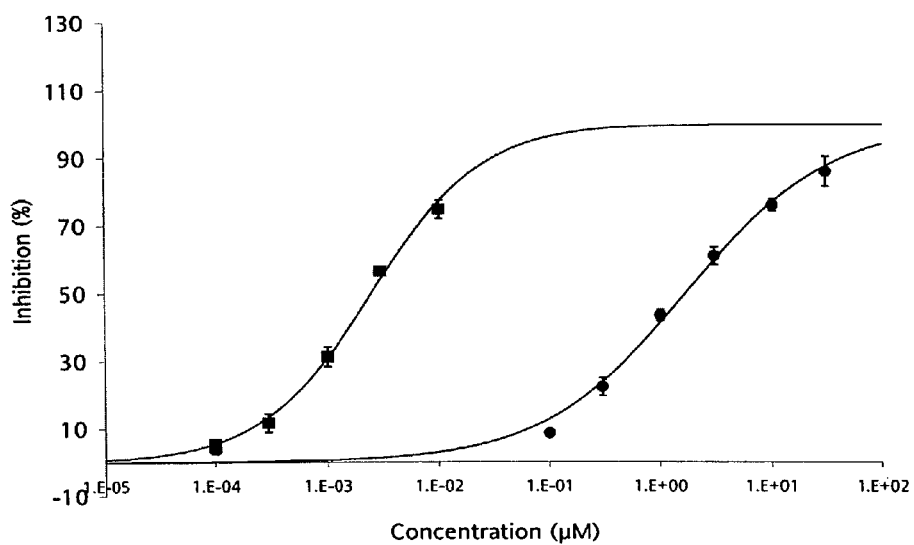
FIG. 53 depicts a graph of % inhibition of Norepinephrine Transporter by CS1714 (CEL-5) and Desipramine.
Figure 54:
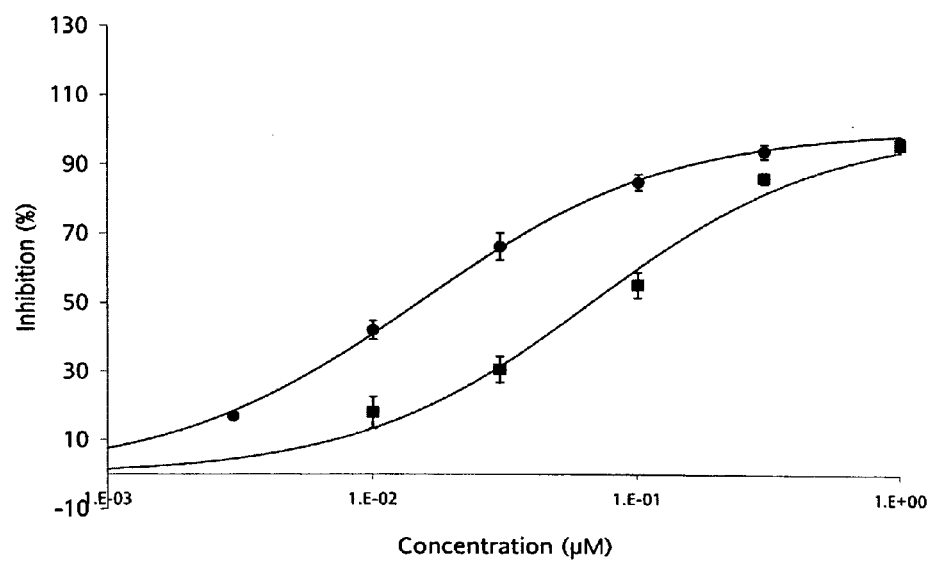
FIG. 54 depicts a graph of % inhibition of Serotonin Transporter by CS1714 (CEL-5) and GBR-12909.
Figure 55:
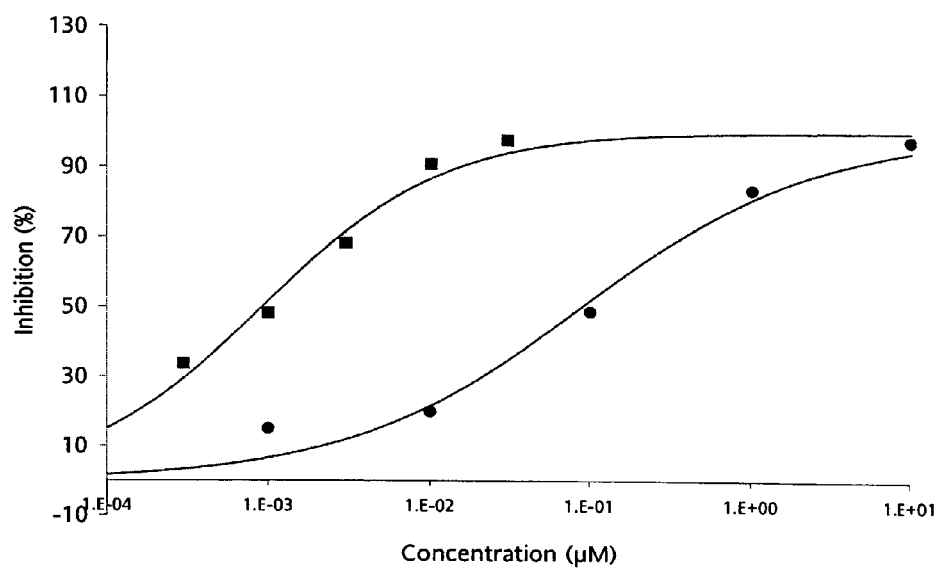
FIG. 55 depicts a graph of % inhibition of Norepinephrine Uptake by CS1714 (CEL-5) and Desipramine.
Figure 56:
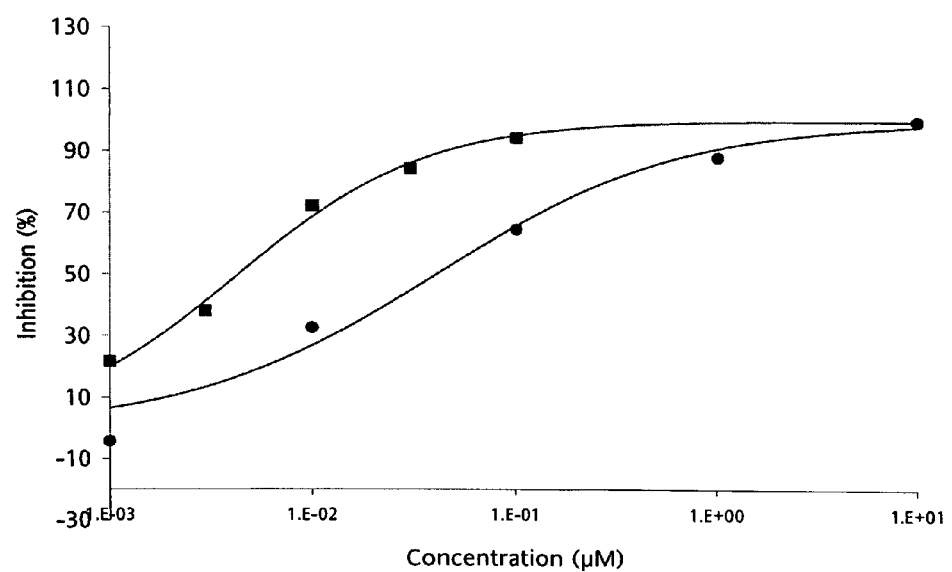
FIG. 56 depicts a graph of % inhibition of Serotonin Uptake by CS1714 (CEL-5) and Fluoxetine.

| Analytical Data for CS1814 | |
|---|---|
| Appearance: | Off white solid |
| $^1$H NMR (MeOd-4): | FIG. 30 |
| $^{13}$C{$^1$H}-NMR (apt) (MeOd-4): | FIG. 31 |
| Optical Rotation $[a]^{20}{}_D$ (c 0.5, Methanol): | 0 racemic |
| IR (KBr, Neat, Solvent): | N/A |
| HPLC: | Purity: 97% @ 220 nm, 98% @ 254 nm Method: Gradient of 10% acetonitrile to 95% acetonitrile over 8 min, equilibrate 2 min at 95%, 0.1% TFA, Flowrate: 2.0 mL/min Column: Zorbax XDB-C8 |
| Elemental Analysis: | N/A |
| Mass Spectrum (ESI): | m/z = 263 [$C_{15}H_{22}N_2O_2$ + H]$^+$ |

EXAMPLE 8

Biological Testing of CS1814 and Reference Compounds

The results from the biological testing of CS1814 and various reference compounds are presented in FIGS. 32–40 and 59. The data in FIG. 59 indicate that CS1814 has an $IC_{50}=0.22$ μM for inhibition of norepinephrine transporter and an $IC_{50}$ value of 12.7 nM for inhibition of serotonin transporter. The binding constants for CS1814 are Ki=0.218 μM for norepinephrine transporter and Ki=6.73 nM for serotonin transporter.

The methods employed in this study have been adapted from the scientific literature to maximize reliability and reproducibility. Reference standards were run as an integral part of each assay to ensure the validity of the results obtained. Assays were performed under conditions as described below. Literature reference(s) for each assay are tabulated below and hereby incorporated by reference.

Where presented, $IC_{50}$ values were determined by a non-linear, least squares regression analysis using Data Analysis ToolboX™ (MDL Information Systems, San Leandro, Calif., USA). Where inhibition constants ($K_i$) are presented, the $K_i$ values were calculated using the equation of Cheng and Prusoff(Cheng, Y., Prusoff, W. H., Biochem. Pharmacol. 22:30993108, 1973) using the observed $IC_{50}$ of the tested compound, the concentration of radioligand employed in the assay, and the historical values for the $K_d$ of the ligand (obtained experimentally at MDS Pharma Services). Where presented, the Hill coefficient ($n_H$), defining the slope of the competitive binding curve, was calculated using Data Analysis Toolbox™. Hill coefficients significantly different than 1.0, may suggest that the binding displacement does not follow the laws of mass action with a single binding site. Where $IC_{50}$, $K_i$, and/or $n_H$ data are presented without Standard Error of the Mean (SEM), data are insufficient to be quantitative, and the values presented ($K_i$, $IC_{50}$, $n_H$) should be interpreted with caution.

Methods:

| 118050 CYP450, 1A2 | |
|---|---|
| Source: | Human recombinant Sf9 insect cells |
| Substrate: | 5 μM 3-Cyano-7-ethoxycoumarin |
| Vehicle: | 0.1% DMSO |
| Pre-Incubation Time/Temp: | None |
| Incubation Time/Temp: | 30 minutes @ 37° C. |
| Incubation Buffer: | 75 mM Potassium Phosphate buffer, pH 7.5 |
| Quantitation Method: | Spectrofluorimetric quantitation of 3-Cyano-7-hydroxycoumarin |
| Significance Criteria: | ≧50% of max stimulation or inhibition |

| 118060 CYP450, 2C9 | |
|---|---|
| Source: | Human recombinant Sf9 insect cells |
| Substrate: | 25 μM 3-Cyano-7-ethoxycoumarin |
| Vehicle: | 0.1% DMSO |
| Pre-Incubation Time/Temp: | None |
| Incubation Time/Temp: | 45 minutes @ 37° C. |
| Incubation Buffer: | 75 mM Potassium Phosphate buffer, pH 7.5 |
| Quantitation Method: | Spectrofluorimetric quantitation of 3-Cyano-7-hydroxycoumarin |

| 118070 CYP450, 2C19 | |
|---|---|
| Source: | Human recombinant Sf9 insect cells |
| Substrate: | 25 μM 3-Cyano-7-ethoxycoumarin |
| Vehicle: | 0.1% DMSO |
| Pre-Incubation Time/Temp: | None |
| Incubation Time/Temp: | 45 minutes @ 37° C. |
| Incubation Buffer: | 75 mM Potassium Phosphate buffer, pH 7.5 |
| Quantitation Method: | Spectrofluorimetric quantitation of 3-Cyano-7-hydroxycoumarin |
| Significance Criteria: | ≧50% of max stimulation or inhibition |

| 118080 CYP450, 2D6 | |
|---|---|
| Source: | Human recombinant Sf9 insect cells |
| Substrate: | 50 μM 3-Cyano-7-ethoxycoumarin |
| Vehicle: | 0.1% DMSO |
| Pre-Incubation Time/Temp: | None |
| Incubation Time/Temp: | 45 minutes @ 37° C. |
| Incubation Buffer: | 75 mM Potassium Phosphate buffer, pH 7.5 |
| Quantitation Method: | Spectrofluorimetric quantitation of 3-Cyano-7-hydroxycoumarin |

| | | | |
|---|---|---|---|
| Significance Criteria: | ≧50% of max stimulation or inhibition | Significance Criteria: | ≧50% of max stimulation or inhibition |

118090 CYP450, 3A4

| | |
|---|---|
| Source: | Human recombinant Sf9 insect cells |
| Substrate: | 50 µM 7-benzyloxy-4-(trifluoromethyl)-coumarin |
| Vehicle: | 0.1% DMSO |
| Pre-Incubation Time/Temp: | None |
| Incubation Time/Temp: | 30 minutes @ 37° C. |
| Incubation Buffer: | 75 mM Potassium Phosphate buffer, pH 7.5 |
| Quantitation Method: | Spectrofluorimetric quantitation of 7-Hydroxy-4-(trifluoromethyl)-coumarin |
| Significance Criteria: | ≧50% of max stimulation or inhibition |

200510 Adenosine $A_1$

| | |
|---|---|
| Source: | Human recombinant CHO cells |
| Ligand: | 1 nM [$^3$H] DPCPX |
| Vehicle: | 1% DMSO |
| Incubation Time/Temp: | 90 minutes @ 25° C. |
| Incubation Buffer: | 20 mM HEPES pH 7.4, 10 mM $MgCl_2$, 100 mM NaCl |
| NonSpecific Ligand: | 100 µM R(−)-PIA |
| $K_d$: | 1.4 nM* |
| $B_{max}$: | 2.7 pmole/mg Protein* |
| Specific Binding: | 85%* |
| Quantitation Method: | Radioligand Binding |
| Significance Criteria: | ≧50% of max stimulation or inhibition |

200610 Adenosine $A_{2A}$

| | |
|---|---|
| Source: | Human recombinant HEK-293 cells |
| Ligand: | 0.05 µM [$^3$H] CGS-21680 |
| Vehicle: | 1% DMSO |
| Incubation Time/Temp: | 90 minutes @ 25° C. |
| Incubation Buffer: | 50 mM Tris-HCl, pH 7.4, 10 mM $MgCl_2$, 1 mM EDTA, 2 U/mL Adenosine Deaminase |
| NonSpecific Ligand: | 50 µM NECA |
| $K_d$: | 0.064 µM* |
| $B_{max}$: | 7 pmole/mg Protein* |
| Specific Binding: | 85%* |
| Quantitation Method: | Radioligand Binding |
| Significance Criteria: | ≧50% of max stimulation or inhibition |

203100 Adrenergic $\alpha_{1A}$

| | |
|---|---|
| Source: | Wistar Rat submaxillary gland |
| Ligand: | 0.25 nM [$^3$H] Prazosin |
| Vehicle: | 1% DMSO |
| Incubation Time/Temp: | 60 minutes @ 25° C. |
| Incubation Buffer: | 50 mM Tris-HCl, 0.5 mM EDTA, pH 7.4 |
| NonSpecific Ligand: | 10 µM Phentolamine |
| $K_d$: | 0.17 nM* |
| $B_{max}$: | 0.18 pmole/mg Protein* |
| Specific Binding: | 90%* |
| Quantitation Method: | Radioligand Binding |
| Significance Criteria: | ≧50% of max stimulation or inhibition |

203200 Adrenergic $\alpha_{1B}$

| | |
|---|---|
| Source: | Wistar Rat liver |
| Ligand: | 0.25 nM [$^3$H] Prazosin |
| Vehicle: | 1% DMSO |
| Incubation Time/Temp: | 60 minutes @ 25° C. |
| Incubation Buffer: | 50 mM Tris-HCl, 0.5 mM EDTA, pH 7.4 |
| NonSpecific Ligand: | 10 µM Phentolamine |
| $K_d$: | 0.31 nM* |
| $B_{max}$: | 0.18 pmole/mg Protein* |
| Specific Binding: | 90%* |
| Quantitation Method: | Radioligand Binding |
| Significance Criteria: | ≧50% of max stimulation or inhibition |

203400 Adrenergic $\alpha_{1D}$

| | |
|---|---|
| Source: | Human recombinant HEK-293 cells |
| Ligand: | 0.6 nM [$^3$H] Prazosin |
| Vehicle: | 1% DMSO |
| Incubation Time/Temp: | 60 minutes @ 25° C. |
| Incubation Buffer: | 50 mM Tris-HCl |
| NonSpecific Ligand: | 10 µM Phentolamine |
| $K_d$: | 0.58 nM* |
| $B_{max}$: | 0.17 pmole/mg protein* |
| Specific Binding: | 80%* |
| Quantitation Method: | Radioligand Binding |
| Significance Criteria: | ≧50% of max stimulation or inhibition |

203620 Adrenergic $\alpha_{2A}$

| | |
|---|---|
| Source: | Human recombinant insect Sf9 cells |
| Ligand: | 1 nM [$^3$H] MK-912 |
| Vehicle: | 1% DMSO |
| Incubation Time/Temp: | 60 minutes @ 25° C. |
| Incubation Buffer: | 75 mM Tris-HCl, pH 7.4, 12.5 mM $MgCl_2$, 2 mM EDTA |
| NonSpecific Ligand: | 10 µM WB-4101 |
| $K_d$: | 0.6 nM* |
| $B_{max}$: | 4.6 pmole/mg Protein* |
| Specific Binding: | 95%* |
| Quantitation Method: | Radioligand Binding |
| Significance Criteria: | ≧50% of max stimulation or inhibition |

203710 Adrenergic $\alpha_{2B}$

| | |
|---|---|
| Source: | Human recombinant CHO-K1 cells |
| Ligand: | 2.5 nM [$^3$H] Rauwolscine |
| Vehicle: | 1% DMSO |
| Incubation Time/Temp: | 60 minutes @ 25° C. |
| Incubation Buffer: | 50 mM Tris-HCl, 1 mM EDTA, 12.5 mM $MgCl_2$, pH 7.4, 0.2% BSA at 25° C. |
| NonSpecific Ligand: | 10 µM Prazosin |
| $K_d$: | 2.1 nM* |
| $B_{max}$: | 2.1 pmole/mg Protein* |
| Specific Binding: | 90%* |
| Quantitation Method: | Radioligand Binding |
| Significance Criteria: | ≧50% of max stimulation or inhibition |

204010 Adrenergic $\beta_1$

| | |
|---|---|
| Source: | Human recombinant Rex 16 cells |
| Ligand: | 0.03 nM [$^{125}$I] Cyanopindolol |
| Vehicle: | 1% DMSO |
| Incubation Time/Temp: | 2 hours @ 25° C. |
| Incubation Buffer: | 50 mM Tris-HCl, 5 mM EDTA, 1.5 mM $CaCl_2$, 120 mM NaCl, 1.4 mM ascorbic acid, 10 mg/L BSA, pH 7.4 |
| NonSpecific Ligand: | 100 µM S(−)-Propranolol |
| $K_d$: | 0.041 nM* |
| $B_{max}$: | 0.072 pmole/mg Protein* |
| Specific Binding: | 95%* |

204110 Adrenergic $\beta_2$

| | |
|---|---|
| Source: | Human recombinant CHO-NBR1 cells |
| Ligand: | 0.2 nM [$^3$H] CGP-12177 |
| Vehicle: | 1% DMSO |
| Incubation Time/Temp: | 60 minutes @ 25° C. |
| Incubation Buffer: | 50 mM Tris-HCl, 0.5 mM EDTA, 5.0 mM $MgCl_2$, 120 mM NaCl, pH 7.4 |
| Nonspecific Ligand: | 10 µM ICI-118551 |
| $K_d$: | 0.44 nM* |
| $B_{max}$: | 0.437 pmole/mg Protein* |
| Specific Binding: | 95%* |
| Quantitation Method: | Radioligand Binding |
| Significance Criteria: | ≧50% of max stimulation or |

| | | | |
|---|---|---|---|
| Quantitation Method: | Radioligand Binding | | inhibition |
| Significance Criteria: | ≧50% of max stimulation or inhibition | | |

212500 Bradykinin B$_1$ | 212610 Bradykinin B$_2$

| | | | |
|---|---|---|---|
| Source: | Human Hs729 cells | Source: | Human recombinant CHO-K1 cells |
| Ligand: | 2.5 nM [$^3$H] (Des-Arg$^{10}$)-Kallidin | Ligand: | 0.2 nM [$^3$H] Bradykinin |
| Vehicle: | 1% DMSO | Vehicle: | 1% DMSO |
| Incubation Time/Temp: | 60 minutes @ 25° C. | Incubation Time/Temp: | 90 minutes @ 25° C. |
| Incubation Buffer: | 20 mM HEPES, 125 mM N-methyl-D-glucamine, 5 mM KCl, 1 mM 1,10-Phenanthroline, pH 7.4 | Incubation Buffer: | 24 mM TES-NH$_4$OH, pH 6.8, 1 mM 1,10-phenanthroline, 0.3% BSA |
| NonSpecific Ligand: | 10 μM (Des-Arg, Leu)-Bradykinin | NonSpecific Ligand: | 5 μM Bradykinin |
| K$_d$: | 0.5 nM* | K$_d$: | 0.29 nM* |
| B$_{max}$: | 0.059 pmole/mg Protein* | B$_{max}$: | 2 pmole/mg Protein* |
| Specific Binding: | 70%* | Specific Binding: | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

214510 Calcium Channel L-Type, Benzothiazepine | 214600 Calcium Channel L-Type, Dihydropyridine

| | | | |
|---|---|---|---|
| Source: | Wistar Rat brain | Source: | Wistar Rat cerebral cortex |
| Ligand: | 2 nM [$^3$H] Diltiazem | Ligand: | 0.1 nM [$^3$H] Nitrendipine |
| Vehicle: | 1% DMSO | Vehicle: | 1% DMSO |
| Incubation Time/Temp: | 3 hours @ 4° C. | Incubation Time/Temp: | 90 minutes @ 25° C. |
| Incubation Buffer: | 50 mM Tris-HCl, 0.1% BSA, pH 7.4 at 25° C. | Incubation Buffer: | 50 mM Tris-HCl, pH 7.7 at 25° C. |
| NonSpecific Ligand: | 10 μM Diltiazem | NonSpecific Ligand: | 1 μM Nifedipine |
| K$_d$: | 0.016 μM* | K$_d$: | 0.18 nM* |
| B$_{max}$: | 0.21 pmole/mg Protein* | B$_{max}$: | 0.23 pmole/mg Protein* |
| Specific Binding: | 73%* | Specific Binding: | 91%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

216000 Calcium Channel N-Type | 219500 Dopamine D$_1$

| | | | |
|---|---|---|---|
| Source: | Wistar Rat brain frontal lobe | Source: | Human recombinant CHO cells |
| Ligand: | 10 pM [$^{125}$I] ω-Conotoxin GVIA | Ligand: | 1.4 nM [$^3$H] SCH-23390 |
| Vehicle: | 1% DMSO | Vehicle: | 1% DMSO |
| Incubation Time/Temp: | 30 minutes @ 4° C. | Incubation Time/Temp: | 2 hours @ 37° C. |
| Incubation Buffer: | 20 mM Tris-HCl, pH 7.4, 0.5% BSA | Incubation Buffer: | 50 mM Tris-HCl, pH 7.4, 150 mM NaCl, 1.4 mM Ascorbic Acid, 0.001% BSA |
| NonSpecific Ligand: | 0.1 μM ω-Conotoxin GVIA | | |
| K$_d$: | 0.051 nM* | NonSpecific Ligand: | 10 μM (+)-Butaclamol |
| B$_{max}$: | 0.88 pmole/mg Protein* | K$_d$: | 1.4 nM* |
| Specific Binding: | 96%* | B$_{max}$: | 0.63 pmole/mg Protein* |
| Quantitation Method: | Radioligand Binding | Specific Binding: | 90%* |
| Significance Criteria: | ≧50% of max stimulation or inhibition | Quantitation Method: | Radioligand Binding |
| | | Significance Criteria: | ≧50% of max stimulation or inhibition |

219600 Dopamine D$_{2L}$ | 219800 Dopamine D$_3$

| | | | |
|---|---|---|---|
| Source: | Human recombinant CHO cells | Source: | Human recombinant CHO cells |
| Ligand: | 0.16 nM [$^3$H] Spiperone | Ligand: | 0.7 nM [$^3$H] Spiperone |
| Vehicle: | 1% DMSO | Vehicle: | 1% DMSO |
| Incubation Time/Temp: | 2 hours @ 25° C. | Incubation Time/Temp: | 2 hours @ 37° C. |
| Incubation Buffer: | 50 mM Tris-HCl, pH 7.4, 150 mM NaCl, 1.4 mM Ascorbic Acid, 0.001% BSA | Incubation Buffer: | 50 mM Tris-HCl, pH 7.4, 150 mM NaCl, 1.4 mM Ascorbic Acid, 0.001% BSA |
| NonSpecific Ligand: | 10 μM Haloperidol | NonSpecific Ligand: | 25 μM S(−)-Sulpiride |
| K$_d$: | 0.08 nM* | K$_d$: | 0.36 nM* |
| B$_{max}$: | 0.48 pmole/mg Protein* | B$_{max}$: | 1.1 pmole/mg Protein* |
| Specific Binding: | 85%* | Specific Binding: | 85%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

219900 Dopamine D$_{4.2}$ | 224010 Endothelin ET$_A$

| | | | |
|---|---|---|---|
| Source: | Human recombinant CHO cells | Source: | Human recombinant CHO cells |
| Ligand: | 0.5 nM [$^3$H] Spiperone | Ligand: | 0.03 nM [$^{125}$I] Endothelin-1 |
| Vehicle: | 1% DMSO | Vehicle: | 1% DMSO |
| Incubation Time/Temp: | 2 hours @ 25° C. | Incubation Time/Temp: | 2 hours @ 37° C. |
| Incubation Buffer: | 50 mM Tris-HCl, pH 7.4, 150 mM NaCl, 1.4 mM Ascorbic Acid, 0.001% BSA | Incubation Buffer: | 50 mM Tris-HCl, pH 7.4, 0.5 mM CaCl$_2$, 0.05% Tween-20, 1 mg/ml BSA |
| NonSpecific Ligand: | 10 μM Haloperidol | NonSpecific Ligand: | 0.1 μM Endothelin-1 |
| K$_d$: | 0.27 nM* | K$_d$: | 0.048 nM* |
| B$_{max}$: | 1 pmole/mg Protein* | B$_{max}$: | 0.35 pmole/mg Protein* |

-continued

| | | | |
|---|---|---|---|
| Specific Binding: | 90%* | Specific Binding: | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

224110 Endothelin $ET_B$ | 225500 Epidermal Growth Factor (EGF)

| | | | |
|---|---|---|---|
| Source: | Human recombinant CHO-K1 cells | Source: | Human A431 cells |
| Ligand: | 0.1 nM [$^{125}$I] Endothelin-1 | Ligand: | 0.05 nM [$^{125}$I] Epidermal Growth Factor (EGF) (Murine) |
| Vehicle: | 1% DMSO | Vehicle: | 1% DMSO |
| Incubation Time/Temp: | 2 hours @ 25° C. | Incubation Time/Temp: | 60 minutes @ 25° C. |
| Incubation Buffer: | 50 mM HEPES, 1 mM $CaCl_2$, 5 mM $MgCl_2$, 0.5% BSA, pH 7.4 (protease free) | Incubation Buffer: | 50 mM HEPES, 138 mM NaCl, 5 mM KCl, 1.2 mM $MgSO_4$, 1.2 mM $CaCl_2$, 1 mg/ml BSA, pH 7.7 |
| NonSpecific Ligand: | 0.1 μM Endothelin-1 | NonSpecific Ligand: | 10 nM Epidermal Growth Factor (EGF) (human) |
| $K_d$: | 0.085 nM* | $K_{d1}$: | 0.032 nM* |
| $B_{max}$: | 4.3 pmole/mg Protein* | $K_{d2}$: | 0.3 nM* |
| Specific Binding: | 75%* | $B_{max1}$: | 1 pmole/mg Protein* |
| Quantitation Method: | Radioligand Binding | $B_{max2}$: | 4.1 pmole/mg Protein* |
| Significance Criteria: | ≧50% of max stimulation or inhibition | Specific Binding: | 95%* |
| | | Quantitation Method: | Radioligand Binding |
| | | Significance Criteria: | ≧50% of max stimulation or inhibition |

226010 Estrogen ERα | 226500 $GABA_A$, Agonist Site

| | | | |
|---|---|---|---|
| Source: | Human recombinant insect Sf9 cells | Source: | Wistar Rat brain (minus cerebellum) |
| Ligand: | 0.5 nM [$^3$H] Estradiol | Ligand: | 1 nM [$^3$H] Muscimol |
| Vehicle: | 1% DMSO | Vehicle: | 1% DMSO |
| Incubation Time/Temp: | 2 hours @ 25° C. | Incubation Time/Temp: | 10 minutes @ 4° C. |
| Incubation Buffer | 10 mM Tris-HCl, pH 7.5, 10% Glycerol, 1 mM DTT, 1 mg/ml BSA | Incubation Buffer: | 50 mM Tris-HCl pH 7.4 |
| NonSpecific Ligand: | 1 μM Diethylstilbestrol | NonSpecific Ligand: | 0.1 μM Muscimol |
| $K_d$: | 0.2 nM* | $K_d$: | 3.8 nM* |
| $B_{max}$: | 1400 pmole/mg Protein* | $B_{max}$: | 1.8 pmole/mg Protein* |
| Specific Binding: | 85%* | Specific Binding: | 90%* |
| Quantitation Method: | Radioligand Binding | Quantitation Method: | Radioligand Binding |
| Significance Criteria: | ≧50% of max stimulation or inhibition | Significance Criteria | ≧50% of max stimulation or inhibition |

226600 $GABA_A$, Benzodiazepine, Central | 228510 $GABA_B$, Non-Selective

| | | | |
|---|---|---|---|
| Source: | Wistar Rat brain (minus cerebellum) | Source: | Wistar Rat brain |
| Ligand: | 1 nM [$^3$H] Flunitrazepam | Ligand: | 0.6 nM [$^3$H] CGP-54626 |
| Vehicle: | 1% DMSO | Vehicle: | 1% DMSO |
| Incubation Time/Temp: | 60 minutes @ 25° C. | Incubation Time/Temp: | 20 minutes @ 25° C. |
| Incubation Buffer. | 50 mM Na-K Phosphate, pH | Incubation Buffer: | 50 mM Tris-HCl, 2.5 mM $CaCl_2$, pH 7.4 at 25° C. |
| NonSpecific Ligand: | 10 μM Diazepam | NonSpecific Ligand: | 100 μM CGP-54626 |
| $K_{d1}$: | 4.4 nM* | $K_d$: | 2.3 nM* |
| $K_{d2}$: | 0.3 nM* | $B_{max}$: | 1.1 pmole/mg Protein* |
| $B_{max1}$: | 1.2 pmole/mg Protein | Specific Binding: | 80%* |
| $B_{max2}$: | 4.1 pmole/mg | Quantitation Method: | Radioligand Binding |
| Specific Binding: | 91%* | Significance Criteria: | ≧50% of max stimulation or inhibition |
| Quantitation Method: | Radioligand Binding: | | |
| Significance Criteria: | ≧50% of max stimulation or inhibition | | |

232010 Glucocorticoid

| | |
|---|---|
| Source: | Human HeLa 53 cells |
| Ligand: | 6 nM [$^3$H] Dexamethasone |
| Vehicle | 1% DMSO |
| Incubation Time/temp: | 2 hours @ 25° C. |
| Incubation Buffer: | RPMI 1640, 10 mM HEPES, pH 7.2 |
| NonSpecific Ligand: | 20 μM Dexamethasone |
| $K_d$: | 5 nM* |
| $B_{max}$: | 61000 R/cell* |
| Specific Binding: | 75%* |
| Quantitation Method: | Radioligand Binding |
| Significance Criteria: | ≧50% of max stimulation or inhibition |

232700 Glutamate, Kainate | 232810 Glutamate, NMDA, Agonism

| | | | |
|---|---|---|---|
| Source: | Wistar Rat brain (minus cerebellum) | Source: | Wistar Rat cerebral cortex |
| Ligand: | 5 nM [$^3$H] Kainic acid | Ligand: | 2 nM [$^3$H] CGP-39653 |
| Vehicle: | 1% DMSO | Vehicle: | 1% DMSO |
| Incubation Time/Temp: | 60 minutes @ 4° C. | Incubation Time/Temp: | 20 minutes @ 4° C. |
| Incubation Buffer: | 50 mM Tris-HCl, pH 7.4 | Incubation Buffer: | 50 mM Tris-HCl, pH 7.4 |
| | | NonSpecific Ligand: | 1000 μM L-Glutamate |

*-continued*

| | | | |
|---|---|---|---|
| NonSpecific Ligand: | 1000 µM L-Glutamate | $K_d$: | 0.019 µM* |
| $K_d$: | 0.012 µM* | $B_{max}$: | 2.3 pmole/mg Protein* |
| $B_{max}$: | 0.35 pmole/mg Protein* | Specific Binding: | 70%* |
| Specific Binding: | 80%* | Quantitation Method: | Radioligand Binding |
| Quantitation Method: | Radioligand Binding | Significance Criteria: | ≥50% of max stimulation or inhibition |
| Significance Criteria: | ≥50% of max stimulation or inhibition | | |

232910 Glutamate, NMDA, Glycine | 233000 Glutamate, NMDA, Phencyclidine

| | | | |
|---|---|---|---|
| Source: | Wistar Rat cerebral cortex | Source: | Wistar Rat cerebral cortex |
| Ligand: | 0.33 nM [$^3$H] MDL-105519 | Ligand: | 4 nM [$^3$H] TCP |
| Vehicle: | 1% DMSO | Vehicle: | 1% DMSO |
| Incubation Time/Temp: | 30 minutes @ 4° C. | Incubation Time/Temp: | 45 minutes @ 25° C. |
| Incubation Buffer: | 50 mM HEPES, pH 7.7 | Incubation Buffer: | 10 mM Tris-HCl, pH 7.7 |
| NonSpecific Ligand: | 10 µM MDL-105519 | NonSpecific Ligand: | 1 µM Dizolcipine (MK-801) |
| $K_d$: | 6 nM* | $K_d$: | 8.4 nM* |
| $B_{max}$: | 3.7 pmole/mg Protein* | $B_{max}$: | 0.78 pmole/mg Protein* |
| Specific Binding: | 85%* | Specific Binding: | 94%* |
| Quantitation Method: | Radioligand Binding | Quantitation Method: | Radioligand Binding |
| Significance Criteria: | ≥50% of max stimulation or inhibition | Significance Criteria: | ≥50% of max stimulation or inhibition |

239610 Histamine $H_1$ | 239710 Histamine $H_2$

| | | | |
|---|---|---|---|
| Source: | Human recombinant CHO-K1 cells | Source: | Human recombinant CHO-K1 cells |
| Ligand: | 1.2 nM [$^3$H] Pyrilamine | Ligand: | 0.1 nM [$^{125}$I] Aminopotentidine |
| Vehicle: | 1% DMSO | Vehicle: | 1% DMSO |
| Incubation Time/Temp: | 3 hours @ 25° C. | Incubation Time/Temp: | 2 hours @ 25° C. |
| Incubation Buffer: | 50 mM Tris, pH 7.4, 2 mM Mgcl$_2$, 100 mM Nacl, 250 mM Sucrose. | Incubation Buffer: | 50 mM KH$_2$PO$_4$/Na$_2$HPO$_4$, pH 7.4 |
| NonSpecific Ligand: | 1 µM Pyrilamine | NonSpecific Ligand: | 3 µM Tiotidine |
| $K_d$: | 1.1 nM* | $K_d$: | 0.45 nM* |
| $B_{max}$: | 6.7 pmole/mg Protein* | $B_{max}$: | 6.9 pmole/mg Protein* |
| Specific Binding: | 94%* | Specific Binding: | 90%* |
| Quantitation Method: | Radioligand Binding | Quantitation Method: | Radioligand Binding |
| Significance Criteria: | ≥50% of max stimulation or inhibition | Significance Criteria: | ≥50% of max stimulation or inhibition |

239810 Histamine $H_3$ | 241000 Imidazoline $I_2$, Central

| | | | |
|---|---|---|---|
| Source: | Human recombinant CHO-K1 cel | Source: | Wistar Rat cerebral cortex |
| Ligand: | 3 nM [$^3$H] R(−)-α-Methylhistamine (RAMH) | Ligand: | 2 nM [$^3$H] Idazoxan |
| Vehicle: | 1% DMSO | Vehicle: | 1% DMSO |
| Incubation Time/Temp: | 90 minutes @ 25° C. | Incubation Time/Temp: | 30 minutes @ 25° C. |
| Incubation Buffer: | 50 mM Tris-HCl, pH 7.4 10 mM MgCl$_2$, 0.04% BSA | Incubation Buffer: | 50 mM Tris-HCl, 0.5 mM EDTA, pH 7.4 at 25° C. |
| NonSpecific Ligand: | 1 µM R(−)-α-Methylhistamine (RAMH) | NonSpecific Ligand: | 1 µM Idazoxan |
| $K_d$: | 2.4 nM* | $K_d$: | 4 nM* |
| $B_{max}$: | 4.2 pmole/mg Protein* | $B_{max}$: | 0.14 pmole/mg Protein* |
| Specific Binding: | 95%* | Specific Binding: | 85%* |
| Quantitation Method: | Radioligand Binding | Quantitation Method: | Radioligand Binding |
| Significance Criteria: | ≥50% of max stimulation or inhibition | Significance Criteria: | ≥50% of max stimulation or inhibition |

243510 Interleukin IL-1, Non-Selective | 250600 Leukotriene LTD$_4$

| | | | |
|---|---|---|---|
| Source: | Mouse 3T3 cells | Source: | Duncan Hartley derived Guinea pig lung |
| Ligand: | 10 pM [$^{125}$I] Interleukin-1α (IL-1α) | Ligand: | 0.2 nM [$^3$H] Leukotriene D$_4$ (LTD$_4$) |
| Vehicle: | 1% DMSO | Vehicle: | 1% DMSO |
| Incubation Time/Temp: | 2 hours @ 37° C. | Incubation Time/Temp: | 60 minutes @ 25° C. |
| Incubation Buffer: | RPMI 1640, 20 mM HEPES, 0.1% Sodium Azide. 1% BSA, pH 7.2. | Incubation Buffer: | 50 mM Tris-HCl, 0.01% BSA, 5 mM CaCl$_2$, 5 mM MgCl$_2$, 100 µg/mL Bacitracin, 1 mM Benzamidine, 0.1 mM Phenylmethylsulfonyl Fluoride |
| NonSpecific Ligand: | 0.03 µM Interleukin-1α (IL-1α) | | |
| $K_d$: | 6 pM* | | |
| $B_{max}$: | 8.2 fmole/mg Protein* | | |
| Specific Binding: | 70%* | NonSpecific Ligand: | 0.1 µM Leukotriene D$_4$ (LTD$_4$) |
| Quantitation Method: | Radioligand Binding | $K_d$: | 0.2 nM* |
| Significance Criteria: | ≥50% of max stimulation or inhibition | $B_{max}$: | 0.24 pmole/mg Protein* |
| | | Specific Binding: | 85%* |
| | | Quantitation Method: | Radioligand Binding |
| | | Significance Criteria: | ≥50% of max stimulation or inhibition |

252600 Muscarinic $M_1$ | 252700 Muscarinic $M_2$

| | | | |
|---|---|---|---|
| Source: | Human recombinant insect Sf9 cells | Source: | Human recombinant insect Sf9 cells |
| Ligand: | 0.29 nM [$^3$H] Methscopolamine | Ligand: | 0.29 nM [$^3$H] Methscopolamine |
| Vehicle: | 1% DMSO | Vehicle: | 1% DMSO |
| Incubation Time/Temp: | 60 minutes @ 25° C. | Incubation Time/Temp: | 60 minutes @ 25° C. |

-continued

| | | | |
|---|---|---|---|
| Incubation Buffer: | 50 mM Tris-HCl, pH 7.4 10 mM MgCl$_2$, 1 mM EDTA | Incubation Buffer: | 50 mM Tris-HCl, pH 7.4, 10 mM MgCl$_2$, 1 mM EDTA |
| NonSpecific Ligand | 1 μM Atropine | NonSpecific Ligand: | 1 μM Atropine |
| K$_d$: | 0.092 nM* | K$_d$: | 0.16 nM* |
| B$_{max}$: | 2.1 pmole/mg Protein* | B$_{max}$: | 4.9 pmole/mg Protein* |
| Specific Binding: | 95%* | Specific Binding: | 96%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

252800 Muscarinic M$_3$     257000 Neuropeptide Y$_1$

| | | | |
|---|---|---|---|
| Source: | Human recombinant insect Sf9 cells | Source: | Human SK-N-MC cells |
| Ligand: | 0.29 nM [$^3$H] Methscopolamine | Ligand: | 0.013 nM [$^{125}$I] Peptide YY |
| Vehicle: | 1% DMSO | Vehicle: | 1% DMSO |
| Incubation Time/Temp: | 60 minutes @ 25° C. | Incubation Time/Temp: | 45 minutes @ 25° C. |
| | | Incubation Buffer: | HBSS, 2 mg/mL BSA, 1 mM MgCl$_2$, 1 mM CaCl$_2$ |
| Incubation Buffer: | 50 mM Tris-HCl, pH 7.4, 10 mM MgCl$_2$, 1 mM EDTA | | |
| NonSpecific Ligand: | 1 μM Atropine | NonSpecific Ligand: | 0.1 μm Neuropeptide Y (human, rat) |
| K$_d$: | 0.078 nM* | K$_d$: | 0.62 nM* |
| B$_{max}$: | 3.2 pmole/mg Protein* | B$_{max}$: | 5800 R/cell Receptors/cell* |
| Specific Binding: | 96%* | Specific Binding: | 85%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

257110 Neuropeptide Y$_2$     258590 Nicotinic Acetylcholine

| | | | |
|---|---|---|---|
| Source: | Human KAN-TS neuroblastoma cell | Source: | Human IMR-32 cells |
| Ligand: | 10 pM [$^{125}$I] Peptide YY | Ligand: | 0.1 nM [$^{125}$I] Epibatidine |
| Vehicle: | 1% DMSO | Vehicle: | 1% DMSO |
| Incubation Time/Temp: | 2 hours @ 37° C. | Incubation Time/Temp: | 60 minutes @ 25° C. |
| Incubation Buffer: | 25 mM HEPES, 2.5 mM CaCl$_2$, 1 mM MgCl$_2$, 0.1% Bacitracin, pH 7.4 | Incubation Buffer: | 50 mM Tris-HCl, pH 7.4 |
| | | NonSpecific Ligand: | 300 μM (−)-Nicotine |
| NonSpecific Ligand: | 1 μM Neuropeptide Y (13–36) (porcine) | K$_d$: | 0.22 nM* |
| | | B$_{max}$: | 0.46 pmole/mg Protein* |
| K$_d$: | 0.012 nM* | Specific Binding: | 97%* |
| B$_{max}$: | 0.5 pmole/mg Protein* | Quantitation Method: | Radioligand Binding |
| Specific Binding: | 90%* | Significance Criteria: | ≧50% of max stimulation or inhibition |
| Quantitation Method: | Radioligand Binding | | |
| Significance Criteria: | ≧50% of max stimulation or inhibition | | |

260110 Opiate δ (OP1, DOP)

| | |
|---|---|
| Source: | Human recombinant CHO cells |
| Ligand: | 0.9 nM [$^3$H] Naltrindole |
| Vehicle: | 1% DMSO |
| Incubation Time/Temp: | 2 hours @ 25° C. |
| Incubation Buffer: | 50 mM Tris-HCl, 5 mM MgCl$_2$, pH 7.4 |
| NonSpecific Ligand: | 10 μM Naloxone |
| K$_d$: | 0.49 nM* |
| B$_{max}$: | 8.6 pmole/mg Protein* |
| Specific Binding: | 80%* |
| Quantitation Method: | Radioligand Binding |
| Significance Criteria: | ≧50% of max stimulation or inhibition |

260210 Opiate κ (OP2, KOP)     260410 Opiate μ (OP3, MOP)

| | | | |
|---|---|---|---|
| Source: | Human recombinant HEK-293 cells | Source: | Human recombinant CHO cells |
| Ligand: | 0.6 nM [$^3$H] Diprenorphine | Ligand: | 0.6 nM [$^3$H] Diprenorphine |
| Vehicle: | 1% DMSO | Vehicle: | 1% DMSO |
| Incubation Time/Temp: | 60 minutes @ 25° C. | Incubation Time/Temp: | 60 minutes @ 25° C. |
| Incubation Buffer: | 50 mM Tris-HCl, pH 7.4 | Incubation Buffer: | 50 mM Tris-HCl, pH 7.4 |
| NonSpecific Ligand: | 10 μM Naloxone | NonSpecific Ligand: | 10 μM Naloxone |
| K$_d$: | 0.4 nM* | K$_d$: | 0.41 nM* |
| B$_{max}$: | 1.1 pmole/mg Protein* | B$_{max}$: | 3.8 pmole/mg Protein* |
| Specific Binding: | 90%* | Specific Binding: | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

264500 Phorbol Ester     265010 Platelet Activating Factor (PAF)

| | | | |
|---|---|---|---|
| Source: | ICR Mouse brain | Source: | Human platelets |
| Ligand: | 3 nM [$^1$H] PDBu | Ligand: | 0.12 nM [$^1$H] PAF |
| Vehicle: | 1% DMSO | Vehicle: | 1% DMSO |
| Incubation Time/Temp: | 60 minutes @ 25° C. | Incubation Time/Temp: | 3 hours @ 25° C. |

-continued

| | | | |
|---|---|---|---|
| Incubation Buffer: | 20 mM Tris-HCl containing 5 mM CaCl$_2$, pH 7.5 at 25° C. | Incubation Buffer: | 50 mM Tris-HCl, pH 7.4 100 mM KCl, 5 mM EDTA, 5 mM MgCl$_2$, 0.25% BSA (w/v). |
| NonSpecific Ligand: | 1 µM PDBu | NonSpecific Ligand: | 1 µM PAF |
| K$_d$: | 8.7 nM* | K$_d$: | 0.13 nM* |
| B$_{max}$: | 26 pmole/mg Protein* | B$_{max}$: | 120 R/cell* |
| Specific Binding: | 80%* | Specific Binding: | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

265600 Potassium Channel [K$_{ATP}$]

| | |
|---|---|
| Source: | Syrian hamster pancreatic beta cells HIT-T15 |
| Ligand: | 5 nM [$^3$H] Glibenclamide |
| Vehicle: | 1% DMSO |
| Incubation Time/Temp: | 2 hours @ 25° C. |
| Incubation Buffer: | 50 mM MOPS, 0.1 mM CaCl$_2$, pH 7.4 |
| NonSpecific Ligand: | 1 µM Glyburide |
| K$_d$: | 0.64 nM* |
| B$_{max}$: | 1 pmole/mg Protein* |
| Specific Binding: | 90%* |
| Quantitation Method: | Radioligand Binding |
| Significance Criteria: | ≧50% of max stimulation or inhibition |

268700 Purinergic P$_{2X}$

| | |
|---|---|
| Source: | New Zealand Derived Albino Rabbit urinary bladder |
| Ligand: | 8 nM [$^3$H] α,β-Methylene-ATP |
| Vehicle: | 1% DMSO |
| Incubation Time/Temp: | 30 minutes @ 25° C. |
| Incubation Buffer: | 50 mM Tris-HCl, pH 7.4 |
| NonSpecific Ligand: | 100 µM β, γ-Methylene ATP |
| K$_{d1}$: | 2.2 nM* |
| K$_{d2}$: | 2.2 µM* |
| B$_{max1}$: | 2 pmole/mg Protein* |
| B$_{max2}$: | 790 pmole/mg Protein* |
| Specific Binding: | 80%* |
| Quantitation Method: | Radioligand Binding |
| Significance Criteria: | ≧50% of max stimulation or inhibition |

268810 Purinergic P$_{2Y}$

| | |
|---|---|
| Source: | Wistar Rat brain |
| Ligand: | 0.1 nM [$^{35}$S] ATP-αS |
| Vehicle: | 1% DMSO |
| Incubation Time/Temp: | 60 minutes @ 25° C. |
| Incubation Buffer: | 50 mM Tris-HCl, pH 7.4 |
| NonSpecific Ligand: | 10 µM ADP-βS |
| K$_d$: | 0.015 µM* |
| B$_{max}$: | 16 pmole/mg Protein* |
| Specific Binding: | 87%* |
| Quantitation Method: | Radioligand Binding |
| Significance Criteria: | ≧50% of max stimulation or inhibition |

271110 Serotonin (5-Hydroxytryptamine) 5-HT$_{1A}$

| | |
|---|---|
| Source: | Human recombinant CHO cells |
| Ligand: | 1.5 nM [$^3$H] 8-OH-DPAT |
| Vehicle: | 1% DMSO |
| Incubation Time/Temp: | 60 minutes @ 25° C. |
| Incubation Buffer: | 50 mM Tris-HCl, 10 mM MgSO$_4$, 0.5 mM EDTA, 0.1% Ascorbic Acid, pH 7.4 |
| NonSpecific Ligand: | 10 µM Metergoline |
| K$_d$: | 2 nM* |
| B$_{max}$: | 1.3 pmole/mg Protein* |
| Specific Binding: | 75%* |
| Quantitation Method: | Radioligand Binding |
| Significance Criteria: | ≧50% of max stimulation or inhibition |

271910 Serotonin (5-Hydroxytryptamine) 5-HT$_3$

| | |
|---|---|
| Source: | Human recombinant HEK-293 cells |
| Ligand: | 0.69 nM [$^3$H] GR-65630 |
| Vehicle: | 1% DMSO |
| Incubation Time/Temp: | 60 minutes @ 25° C. |
| Incubation Buffer: | 50 mM Tris-HCl, pH 7.5, 1 mM EDTA, 5 mM MgCl$_2$ |
| NonSpecific Ligand: | 10 µM MDL-72222 |
| K$_d$: | 0.2 nM* |
| B$_{max}$: | 11 pmole/mg Protein* |
| Specific Binding: | 90%* |
| Quantitation Method: | Radioligand Binding |
| Significance Criteria: | ≧50% of max stimulation or inhibition |

278110 Sigma σ$_1$

| | |
|---|---|
| Source: | Human Jurkat cells |
| Ligand: | 8 nM [$^3$H] Haloperidol |
| Vehicle: | 1% DMSO |
| Incubation Time/Temp: | 4 hours @ 25° C. |
| Incubation Buffer: | 5 mM K$_2$HPO$_4$/KH$_2$PO$_4$ buffer pH 7.5 |
| NonSpecific Ligand: | 10 µM Haloperidol |
| K$_d$: | 5.8 nM* |
| B$_{max}$: | 0.71 pmole/mg Protein* |
| Specific Binding: | 80%* |
| Quantitation Method: | Radioligand Binding |
| Significance Criteria: | ≧50% of max stimulation or inhibition |

278200 Sigma σ$_2$

| | |
|---|---|
| Source: | Wistar Rat brain |
| Ligand: | 3 nM [$^3$H] Ifenprodil |
| Vehicle: | 1% DMSO |
| Incubation Time/Temp: | 60 minutes @ 37° C. |
| Incubation Buffer: | 50 mM Tris-HCl, pH 7.4 |
| NonSpecific Ligand: | 10 µM Ifenprodil |
| K$_d$: | 4.8 nM* |
| B$_{max}$: | 1.3 pmole/mg Protein* |
| Specific Binding: | 85%* |
| Quantitation Method: | Radioligand Binding |
| Significance Criteria: | ≧50% of max stimulation or inhibition |

279450 Sodium Channel, Site 1

| | |
|---|---|
| Source: | Wistar Rat brain |
| Ligand: | 2 nM [$^3$H] Saxitoxin |
| Vehicle: | 1% DMSO |
| Incubation Time/Temp: | 30 minutes @ 4° C. |
| Incubation Buffer: | (1) Homogenization buffer: 140 mM NaCl, 20 mM Tris-HCl, pH 7.1, 1 mM PMSF (2) 75 mM Hepes/140 mM NaCl, pH 7.5 (3) Assay buffer: homogenization buffer to buffer (2) is 1:4 |
| NonSpecific Ligand: | 10 µM Tetrodotoxin |
| K$_d$: | 1.4 nM* |
| B$_{max}$: | 3.7 pmole/mg Protein* |
| Specific Binding: | 90% |
| Quantitation Method: | Radioligand Binding |
| Significance Criteria: | ≧50% of max stimulation or inhibition |

-continued

| 279510 Sodium Channel, Site 2 | | 255510 Tachykinin NK$_t$ | |
|---|---|---|---|
| Source: | Wistar Rat brain | Source: | Human recombinant CHO cells |
| Ligand: | 5 nM [$^3$H] Batrachotoxinin A 20-α-Benzoate | Ligand: | 0.25 nM [$^3$H] SR-140333 |
| Vehicle: | 1% DMSO | Vehicle: | 1% DMSO |
| Incubation Time/Temp: | 60 minutes @ 37° C. | Incubation Time/Temp: | 90 minutes @ 25° C. |
| Incubation Buffer: | 50 mM Tris-HCl, pH 7.4 at 25° C., 50 mM HEPES, 130 mM choline-Cl, 5.4 mM KCl, 0.8 mM MgSO$_4$,7H$_2$O (or MgCl$_2$), 5.5 mM Glucose, 40 µg/ml LqTx | Incubation Buffer: | 20 mM HEPES, pH 7.4, 1 mM MnCl$_2$, 0.01% BSA |
| | | NonSpecific Ligand: | 2 µM L-703,606 |
| | | K$_d$: | 0.3 nM* |
| | | B$_{max}$: | 10 pmole/mg Protein* |
| | | Specific Binding: | 85%* |
| NonSpecific Ligand: | 100 µM Veratridine | Quantitation Method: | Radioligand Binding |
| K$_d$: | 0.052 µM* | Significance Criteria: | ≧50% of max stimulation or inhibition |
| B$_{max}$: | 0.7 pmole/mg Protein* | | |
| Specific Binding: | 77%* | | |
| Quantitation Method: | Radioligand Binding | | |
| Significance Criteria: | ≧50% of max stimulation or inhibition | | |
| 285010 Testosterone | | 220320 Transporter, Dopamine (DAT) | |
| Source: | Rat recombinant E. coli | Source: | Human recombinant CHO cells |
| Ligand: | 1.5 nM [$^3$H] Mibolerone | Ligand: | 0.15 nM [I] RTI-55 |
| Vehicle: | 1% DMSO | Vehicle: | 1% DMSO |
| Incubation Time/Temp: | 4 hours @ 4° C. | Incubation Time/Temp: | 3 hours @ 4° C. |
| Incubation Buffer: | 50 mM Tris-HCl (pH 7.5), 0.8 M NaCl, 10% Glycerol, 2 mM Dithiothreitol, 1 mg/ml BSA and 2% Ethanol | Incubation Buffer: | 100 mM NaCl, 50 mM Tris-HCl, 1 µM Leupeptin, 10 µM PMSF, pH 7.4 |
| | | NonSpecific Ligand: | 10 µM Nomifensine |
| | | K$_d$: | 0.58 nM* |
| NonSpecific Ligand: | 10 µM Mibolerone | B$_{max}$: | 0.047 pmole/mg Protein* |
| K$_d$: | 3 nM* | Specific Binding: | 90%* |
| B$_{max}$: | 930 pmole/mg Protein* | Quantitation Method: | Radioligand Binding |
| Specific Binding: | 90%* | Significance Criteria: | ≧50% of max stimulation or inhibition |
| Quantitation Method: | Radioligand Binding | | |
| Significance Criteria: | ≧50% of max stimulation or inhibition | | |
| | | 274020 Transporter, Serotonin (5-Hydroxytryptamine) (SERT) | |
| 204410 Transporter, Norepinephrine (NET) | | | |
| Source: | Human recombinant MDCK cells | Source: | Human recombinant HEK-293 cells |
| Ligand: | 0.2 nM [$^{125}$I] RTI-55 | Ligand: | 0.15 nM [$^{125}$I] RTI-55 |
| Vehicle: | 1% DMSO | Vehicle: | 1% DMSO |
| Incubation Time/Temp: | 3 hours @ 4° C. | Incubation Time/Temp: | 3 hours @ 4° C. |
| Incubation Buffer: | 50 mM Tris-HCL 100 mM NaCl, 1 µM leupeptin, 10 µM PMSF, pH 7.4 | Incubation Buffer: | 100 mM NaCl, 50 mM Tris HCl, 1 µM Leupeptin, 10 µM PMSF, pH 7.4 |
| NonSpecific Ligand: | 10 µM Desipramine | NonSpecific Ligand: | 10 µM Imipramine |
| K$_d$: | 0.024 µM* | K$_d$: | 0.17 nM* |
| B$_{max}$: | 2.5 pmole/mg Protein* | B$_{max}$: | 0.41 pmole/mg Protein* |
| Specific Binding: | 75%* | Specific Binding: | 95%* |
| Quantitation Method: | Radioligand Binding | Quantitation Method: | Radioligand Binding |
| Significance Criteria: | ≧50% of max stimulation or inhibition | Significance Criteria: | f 50% of max stimulation or inhibition |
| 226400 Transporter, GABA | | | |
| Source: | Wistar Rat cerebral cortex | | |
| Ligand: | 6 nM [$^3$H] GABA | | |
| Vehicle: | 1% DMSO | | |
| Incubation Time/Temp: | 20 minutes @ 25° C. | | |
| Incubation Buffer: | 10 mM Na-HEPES, 120 mM NaCl, 4 mM Ca Acetate, 10 µM Isoguvacine, 10 µM (−)Baclofen, pH 7.5 | | |
| NonSpecific Ligand: | 10 µM NO-711 | | |
| K$_d$: | 0.3 µM* | | |
| B$_{max}$: | 60 pmole/mg Protein* | | |
| Specific Binding: | 80%* | | |
| Quantitation Method: | Radioligand Binding | | |
| Significance Criteria: | ≧50% of max stimulation or inhibition | | |

*Historical Values

LITERATURE REFERENCES

CAT. #. Reference

118050. Crespi, C. L., Miller, V. P. and Penman, B. W. (1997) Microtiter plate assays for inhibition of human, drug-metabolizing cytochromes P450. *Anal Biochem* 248 (1): 188–190.

Gentest Technical Bulletin (Version 4.2: Revised 27 Sep. 2000) A high throughput method for measuring cytochrome P450 inhibition. *Gentest Technical Bulletin* (Version 4-2. Revised 27 Sep. 2000).

118060. Crespi, C. L., Miller, V. P. and Penman, B. W. (1997) Microtiter plate assays for inhibition of human, drug-metabolizing cytochromes P450. *Anal Biochem* 248 (1): 188–190.

Gentest Technical Bulletin (Version 4.2: Revised 27 Sep. 2000) A high throughput method for measuring cytochrome P450 inhibition. *Gentest Technical Bulletin* (Version 4-2: Revised 27 Sep. 2000).

118070. Crespi, C. L., Miller, V. P. and Penman, B. W. (1997) Microtiter plate assays for inhibition of human, drug-metabolizing cytochromes P450. *Anal Biochem* 248 (1):188–190.

Gentest Technical Bulletin (Version 4.2: Revised 27 Sep. 2000) A high throughput method for measuring cytochrome P450 inhibition. *Gentest Technical Bulletin* (Version 4-2: Revised 27 Sep. 2000).

118080. Crespi, C. L., Miller, V. P. and Penman, B. W. (1997) Microtiter plate assays for inhibition of human, drug-metabolizing cytochromes P450. *Anal Biochem* 248 (1): 188–190.

Gentest Technical Bulletin (Version 4.2: Revised 27 Sep. 2000) A high throughput method for measuring cytochrome P450 inhibition. *Gentest Technical Bulletin* (Version 4-2: Revised 27 Sep. 2000).

118090. Crespi, C. L., Miller, V. P. and Penman, B. W. (1997) Microtiter plate assays for inhibition of human, drug-metabolizing cytochromes P450. *Anal Biochem* 248M: 188–190.

Gentest Technical Bulletin (Version 4.2: Revised 27 Sep. 2000) A high throughput method for measuring cytochrome P450 inhibition. *Gentest Technical Bulletin* (Version 4.2: Revised 27 Sep. 2000).

200510. Libert, F., Sande, J. V., Lefort, A., Czernilofsky, A., Dumont, J. E., Vassart, G., Ensinger, H. A. and Mendla, K. D. (1992). Cloning and functional characterization of a human A1 adenosine receptor. *Biochem. Biophys. Res. Commun.* 187:919–926.

200610. Varani, K., Gessi, S., Dalpiaz, A. and Borea, P. A. (1996) Pharmacological and biochemical characterization of purified A2A adenosine receptors in human platelet membranes by [3H]CG521680 binding. Br. *J Pharmacol.* 117:1693–1701

203100. Michel, A. D., Loury, D. N., Whiting, R. L. (1989) Identification of a single a1 A-adrenoceptor corresponding to the a1 A-subtype in rat submaxillary gland. Br. *J. Pharmacol.* 98:883–889.

203200. Garcia-Sainz, J. A., Romero-Avila, M. T., Hernandez, R. A., Macias-Silva, M., Olivares-Reyes, A., Gonzalez-Espinosa, C. (1992) Species heterogeneity of hepatic a1-adrenoceptors: at A-, a1 B-, and at C-subtypes. *Biochem. Biophys. Res. Comm.* 186:760–767.

Michel, A. D., Loury, D. N., and Whiting, R. L. (1989) Identification of a single a1 A-adrenoceptor corresponding to the a1 A subtype in the rat submaxillary gland. Br. *J. Pharmacol.* 98:833–889.

203400. Kenny, B. A., Chalmers, D. H., Philpott, P. C. and Naylor A. M. (1995) Characterization of an a1 D-adrenoceptor mediating the contractile response of rat aorta to noradrenaline. *British Journal of Pharmacology.* 115: 981–986

203620. UhlSn, S., Porter, A. C., Neubig, R. R. (1994) The novel alpha-2 adrenergic radioligand [3H]MK912 is alpha-2C selective among human alpha-2A, alpha-2B and alpha-2C adrenoceptors. *J. Pharmacol. Exp. Ther.* 271: 1558–1565.

203710. Uhlen S., Dambrova, M., Nasman, J., Schioth, H. B., Gu, Y., Wikberg-Matsson, A., Wikberg, J. E., (1998) Alpha 213- and alpha 2C- adrenoceptors. comparison with MK912, RX821002, rauwolscine and yohimbine. *Eur. J. Pharmacol.* 343 (1): 93–101.

204010. Feve, B., Elhadri, K., Quignard-Boulange, A., Pairault, J. (1994) Transcriptional down-regulation by insulin of the b3-adrenergic receptor expression in 3T3-F442A adipocytes: a mechanism for repressing the CAMP signalling pathway. *Proc. NatL Acad. Sci. USA* 91:5677–5681.

204110. McCrea, K. E. and Hill S. J. (1993) Salmeterol, a long-acting b2-adrenoceptor agonist mediating cyclic AMP accumulation in a neuronal cell line. *Brit. J Pharmacol.* 110:619–626.

204410. Galli, A., De Felice, L., Duke, B.-J., Moore, K., Blakely, R. (1995) Sodium dependent norepinephrine induced currents in norepinephrine transporter transfected HEK293 cells blocked by cocaine and antidepressants. *J. Exp. Biol.* 198:2197–2212.

212500. Menke, J., Borkowski, J. A., Bierilo, K. K., MacNeil, T., Derrick, A. W., Schneck, K. A., Ransom, R. W. Strader, C. D., Linemeyer, D. L., Hess, J. F. (1994) Expression cloning of a human B1 bradykinin receptor. *J. Biol. Chem.* 269:21583–21586.

212610. Eggerickx, D., Raspe, E., Bertrand, D., Vassart, G., Parmentier, M. (1992) Molecular cloning, functional expression and pharmacological characterization of a human bradykinin B2 receptor gene. *Biochem Biophys Res Commun* 187 (3): 1306–1313.

214510. Schoemaker, H. and Langer S. Z. (1985) [3H] Diltiazem binding to calcium channel antagonist recognition sites in rat cerebral cortex. *Eur. J. Pharmacol.* 111:273–277.

214600. Ehlert, F. J., Roeske, W. R., Itoga, E., and Yamamura, H. I. (1982) The binding of [3H]nitrendipine to receptors for calcium channel antagonists in the heart, cerebral cortex and ileum of rats. *Life Sci.* 30:2191–2202.

Gould R. J., Murphy, K. M. M., Snyder, S. H. (1982) [3H]nitrendipine-labeled calcium channels discriminate inorganic calcium agonists and antaggonists. *Proc Natl. Acad. Sci. USA* 79:3656–3650.

216000. Moresco, R. M., Govoni, S., Battaini, F., Trivulzio, S., Trabucchi, M. (1990) Omegaconotoxin binding decreases in aged rat brain. *Neurobiol. of Aging* 11:433–436.

219500. Dearry, A., Gingrich, J. A., Falardeau, P., Fremeau, R. T jr., Bates, M. D., Caron, M. G. (1990) Molecular cloning and expression of the gene for a human D1 dopamine receptor. *Nature* 347:72–76.

Sunahara, R. K., Niznik, H. B., Weiner, D. M., Stormann, T. M., Brann, M. R., Kennedy, J. L., Gelernter, J. E., Rozmahel, R., Yang, Y., Israel, Y., Seeman, P., and O'Dowd, B. F. (1990) Human Dopamine D1 receptor encoded by an intronless gene on chromosome 5. *Nature* 347:80–83.

Zhou, Q.-Y., Grandy, D. K., Thambi, L., Kushner, J. A., Van To[, H. H. M., Cone, R., Pribnow, D., Salon, J. Bunzow, J. R., and Civelli, O. (1990) Cloning and expression of human and rat D1 dopamine receptors. *Nature* 347:76–80.

219600. Bunzo, J. R., Van To[, H. H. M., Grandy, D. K., Albert, P., Salon, J., Christie, M., Machida, C. A., Neve, K. A., and Civelli, O. (1988) Cloning and expression of rat D2 dopamine receptor cDNA *Nature* 336:783–787.

Grandy, D. K., Marchionni, M. A., Makam, H., Stofko, R. E., Alfano, M., Frothingham, L, Fischer, J. B. Burke-Howie, K. J., Bunzow, J. R., Seiver, A. C., Civelli, O. (1989) Cloning of the cDNA and gene for a human D2 dopamine receptor. *Proc. NatL Acad. Sci. USA* 86:9762–9766.

Hayes, G., Biden, T. J., Selbie, L. A., and Shine, J. (1992) Structural subtypes of the dopamine D2 receptor are functionally distinct: Expression of the clone D2A and D2B subtypes in a heterologous cell line. *Molec. Endocrin.* 6:920–926.

219800. Sokoloff, P., Giros, B., Martres, M. P., Bouthenet, M. L., Schwartz, J. C. (1990) Molecular cloning and characterization of a novel dopamine receptor (D3) as a target for neuroleptics. *Nature* 347:146–151.

219900. Van Tot, H. H. M., Bunzow, J. R., Guan, H. C., Sunahara, R. K., Seeman, P., Niznik, H. B., Civelli, O. (1991) Cloning of the gene for a human dopamine D4 receptor with high affinity for the antipsychotic clozapine. *Nature* 350:610–614.

Van To[, H. H. M., Wu, C. M., Guan, H.-C., Ohara, K., Bunzow, J. R., Civelli, 0., Kennedy, J., Seeman, P. Niznik, H. B., and Jovanovic, V. (1992) Multiple dopamine D4 receptor variants in the human population. *Nature* 358: 149–152.

220320. Giros, B. and Caron., M. G. (1993). Molecular characterization of the dopamine transporter. *Trends. Pharmacol. Sci.* 14: 43–49.

220320. Gu, H., Wall, S., Rudnick, G. (1994) Stable expression of biogenic akin transporters reveals differences in inhibitor sensitivity, kinetics, and ion dependence. *J. Biol. Chem.* 269(10):7124–7130.

224010. Pharmacological characterization of a potent nonpeptide endothelia receptor antagonist, 97–139. *The Journal of Pharmacology and Experimental Therapeutics.* 268: 1122–1127.

224110. Cain, M. J., Garlick, R. K. and Sweetman, P. M. (1991) Endothelia-1 receptor binding assay for high throughput chemical screening. *J Cardiovasc Pharmacol* 17 Suppl 7: 5150-i51

Chiou, W. J., Magnuson, S. R., Dixon, D., Sundy, S., Opgenorth, T. J. and Wu-Wong, J. R. (1997) Dissociation characteristics of endothelia receptor agonists and antagonists in cloned human type-B endothelia 225500. Dittadi, R., Gion, M., Brazzale, A., Bruscagnin, G. (1990) Radioligand binding assay of epidermal growth factor receptor: Causes of variability and standardization of the assay. *Clin. Chem.* 36:849–854.

Massague, J. (1983) Epidermal growth factor-like transforming growth factodr: II. Interaction with epidermal growth factor receptors in human placenta membranes and A431 cells. *J. Biol. Chem.* 258:13614–13620.

226010. Oboum, J. D., Koszewski, N. J. and Notides, A. C. (1993) Hormone-and DNA-binding mechanism of the recombinant human estrogen receptor. *Biochemistry.* 32: 6229–6236.

226400. Shank, R. P., Baldy, W. J., Matucci, L. C., Villani, F. J. Jr. (1990) Ion and temperature effects on the binding of gamma-aminobutyrate to its receptors and the high-affinity transport system. *J. Neurochem.* 54:2007–2015.

226500. Enna, S. J., and Snyder, S. H. (1976) Influences of ions, enzymes and detergents on gamma-aminobutyric acid-receptor binding in synaptic membranes of rat brain. *Mol. Pharmacol.* 13:442–453.

Martinin, C., Rigacci, T., Lucacchini, A. (1983) [3H]muscimol binding site on purified benzodiazepine receptor. *J. Neurochem.* 41:1183–1185.

Snodgrass, S. R. (1978) Use of [3H]muscimol for GABA receptor studies. *Nature* 273:392–394.

226600. Damm, H. W., Mueller, W. E., Schlaefer, U., Wollert, U. (1978) [3H]flunitrazepam: Its advantages as a ligand, for the identification of benzodiazepine receptors in rat brain membranes. *Res. Comm. Chem. Pathol. Pharmacol.* 22:597–600.

Speth, R. C., Wastek, G. J., and Yamamura, H. I. (1979) Benzodiacepam receptors: temperature dependence of [3H]flunitrazepam binding. *Life Sci.* 24:351–357.

228510. Facklam, M. and Bowery, N., G. (1993) Solubiliaztion and characterization of GABAB receptor binding sites from porcine brain synaptic membranes. *Br. J. Pharmacol.* 110: 1291–1296

228510. Mathivet P., Bemasconi, R., Barry, J. D., Marescaux, C., Bittiger, H. (1992) Binding characteristics of y-hydroxybutyric acid as a weak but selective GABAB receptor agonist. *Eur. J Pharmacol.* 321: 67–75

232010. Cidlowski, J. A. and Cidlowski, N. B. (1981) Regulation of glucocorticoid receptors by glucocorticoids in Cultured HeLa S3 Cells. *Endocrinology* 109: 1975–1982.

232700. London, E. D. and Coyle J. T. (1979) Specific binding of [3H]kainic acid to receptor sites in rat brain. *Mol. Pharmacol.* 15:492–505.

232810. Sills, M. A. Fagg, G. Pozza, M. Angst, C. Brundish, D. E. Hurt, S. D. Wilusz, E. J. and Williams, M. (1991). [$^3$H]CGP 39653: a new N-methyl-D-aspartate antagonist radioligand with low nanomolar affinity in rat brain. *European Journal of Pharmacology* 192: 19–24.

232910. Seifel, B. W., Sreekrishna, K., Baron, B. M. (1996) Binding of the radiolabeled glycine antagonist [3H] MDS105,519 to homomeric NMDA-NR$_1$a receptors. *Eur. J Pharmacol.* 312:357–365.

233000. Goldman, M. E., Jacobson, A. E., Rice, K. C., Paul, S. M. (1985) Differentiation of [3H] phencyclidine and (+)-[3H]SKF-10047 binding sites in rat cerebral cortex. *FEBS Lett.* 190:333–336.

239610. De Backer, M. D., Gommeren, W., Moereels, H., Nobels, G., Van Gompel, P., Leysen, J. E. and Luyten, W. H. (1993) Genomic cloning, heterologous expression and pharmacological characterization of a human histamine H1 receptor. *Biochemical and Biophysical Research Communications.* 1601–1608

239710. Ruat, M., Traiffort, E., Bouthenet, M. L., Schwartz, J. C., Hirschfeld, J., Buschauer, A. anad Schunack, W. (1990) Reversible and irreversible labeling and autoradiographic localization of the cerebral histamine H2 receptor using [$^{125}$I]iodinated probes. *Proceedings of the National Academy of Sciences of the United States of America.* 87(5): 1658–1662.

239810. Yanai, K., Ryu, J. H., Sakai, N., Takahashi, T., Iwata, R., Ido, T., Murakami, K. and Watanabe, T.(1994) Binding characteristics of a histamine H3-receptor antagonist, [3H]S-methylthioperamide: comparison with [3H](R)a methylhistamine binding to rat tissues. *Japanese Journal of Pharmacology.* 65 (2):_107–112.

Zhu, Y., Michalovich, D., Wu, H., Tan, K. B., Dytko, G. M., Mannan, 1. J., Boyce, R., Alston, J. Tierney, L. A., Li, X., Herrity, N. C., Vawter, L., Sarau, H. M., Ames, R. S., Davenport, C. M., Hieble, J. P., Wilson, S., Bergsma, D. J. et al. (2001) Cloning, expression, and pharmacological characterization of a novel human histamine receptor. *Molecular pharmacology.* 59(3): 434–441, 2001.

241000. Brown, C. M., Mackinnon, A. C., McGrath, J. C., Spedding, M., Kilpatrick, A. T. (1990) a2-Adrenoceptor subtypes and imidazoline-like binding in the rat brain. Br. J. Pharmacol. 99:803–809.

243510. Chin, J., Cameron, P. M., Rupp, E., and Schmidt, J. A. (1987) Identification of a high affinity receptor for native interleukin-1 a and interleukin-1 b on normal human lung fibroblasts. *J. Exp. Med.* 165:70–86.

250600. Bruns, R. F., Thomsen, W. J., Pugsley, T. A. (1983) Binding of leukotrienes C4 and D4 to membranes from guinea pig lung: regulation by ions and guanine nucleotides. *Life Sci.* 33:645–653.

Mong, S., Wu, H.-L, Hogabaoom, G. K., Clark, M. A., Crooke, S. T. (1984) Characterization of the leukotriene D4 receptor in guinea pig lung. *Eur. J. Pharmacol.* 102:1–11.

252600. Buckley, N J., Bonner, T. I., Buckley, C. M., Brann, M. R. (1989) Antagonist binding properties of five clonal muscarinic receptors expressed in CHO-K1 cell. *Mot. Pharmacol.* 35:469–476.

Luthin, G. R. and Wolfe, B. B. (1984) Comparison of [3H]pirenzepine and 3H]quinuctidinyl-benzilate binding to muscarine cholinergic receptors in rat brain. *J. Pharmacol. Exp. Ther.* 228:648–665.

Watson, M., Yamamura, H. I., and Roeske, W. R. (1983) A unique regulatory profile and regional distribution of [3H]prienzepine binding in the rat provide evidence for distinct M1 and M2 muscarinic receptor subtypes. *Life Sci.* 32:3001–3011.

252700. Buckley, N. J., Bonner, T. I., Buckley, C. M., Brann, M. R. (1989) Antagonist binding properties of five clonal muscarinic receptors expressed in CHO-Kt cell. *Mot. Pharmacol.* 35:469–476.

Delmendo, R. E, Michel, A. D., and Whiting, R. L. (1989) Affinity of muscarinic receptor antagonists for the three putative muscarinic binding sites. Br. J. Pharmacol. 96:457–464.

252800. Buckley, N J., Bonner, T. I., Buckley, C. M., Brann, M. R. (1989) Antagonist binding properties of five clonal muscarinic receptors expressed in CHO-K1 cell. *Mot. Pharmacol.* 35:469–476.

255510. Patacchini, R. and Maggi, C. A. (1995) Tachykinin receptors and receptor subtypes. *Arch. Int. Pharmacodyn.* 329:161–184.

257000. Fuhlendorff, J., Gether, U., Aakerlund, L., Langeland-Hohansen, N., Thogersen, H., Melberg, S. G., Olsen, U. B., Thastrup, 0., and Schwartz, T. W. (1990) [Leu31, Pro34]neuropeptide Y: a specific Y1 receptor agonist. *Proc. Natl. Acad. Sci. USA* 87:182–186.

Sheikh, S. P., O'Hare, M. M., Tortroa, 0., Schwartz, T. W. (1989) Binding of monoiodinated neuropeptide Y to hippocampal membranes and human neuroblastoma cell line. *J. Biol. Chem.* 264:6648–6654.

257110. Rose, P. M., Fernandes, P., Lynch, J. S., Frazier, S. T., Fisher, S. M., Kodukuta, K., Kienzle, B., and Seethala, R. (1995) Cloning and functional expression of a cDNA encoding a human type 2 neuropeptide Y receptor. *J. Biol. Chem.* 270(39):22661–22664.

258590. Davila-Garcia, M. 1., Musachio, J. L., Perry, D. C., Xiao, Y., Horti, A., London, E. D., Dannals, R. F. and Kellar, K. J. (1997) [1251]IPH, an epibatidine analog, binds with high affinity to neuronal nicotinic cholinergic receptors. The journal of pharmacology and experimental therapeutics. Z821: 445–451.

258590. Whiteaker, P., Jimenez, M., McIntosh, J. M., Collins, A. C. and Marks, M. J. (2000) Identification of a novel nicotinic binding site in mouse brain using [(125) 1]-epibatidine. *British journal of pharmacology.* 131(4): 729–739.

260110. Simonin, F. et al. (1994) The human d-opioid receptor: Genomic organization, cDNA cloning, functional expression, and distribution in human brain. *Mol. Pharmacol.* 46: 1015–1021.

260210. Patricia, M., et al. (1992) Pharmacological profiles of fentanyl analogs as + and + opiate receptors. *Eur. J Pharmacol.* 213: 219–225.

Simonin, F., et al. (1995) Kappa-opioid receptor in humans: cDNA and genomic cloning, chromosomal assignment, functional expression, pharmacology and expression pattern in the central nervous system. *PNAS U.S.A.* 92 15: 1431–1437.

260410. Wang, J. B., Johnson, P. S., Persico, A. M., Hawkins, A. L., Griffin, C. A., and Uhl, G. R. (1994) Human mu opiate receptor: cDNA and genomic clones, pharmacologic characterization and chromosomal assignment. *FEBS Lett.* 338:217–222.

264500. Ashendel, C. L. (1985) The phorbol ester receptor: a phospholipid-regulated protein kinase. *Biochem. Biophys. Acta* 822:219–242.

265010. Herbert, J. M., Castro-Faria-Neto, H. C., Barbosa-Filho, J. M., Cordeiro, R. S. B., Tibirica, E. (1997) Pharmacological evidence for the putative existence of two different subtypes of PAF receptors on platelets and leukocytes; studies with yangambin. J. Lipid Mediat. *Cell Signal.* 17: 1–14.

265600. Gaines, K. L., Hamilton, S. Boyd, A. E. 3rd (1988) Characterizatrion of the sulfonylurea receptor on beta cell membranes. J. Biol. Chem. 263:2589–2592.

268700. Bo, X., and Burnstock, G. (1990) High- and low-affinity binding sites for [3H]-a,b-methylene ATP in rat urinary bladder membranes. Br. J. Pharmacol. 101:291–296.

Ziganshin, A. U., Hoyle, C. H., Bo, X., Lambrecht, G., Mutschler, E., Baumert, H. G., Burnstock. G. (1993) PPADS selectively antagonized P2X-purinoceptor-mediated responses in the rabbit urinary bladder. Br. J. Pharmacol. 110:1491–1495.

268810. Boyer, J. L., Cooper, C. L. and Harden T. K. (1990) [$^{132}$P]3'-0-(4-Benzoyi)benzoyl ATP as a photoaffinity label for a phospholipase C-coupled P2Y-Purinergic receptor. *J. Biol Chem. Vol.* 265 No. 23: pp. 13515–13520.

271110. Martin, G. R. and Humphrey, P. P. A. (1994) Receptor for 5-hydroxytryptamine: current perspectives on classification and nomenclature. *Neuropharm.* 33:261–273.

271910. 1. Millerk, W. E., Fletcher, P. W., and Teitler, M. (1992) Membrane-bound and solubilized brain 5-HT3 receptor: improved radioligand binding assay using bovine area postrema or rat cortex and the radioligand [3H]GR65630, [3H]BRL43694, and [3H]LY278584 *Synapase,* 11:58–66.

Boess, F. G., Steward, L. J., Steele, J. A., Liu, D., Reid, J., Glencorse, T. A. and Martin, 1. L. (1997) Analysis of the ligand binding site of the 5-HT, receptor using site-directed mutagenesis: importance of glutamate 106. *Neuropharmacology,* 36: 637–647.

274020. Gu, H., Wall, S., Rudnick, G. (1994) Stable expression of biogenic akin transporters reveals differences in inhibitor sensitivity, kinetics, and ion dependence. *J. Biol. Chem.* 269(10):7124–7130.

278110. Ganapathy, M. E., Prasad, P. D., Huang, W., Seth, P., Leibach, F. H. and Ganapathy, V. (1999) Molecular and ligand-binding characterization of the s-receptor in the Jurkat human T lymphocyte cell line. *Pharmacol Exp. Ther* 289: 251–260.

278200. Hashimoto, K., and London, E. D. (1993) Further characterization of [3H]Ifenprodil binding to sigma receptors in rat brain. *Eur. J. Pharmacol.* 236:159–163.

279450. Doucette, G. J. Logan, M. M., Ramsdell, J. S. and Van Dolah, F. M. (1997) Development and preliminary validation of a microtiter plate-based receptor binding assay for paralytic shellfish poisoning toxins. *Toxicon*, 35 (5): 625–636.

279510. Catterall, W. A., Morrow, C. S., Daly, J. W., Brown, G. B. (1981) Binding of batrachotoxin A 20-alpha-benzoate to a receptor site associated with sodium channels in synaptic nerve ending particles. *J. Biol. Chem.* 256: 8922–8927.

285010. Chang, C. and Liao, S. (1987) Topographic recognition of cyclic hydrocarbons and related compounds by receptors for androgens, estrogens, and glucocorticoids. *J. Steroid Biochem.* 27(1–3): 123–131.

Traish, A. M., Muller R. E. and Wotiz, H. H. (1986) Binding of 7a, 17a-dimethyl-19-nortestosterone (mibolerone) to androgen and progesterone receptors in human and animal tessues. *Endocrinology* 118(4):_1327–1333.

EXAMPLE 9

Biological Testing of CS1814, CS1713, and CS1714

The results from the biological testing of CS1814, CS1713, CS1714, and various reference compounds are presented in FIGS. 41–58 and 60–62. The methods employed have been adapted from the scientific literature to maximize reliability and reproducibility. Reference standards were run as an integral part of each assay to ensure the validity of the results obtained. Assays were performed under the conditions described below. The literature reference(s) for each assay are are listed below.

Where presented, $IC_{50}$ values were determined by a non-linear, least squares regression analysis using Data Analysis Toolbox™ (MDL Information Systems, San Leandro, Calif., USA). Where inhibition constants ($K_i$) are presented, the $K_i$ values were calculated using the equation of Cheng and Prusoff (Cheng, Y., Prusoff, W. H., Biochem. Pharmacol. 22:3099–3108, 1973) using the observed $IC_{50}$ of the tested compound, the concentration of radioligand employed in the assay, and the historical values for the $K_D$ of the ligand (obtained experimentally at MDS Pharma Sarvices.

Where presented, the Hill coefficient (nH), defining the slope of the competitive binding curve, was calculated using Data Analysis Toolbox™. Hill coefficients significantly different than 1.0, may suggest that the binding displacement does not follow the laws of mass action with a single binding site. Where $IC_{50}$, $K_1$, and/or $n_H$ data are presented without Standard Error of the Mean (SEM), data are insufficient to be quantitative, and the values presented ($K_i$, $IC_{50}$, $n_H$) should be interpreted with caution.

CS1713 (Vial #2), CS1714 (Vial #3), and CS1814 (Vial #1) were evaluated for inhibition of cellular Serotonin and Norepinephrine Uptake. In addition, CS1713 (Vial #2) and CS1714 (Vial #3) were evaluated in various radioligand binding assays, and for inhibition of CYP450 3A4 at initial concentrations of 10 µM. As depicted in FIG. 60, significant activity ($\geq$50%) was observed for displacement of radioligand from Serotonin Transporter binding sites (Vial #2 Ki=3.88 nM, Vial #3 Ki=8.15 nM) and Norepinephrine Transporter binding sites (Vial #2 Ki=0.112 µM, Vial #3 Ki=1.68 µM).

As depicted in FIG. 61, CS1814 (Vial #1) is approximately equipotent in inhibiting serotonin and norepinephrine uptake ($IC_{50}$=28.6 nM for norepinephrine, $IC_{50}$=21.7 nM for serotonin). Interestingly, CS1713 (Vial #2) is a more potent inhibitor of norepinephrine uptake than serotonin uptake ($IC_{50}$=10.3 nM for norepinephrine, $IC_{50}$=22 nM for serotonin). In contrast, CS1714 (Vial #3) is a more potent inhibitor of serotonin uptake compared to norepinephrin uptake ($IC_{50}$=88.5 nM for norepinephrine, $IC_{50}$=40.3 nM for serotonin). The fact that CS1713 (Vial #2) is a more potent inhibitor of norepinephrine uptake would render it a superior therapeutic agent for treating diseases linked to norepinephrine uptake. In addition, the CS1714 (Vial #3) would useful for treating conditions requiring selective inhibition of serotonin uptake.

Importantly, no cytotoxicity was observed for CS1713 (Vial #2), CS1714 (Vial #3), or CS1814 (Vial #1) at 10 µM. In addition, CS1814 (Vial #1) is a selective inhibitor of norepinephrine and serotonin transporters. The fact that CS1814 generally does not bind well to other receptors, as depicted in FIGS. 32 and 33, substantially reduces the risk of negative side effects associated with administering the compound to a patient. Therefore, it is likely that CS1713 and CS1714 will not have detrimental side effects.

Methods

| 118090 CYP450, 3A4 | | 212610 Bradykinin $B_2$ | |
|---|---|---|---|
| Source: | Human recombinant Sf9 insect cells | Source: | Human recombinant CHO-K1 cells |
| Substrate: | 50 µM 7-benzyloxy-4-(trifluoromethyl)-coumarin | Ligand: | 0.2 nM [$^3$H] Bradykinin |
| | | Vehicle: | 1% DMSO |
| Vehicle: | 0.1% DMSO | Incubation Time/Temp: | 90 minutes @ 25° C. |
| Pre-Incubation Time/Temp: | None | Incubation Buffer: | 24 mM TES-NH$_4$OH, pH 6.8, 1 mM 1,10-phenanthroline, 0.3% BSA |
| Incubation Time/Temp: | 30 minutes @ 37° C. | | |
| Incubation Buffer: | 75 mM Potassium Phosphate buffer, pH 7.5 | Non-Specific Ligand: | 5 µM Bradykinin |
| | | $K_D$: | 0.29 nM* |
| | | $B_{MAX}$: | 2 pmole/mg Protein* |
| Quantitation Method: | Spectrofluorimetric quantitation of 7-Hydroxy-4-(trifluoromethyl)-coumarin | Specific Binding: | 90%* |
| | | Quantitation Method: | Radioligand Binding |
| | | Significance Criteria: | $\geq$50% of max stimulation or inhibition |
| Significance Criteria: | $\geq$50% of max stimulation or | | |

214510 Calcium Channel L-Type, Benzothiazepine inhibition

| | |
|---|---|
| Source: | Wistar Rat brain |
| Ligand: | 2 nM [$^3$H] Diltiazem |
| Vehicle: | 1% DMSO |
| Incubation Time/Temp: | 3 hours @ 4° C. |
| Incubation Buffer: | 50 mM Tris-HCl, 0.1% BSA, pH 7.4 at 25° C. |
| Non-Specific Ligand: | 10 µM Diltiazem |
| $K_D$: | 0.016 µM* |
| $B_{MAX}$: | 0.21 pmole/mg Protein* |
| Specific Binding: | 73%* |
| Quantitation Method: | Radioligand Binding |
| Significance Criteria: | ≧50% of max stimulation or inhibition |

204410 Transporter, Norepinephrine (NET)

| | |
|---|---|
| Source: | Human recombinant MDCK cells |
| Ligand: | 0.2 nM [$^{125}$I] RTI-55 |
| Vehicle: | 1% DMSO |
| Incubation Time/Temp: | 3 hours @ 4° C. |
| Incubation Buffer: | 50 mM Tris-HCl, 100 mM NaCl, 1 µM leupeptin, 10 µM PMSF, pH 7.4 |
| Non-Specific Ligand: | 10 µM Desipramine |
| $K_D$: | 0.024 µM* |
| $B_{MAX}$: | 2.5 pmole/mg Protein* |
| Specific Binding: | 75%* |
| Quantitation Method: | Radioligand Binding |
| Significance Criteria: | ≧50% of max stimulation or inhibition |

274020 Transporter, Serotonin (5-Hydroxytryptamine) (SERT)

| | |
|---|---|
| Source: | Human recombinant HEK-293 cells |
| Ligand: | 0.15 nM [$^{125}$I] RTI-55 |
| Vehicle: | 1% DMSO |
| Incubation Time/Temp: | 3 hours @ 4° C. |
| Incubation Buffer: | 100 mM NaCl, 50 mM Tris HCl, 1 µM Leupeptin, 10 µM PMSF, pH 7.4 |
| Non-Specific Ligand: | 10 µM Imipramine |
| $K_D$: | 0.17 nM* |
| $B_{MAX}$: | 0.41 pmole/mg Protein* |
| Specific Binding: | 95%* |
| Quantitation Method: | Radioligand Binding |
| Significance Criteria: | f 50% of max stimulation or inhibition |

302100 Cytotoxicity, Norepinephrine Uptake

| | |
|---|---|
| Target: | Human MDCK cells Dog kidney |
| Vehicle: | 0.4% DMSO |
| Incubation Time/Temp: | 30 minutes @ 25° C. |
| Incubation Buffer: | 5 mM Tris-HCl, 7.5 mM HEPES, 120 mM NaCl, 5.4 mM KCl, 1.2 mM CaCl$_2$, 1.2 mM MgSO$_4$, 5 mM Glucose, 1 mM Ascorbic Acid, pH 7.1 |
| Quantitation Method: | Spectrofluorimetric quantitation of Alamar Blue |
| Significance Criteria-Ag: | N/A |
| Significance Criteria-Ant: | ≧50% Decrease in fluorescence intensity relative to vehicle control |

364100 Cytotoxicity, Serotonin (5-Hydroxytryptamine) Uptake

| | |
|---|---|
| Target: | Human HEK-293 cells Huamn embryonal kidney |
| Vehicle: | 0.4% DMSO |
| Incubation Time/Temp: | 30 minutes @ 25° C. |
| Incubation Buffer: | 5 mM Tris-HCl, 7.5 mM HEPES, 120 mM NaCl, 5.4 mM KCl, 1.2 mM CaCl$_2$, 1.2 mM MgSO$_4$, 5 mM Glucose, 1 mM Ascorbic Acid, pH 7.1 |
| Quantitation Method: | Spectrofluorimetric quantitation of Alamar Blue |
| Significance Criteria-Ag: | N/A |
| Significance Criteria-Ant: | ≧50% Decrease in fluorescence intensity relative to vehicle control |

302000 Uptake, Norepinephrine

| | |
|---|---|
| Target: | Human MDCK cells Dog kidney |
| Vehicle: | 0.4% DMSO |
| Incubation Time/Temp: | 10 minutes @ 25° C. |
| Incubation Buffer: | 5 mM Tris-HCl, 7.5 mM HEPES, 120 mM NaCl, 5.4 mM KCl, 1.2 mM CaCl$_2$, 1.2 mM MgSO$_4$, 5 mM Glucose, 1 mM Ascorbic Acid, pH 7.1 |
| Quantitation Method: | Quantitation of [$^3$H]Norepinephrine |
| Significance Criteria-Ag: | N/A |
| Significance Criteria-Ant: | ≧50% Inhibition of [$^3$H]Norepinephrine uptake relative to desipramine response |

364000 Uptake, Serotonin (5-Hydroxytryptamine)

| | |
|---|---|
| Target: | Human HEK-293 cells Human embryonic kidney |
| Vehicle: | 0.4% DMSO |
| Incubation Time/Temp: | 10 minutes @ 25° C. |
| Incubation Buffer: | 5 mM Tris-HCl, 7.5 mM HEPES, 120 mM NaCl, 5.4 mM KCl, 1.2 mM CaCl$_2$, 1.2 mM MgSO$_4$, 5 mM Glucose, 1 mM Ascorbic Acid, pH 7.1 |
| Quantitation Method: | Quantitation of [$^3$H]Serotonin uptake |
| Significance Criteria-Ag: | N/A |
| Significance Criteria-Ant: | ≧50% Inhibition of [$^3$H]Serotonin uptake relative to fluxetine response |

LITERATURE REFERENCES (CAT. #. Reference)

118090. Crespi, C. L., Miller, V. P and Penman, B. W. (1997) Microtiter plate assays for inhibition of human, drug-metabolizing cytochromes P450. *Anal Biochem* 248(1): 188–190.

Gentest Technical Bulletin (Version 4.2: Revised 27 Sep. 2000) A high throughput method for measuring cytochrome P450 inhibition. *Gentest Technical Bulletin* (Version 4.2) Revised 27 Sep. 2000).

204410. Galli, A., DeFelice, L., Duke, B.-J., Moore, K. Blakely, R. (1995) Sodium dependent norepinephrine induced currents in norephinephrine transporter transfected HEK293 cells blocked by cocaine and antidepressants. *J. Exp. Biol.* 198:2197–2212.

212610. Eggerickx, D., Raspe, E. Bertrand, D., Vassart, G., Parmentier, M. (1992) Molecular cloning, functional expression and pharmacological characterization of a human bradykinin B2 receptor gene. *Biochem Biophys Res Commun* 187 (3): 1306–1313.

214510. Schoemaker, H. and Langer, S. Z. (1985) [3H] Diltiazem binding to calcium channel antagonist recognition sites in rat cerebral cortex. *Eur. J. Pharmacol.* 111:273–277.

274020. Gu, H., Wall, S., Rudnick, G. (1994) Stable expression of biogenic akin transporters reveals differences in inhibitor sensitivity, kinetics, and ion dependence. *J. Biol. Chem.* 269(10):7124–7130.

302000. Galli, A., DeFelice, L. Duke, B.-J., and Blakely, R. (1995) Sodium dependent norephinephrine-induced currents in norepinephrine-transporter-transfected HEK-293 cells blocked by cocaine and antidepressants. *J. Exp. Biol.* 198:2197–2212.

302100. Page, B., Page, M. and Noel, C. (1993) A new fluorometric assay for cytotoxicity measurements in vitro. *Ing. I* 3:473–476, 1993.

364000. Gu, H., Wall, S., Rudnick, G. (1994) Stable expression of biogenic akin transporter reveals differences in inhibitor sensitivity, kinetics, and ion dependence. *J. Biol. Chem.* 269(1):7124–7130.

364100. Page, B., Page, M. and Noel, C. (1993) A new fluorometric assay for cytotoxicity measurements in vitro. *Int. J. Oncology* 3:473–476, 1993.

ADDITIONAL PATENTS AND PUBLICATIONS CITED

1. U.S. Pat. No. 4,478,836.
2. U.S. Pat. No. 5,034,541.
3. U.S. Pat. No. 5,621,142.
4. Moret, C. et al. *Neuropharmacology* 1985, 24, 1211–1219.
5. Bonnaud, B. et al. *J. Med. Chem.* 1987, 30, 318–325.
6. Shuto, S. et al. *J. Med. Chem.* 1995, 38, 2964–2968.
7. Viazzo, P. et al. *Tetrahedron Lett.* 1996, 37, 4519–4522.
8. Shuto, S. et al. *Tetrahedron Lett.* 1996, 37, 641–644.
9. Shuto, S. et al. *J. Med. Chem.* 1996, 39, 4844–4852.
10. Shuto, S. et al. *J. Med. Chem.* 1998, 41, 3507–3514.
11. Deprez, D. et al. *Eur. J. Drug Metab. Pharmacokinet.* 1998, 23, 166–171.
12. Puozzo, C. et al. *Eur. J. Drug Metab. Pharmacokinet.* 1998, 23, 273–279.
13. Puozzo C. et al. *Eur. J. Drug Metab. Pharmacokinet.* 1998, 23, 280–286.
14. Shuto, S. et al. *Jpn. J. Pharmacol.* 2001, 85, 207–213.
15. Doyle, M. P. et al. *Adv. Synth. Catal.* 2001, 343, 299–302.
16. Kazuta, Y. et al. *Bioorg. Med. Chem.* 2002, 10, 1777–1791.
17. Labat, L. et al. *J. Chromatogr. B* 2002, 773, 17–23.
18. Grard, S. et al. *Electrophoresis* 2000, 21, 3028–3034.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated compound represented by A:

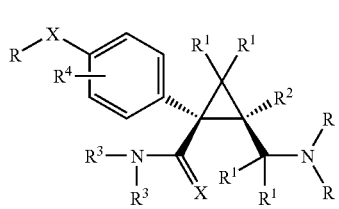

wherein

X represents independently for each occurrence O or S;

R represents independently for each occurrence H;

$R^1$ represents independently for each occurrence H;

$R^2$ represents independently for each occurrence H;

$R^3$ represents independently for each occurrence H, alkyl, cycloalkyl, alkenyl, or arylalkyl;

$R^4$ is absent or present between one and four times inclusive;

$R^4$, if present, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —$(CH_2)_m$—$R_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

2. An isolated compound represented by B:

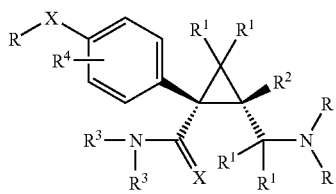

wherein
X represents independently for each occurrence O or S;
R represents independently for each occurrence H;
$R^1$ represents independently for each occurrence H;
$R^2$ represents independently for each occurrence H;
$R^3$ represents independently for each occurrence H, alkyl, cycloalkyl, alkenyl, or arylalkyl;
$R^4$ is absent or present between one and four times inclusive;
$R^4$, if present, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or $-(CH_2)_m-R_{80}$;
$R_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof.

3. The compound of claim 1 or 2, wherein X represents O.

4. The compound of claim 1 or 2, wherein $R^3$ represents alkyl.

5. The compound of claim 1 or 2, wherein $R^4$ is absent.

6. The compound of claim 1 or 2, wherein X represents O; and $R^3$ represents alkyl.

7. The compound of claim 1 or 2, wherein X represents O; $R^3$ represents alkyl; and $R^4$ is absent.

8. The compound of claim 1 or 2, wherein X represents O; $R^3$ represents ethyl; and $R^4$ is absent.

9. A formulation, comprising a compound of claim 1 or 2; and a pharmaceutically acceptable excipient.

10. A formulation, comprising a compound of claim 1 or 2; and a compound selected from the group consisting of analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastrointestinal drugs, muscle relaxants, nutritional agents, vitamins, parasympathomimetics, stimulants, antinarcoleptic, and anorectics.

11. A formulation, comprising a compound of claim 1 or 2; and a compound selected from the group consisting of aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil, molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, and zopiclone.

12. A method of treating a mammal suffering from depression, comprising the step of:
administering to said mammal a therapeutically effective amount of an isolated compound represented by A:

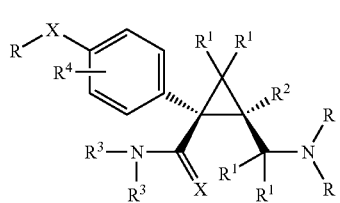

wherein
X represents independently for each occurrence O or S;
R represents independently for each occurrence H;
represents independently for each occurrence H;
R² represents independently for each occurrence H;
R³ represents independently for each occurrence H, alkyl, cycloalkyl, alkenyl, or arylalkyl;
R⁴ is absent or present between one and four times inclusive;
R⁴, if present, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkiloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;
R$_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof; or
an isolated compound represented by B:

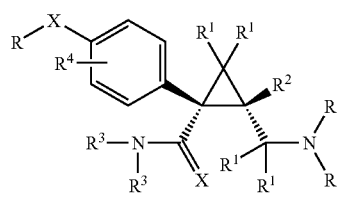

B wherein
X represents independently for each occurrence O or S;
R represents independently for each occurrence H;
R¹ represents independently for each occurrence H;
R² represents independently for each occurrence H;
R³ represents independently for each occurrence H, alkyl, cycloalkyl, alkenyl, or arylalkyl;
R⁴ is absent or present between one and four times inclusive;
R⁴, if presents, represents independently for each occurrence H, alkyl, cycloalkyl, alkenyl, aryl, heteroaryl, arylalkyl, cyano, halogen, hydroxyl, alkoxyl, aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylalkylamino)carbonyl, alkylsulfonyl, arylsulfonyl, or —(CH$_2$)$_m$—R$_{80}$;
R$_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof.

13. A method of treating a mammal suffering from fibromyalgia syndrome, comprising the step of:
administering to said mammal a therapeutically effective amount of an isolated compound represented by A:

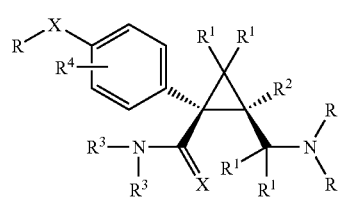

A wherein
X represents independently for each occurrence O or S;
R represents independently for each occurrence H;
R¹ represents independently for each occurrence H;
R² represents independently for each occurrence H;
R³ represents independently for each occurrence H, alkyl, cycloalkyl, alkenyl, or arylalkyl;
R⁴ is absent or present between one and four times inclusive;
R⁴, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —(CH$_2$)$_m$—R$_{80}$;
R$_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof; or
an isolated compound represented by B:

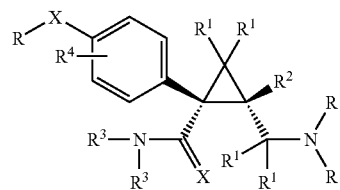

B wherein
X represents independently for each occurrence O or S;
R represents independently for each occurrence H;
R¹ represents independently for each occurrence H;
R² represents independently for each occurrence H;
R³ represents independently for each occurrence H, alkyl, cycloalkyl, alkenyl, or arylalkyl;
R⁴ is absent or present between one and four times inclusive;
R⁴, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

14. A method of treating a mammal suffering from mental disorders including Functional Somatic Disorders, for example, depression, fibromyalgia syndrome, chronic fatigue syndrome, pain, attention deficit/hyperactivity disorder, and visceral pain syndromes (VPS), such as irritable bowel syndrome (IBS), noncardiac chest pain (NCCP), functional dyspepsia, interstitial cystitis, essential vulvodynia, urethral syndrome, orchialgia, and affective disorders, including depressive disorders (major depressive disorder, dysthymia, atypical depression) and anxiety disorders (generalized anxiety disorder, phobias, obsessive compulsive disorder, panic disorder, post-traumatic stress disorder), premenstrual dysphoric disorder, temperomandibular disorder, atypical face pain, migraine headache, and tension headache, comprising the step of:

administering to said mammal a therapeutically effective amount of an isolated compound represented by A:

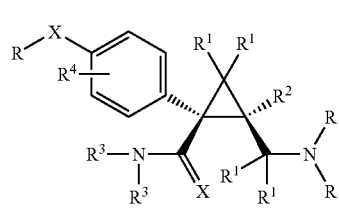

A wherein

X represents independently for each occurrence O or S;

R represents independently for each occurrence H;

$R^1$ represents independently for each occurrence H;

$R^2$ represents independently for each occurrence H;

$R^3$ represents independently for each occurrence H, alkyl, cycloalkyl, alkenyl, or arylalkyl;

$R^4$ is absent or present between one and four times inclusive;

$R^4$, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof; or an isolated compound represented by B:

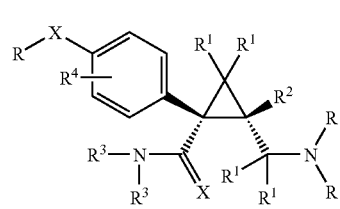

B wherein

X represents independently for each occurrence O or S;

R represents independently for each occurrence H;

$R^1$ represents independently for each occurrence H;

$R^2$ represents independently for each occurrence H;

$R^3$ represents independently for each occurrence H, alkyl, cycloalkyl, alkenyl, or arylalkyl;

$R^4$ is absent or present between one and four times inclusive;

$R^4$, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;

$R_{80}$ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

15. The method of claim 12, 13, or 14, wherein said mammal is a primate, equine, canine or feline.

16. The method of claim 12, 13, or 14, wherein said mammal is a human.

17. The method of claim 12, 13, or 14, wherein said compound is administered orally.

18. The method of claim 12, 13, or 14, wherein said compound is administered intravenously.

19. The method of claim 12, 13, or 14, wherein said compound is administered sublingually.

20. The method of claim 12, 13, or 14, wherein said compound is administered ocularly.

21. The method of claim 12, 13, or 14, wherein said compound is administered transdermally.

22. The method of claim 12, 13, or 14, wherein said compound is administered rectally.

23. The method of claim 12, 13, or 14, wherein said compound is administered vaginally.

24. The method of claim 12, 13, or 14, wherein said compound is administered topically.

25. The method of claim 12, 13, or 14, wherein said compound is administered intramuscularly.

26. The method of claim 12, 13, or 14, wherein said compound is administered subcutaneously.

27. The method of claim 12, 13, or 14, wherein said compound is administered buccally.

28. The method of claim 12, 13, or 14, wherein said compound is administered nasally.

29. A composition comprising a selective serotonin reuptake inhibitor and an isolated compound represented by A:

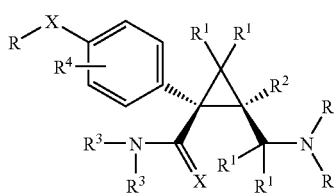

wherein
X represents independently for each occurrence O or S;
R represents independently for each occurrence H;
$R^1$ represents independently for each occurrence H;
$R^2$ represents independently for each occurrence H;
$R^3$ represents independently for each occurrence H, alkyl, cycloalkyl, alkenyl, or arylalkyl;
$R^4$ is absent or present between one and four times inclusive;
$R^4$, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;
$R_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof; or
an isolated compound represented by B:

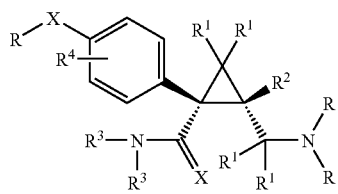

wherein
X represents independently for each occurrence O or S;
R represents independently for each occurrence H;
$R^1$ represents independently for each occurrence H;
$R^2$ represents independently for each occurrence H;
$R^3$ represents independently for each occurrence H, alkyl, cycloalkyl, alkenyl, or arylalkyl;
$R^4$ is absent or present between one and four times inclusive;
$R^4$, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;
$R_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof.

30. A composition comprising a selective norepinephrine reuptake inhibitor and an isolated compound represented by A:

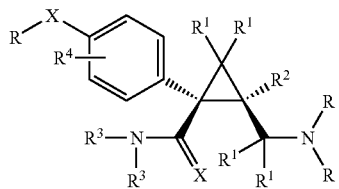

wherein
X represents independently for each occurrence O or S;
R represents independently for each occurrence H;
$R^1$ represents independently for each occurrence H;
$R^2$ represents independently for each occurrence H;
$R^3$ represents independently for each occurrence H, alkyl, cycloalkyl, alkenyl, or arylalkyl;
$R^4$ is absent or present between one and four times inclusive;
$R^4$, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino)carbonyl, (arylakylamino)carbonyl, alkylsulfonyl, arylsulfonyl, or —$(CH_2)_m$—$R_{80}$;
$R_{80}$ represents independently for each occurrence an aryl, cycloalkyl, cycloalkenyl, heterocyclyl, or polycyclyl moiety;
m is independently for each occurrence an integer in the range 0 to 8 inclusive; and
the compound is a single enantiomer; or
a pharmaceutically acceptable salt or prodrug thereof; or
an isolated compound represented by B:

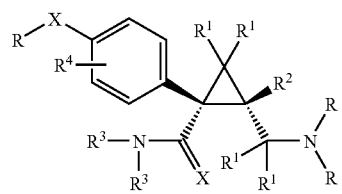

wherein
X represents independently for each occurrence O or S;
R represents independently for each occurrence H;

R¹ represents independently for each occurrence H;

R² represents independently for each occurrence H;

R³ represents independently for each occurrence H, alkyl, cycloalkyl, alkenyl, or arylalkyl;

R⁴ is absent or present between one and four times inclusive;

R⁴, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino) carbonyl, (arylakylamino)carbonyl, alkylsulfonyl, arylsulfonyl, or —(CH₂)ₘ—R₈₀;

R₈₀ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

31. A composition comprising a selective serotonin reuptake inhibitor, a selective norepinephrine reuptake inhibitor, and an isolated compound represented by A:

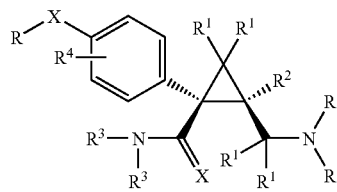

wherein

X represents independently for each occurrence O or S;

R represents independently for each occurrence H;

R¹ represents independently for each occurrence H;

R² represents independently for each occurrence H;

R³ represents independently for each occurrence H, alkyl, cycloalkyl, alkenyl, or arylalkyl;

R⁴ is absent or present between one and four times inclusive;

R⁴, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino) carbonyl, (arylakylamino)carbonyl, alkylsulfonyl, arylsulfonyl, or —(CH₂)ₘ—R₈₀;

R₈₀ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof; or an isolated compound represented by B:

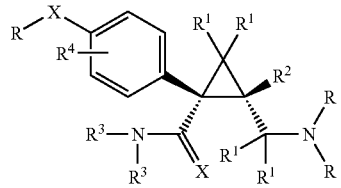

wherein

X represents independently for each occurrence O or S;

R represents independently for each occurrence H;

R¹ represents independently for each occurrence H;

R² represents independently for each occurrence H;

R³ represents independently for each occurrence H, alkyl, cycloalkyl, alkenyl, or arylalkyl;

R⁴ is absent or present between one and four times inclusive;

R⁴, if present, represents independently for each occurrence H, alkyl, cycloalkyl, alkenyl, aryl, heteroaryl, arylalkyl, cyano, halogen, hydroxyl, alkoxyl aryloxy, arylalkyloxy, amino, alkylamino, arylamino, arylakylamino, sulfhydryl, alkylthio, arylthio, arylakylthio, nitro, azido, alkylseleno, formyl, acyl, carboxyl, silyl, silyloxy, (alkyloxy)carbonyl, (aryloxy)carbonyl, (arylalkyloxy)carbonyl, (alkylamino)carbonyl, (arylamino) carbonyl, (arylakylamino)carbonyl, alkylsulfonyl, arylsulfonyl, or —(CH₂)ₘ—R₈₀;

R₈₀ represents independently for each occurrence an aryl, cycloalkyl, cycloalkenyl, heterocyclyl, or polycyclyl moiety;

m is independently for each occurrence an integer in the range 0 to 8 inclusive; and the compound is a single enantiomer; or a pharmaceutically acceptable salt or prodrug thereof.

32. The composition of claim 30 or 31, wherein said selective norepinephrine reuptake inhibitor is milnacipran.

33. The composition of any one of claims 29–31, wherein said isolated compound is the hydrochloride salt of

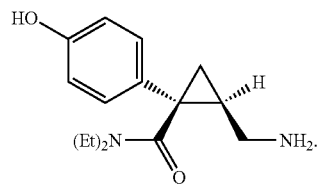

34. The composition of any one of claims 29–31, wherein said isolated compound is the hydrochloride salt of

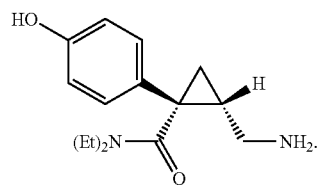

35. The composition of any one of claims 29–31, wherein said composition further comprises the hydrochloride salt of

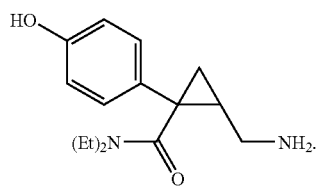

36. A composition comprising a selective serotonin reuptake inhibitor and the hydrochloride salt of

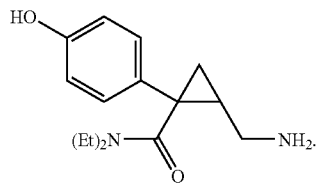

37. A composition comprising a selective norepinephrine reuptake inhibitor and the hydrochloride salt of

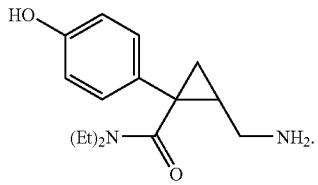

38. A composition comprising a selective serotonin reuptake inhibitor, a selective norepinephrine reuptake inhibitor, and the hydrochloride salt of

* * * * *